US010421978B2

(12) United States Patent
Moss et al.

(10) Patent No.: US 10,421,978 B2
(45) Date of Patent: Sep. 24, 2019

(54) INTERGENIC SITES BETWEEN CONSERVED GENES IN THE GENOME OF MODIFIED VACCINIA ANKARA (MVA) VACCINIA VIRUS

(71) Applicant: The USA, as represented by the Secretary, Dept. of Health and Human Services, Bethesda, MD (US)

(72) In

(56) References Cited

OTHER PUBLICATIONS

Sutter, Gerd, et al., "A recombinant vector derived from the host range-restricted and highly attenuated MVA strain of vaccinia virus stimulates protective immunity in mice to influenza virus" Vaccine, 1994, pp. 1032-1040, vol. 12, No. 11.
Timm, Alexandra et al., "Genetic stability of recombinant MVA-BN" Vaccine, May 22, 2006, pp. 4618-4621, vol. 24, No. 21.
Upton, Chris et al., "Poxvirus Orthologous Clusters: toward Defining the Minimum Essential Poxvirus Genome" Journal of Virology, Jul. 2003, pp. 7590-7600, vol. 77, No. 13.
Verheust, C., et al., "Biosafety aspects of modified vaccinia virus Ankara (MVA)-based vectors used for gene therapy or vaccination," Vaccine, 2012, 30:2623-2632.
Wyatt, et al., "Elucidating and Minimizing the Loss by Recombinant Vaccinia Virus of Human Immunodeficiency virus Gene Expression Resulting from Spontaneous Mutations and Positive Selection," J. Virol, vol. 83, No. 14, Jul. 2009, pp. 7176-7184, XP002663544.
International Search Report for International Patent Application No. PCT/IB2007/004575, dated May 18, 2009, 12 pages.
Written Opinion for International Patent Application No. PCT/IB2007/004575, dated May 29, 2009, 8 pages.
International Preliminary Report on Patentability for International Patent Application No. PCT/IB2007/004575, dated Jun. 3, 2009, 9 pages.
Official Action (with English translation) for Chinese Patent Application No. 200780035385.3, dated Nov. 1, 2010, 12 pages.
Official Action (with English translation) for Chinese Patent Application No. 200780035385.3, dated Apr. 25, 2011, 12 pages.
Official Action (with English translation) for Chinese Patent Application No. 200780035385.3, dated Nov. 2, 2011, 12 pages.
Official Action (with English translation) for Chinese Patent Application No. 200780035385.3, dated May 31, 2012, 11 pages.
Notice of Allowance (with English translation) for Chinese Patent Application No. 200780035385.3, dated Dec. 5, 2012, 3 pages.
Official Action (with English translation) for Chinese Patent Application No. 2013100549071, dated Feb. 18, 2014, 15 pages.
Official Action (with English translation) for Chinese Patent Application No. 2013100549071, dated Sep. 1, 2014, 14 pages.
Official Action for European Patent Application No. 07874019.8, dated Sep. 21, 2009, 6 pages.
Official Action for European Patent Application No. 07874019.8, dated Feb. 18, 2010, 3 pages.
European Search Report for European Patent Application No. 11183527.8, dated Nov. 25, 2011, 14 pages.
Extended European Search Report for European Patent Application No. 11183527.8, dated Mar. 19, 2012, 14 pages.
Restriction Requirement for U.S. Appl. No. 12/377,847, dated Feb. 14, 2012, 7 pages.
Official Action for U.S. Appl. No. 12/377,847, dated Jul. 17, 2012, 11 pages.
Final Action for U.S. Appl. No. 12/377,847, dated Apr. 15, 2013, 11 pages.
Official Action for U.S. Appl. No. 12/377,847, dated Jun. 19, 2014, 9 pages.
Official Action for U.S. Appl. No. 12/377,847, dated Oct. 1, 2014, 8 pages.
Notice of Allowance for U.S. Appl. No. 12/377,847, dated May 11, 2015 9 pages.
Official Action with English Translation for China Patent Application No. 201310054907.1, dated May 21, 2015 13 pages.
Database EMBL [Online], "Sequence 4 from Patent W02008142479." XP002614877, retrieved from EBI accession No. EMBL:GN340507 Database accession No. GN340507 compound; sequence 4, Apr. 27, 2009 (Apr. 27, 2009).
Vaccinia virus strain Ankara, complete genomic sequence, [Apr. 14, 2003] (online); [retrieved on Dec. 3, 2014]; GenBank Accession No. U94848; <URL; http://www.ncbi.nlm.nih.gov/nuccore/2772662?sat=I3&satkey=6641785>.
Colinas, RJ, et al., "A DNA ligase gene in the Copenhagen strain of vaccinia virus is nonessential for viral replication and recombination," Virology, Nov. 1990;179(1):267-75.
Earl et al: "Recombinant modified vaccinia virus Ankara provides durable protection against disease caused by an immunodeficiency virus as well as long-term immunity to an orthopoxvirus in a non-human primate", Virology, Academic Press,Orlando, US, vol. 366, No. 1, Aug. 29, 2007 (Aug. 29, 2007), pp. 84-97, XP022232345.
Wyatt et al: "Enhanced cell surface expression, immunogenicity and genetic stability resulting from a spontaneous truncation of HIV Env expressed by a recombinant MVA", Virology, Academic Press,Orlando, US, vol. 372, No. 2, Feb. 23, 2008 (Feb. 23, 2008), pp. 260-272, XP022496344.
Wyatt L et al: "P19-52 LB. Assessing and restructuring foreign gene insertion sites for enhanced stability of modified Vaccinia virus ankara recombinants expressing HIV genes", Retrovirology, Biomed Central Ltd., London, GB, vol. 6, No. Suppl 3, Oct. 22, 2009 (Oct. 22, 2009) p. P416, XP021064146.
Notice of Allowance for European Patent Application No. 11183527.8, dated Apr. 25, 2016 106 pages.
Balloul et al. Vaccinia virus strain MVATGN33.1 Modified Virus Ankara, complete genome, Accession EF675191.1, VRL Jul. 10, 2007.

* cited by examiner

| Chemokine coreceptor used | PBMC replication | Macrophage replication | T-cell-line replication | REplicative phenotype | Syncytium-inducing phenotype |
|---|---|---|---|---|---|
| X4 | + | – | + | Rapid/high | ++ |
| R5 | + | + | – | Slow/low | – |
| R5/X4 | + | + | + | Rapid/high | + |

EcoRI (1)
1   GAATTCCCTG GGACATACGT ATATTCTAT GATCTGTCTT ATATGAAGTC TATACAGGGA ATAGATTCAG
    CTTAAGGGAC CCTGTATGCA TATAAAGATA CTAGACAGAA TATACTTCAG ATATGTCGCT TATCTAAGTC

71  AATTTCTACA TAATTATATA TTGTACCCTA ATAAGTTTAA TCTAACACTC CCCGAAGATT TGTTTATAAT
    TTAAAGATGT ATTAATATAT AACATGGGAT TATTCAAATT AGATTGTGAG GGGCTTCTAA ACAAATATTA

141 CCCTACAAAT TTGGATATTC TATGGCGTAC AAAGGAATAT ATAGACTCGT TCGATATTAG TACAGAAACA
    GGGATGTTTA AACCTATAAG ATACCGCATG TTTCCTTATA TATCTGAGCA AGCTATAATC ATGTCTTTGT

211 TGGAATAAAT TATTATCCAA TTAATTATATG AAGATGATAG AGTAGCCTAA ACTTTATGTA CTAAGTCCTA
    ACCTTATTTA ATATAGGTT AATAATATAC TTCTACTATC TCATACGATT TGAAATACAT GATTCAGGAT

281 TTCTCGCTGA GGAGTTGGAT AATTTTGAGA GGACGGGAGA ATTAACTAGT ATTGTACAAG AAGCCATTTT
    AAGAGCGACT CCTCAACCTA TTAAAACTCT CCTGCCCTCT TAATTGATCA TAACATGTTC TTCGGTAAAA

351 ATCCTAAAT TTACCAATTA AGATTTTAAA TTTTAAACAT AAAGATCATG ATACGTATAT ACACTTTGT
    TAGAGATTTA AATGGTTAAT TCTAAAATT AAAATTTGTA TTTCTACTAC TATGCATATA TGTGAAACA

421 AAAATATTAT TCCGTGTCTA TAACGGAACA AACCCTACTA TATATTATCA TAGACCCTCTA ACGGATATA
    TTTTATAATA AGCCACAGAT ATTGCCTTGT TTGGGATGAT ATATATAGT ATCTGGAGAT TGCCCTATAT

AscI (539)
491 TGAATATGAT TTCAGATACT ATATTGTTC CTGTAGATAA TAACTAAGCC GCGCCTTTCA TTTCTTTTT
    ACTTATACTA AAGTCTATGA TATAAACAAG GACATCTATT ATTGATTCGG CGCGGAAAGT AAACAAAAA

```
561  TTCTATGCTA TRAATGGTGA GCAAGGGCGA GGAGCTGTTC ACCGGGGTGG TGCCCATCCT GGTCGAGCTG
     AAGATACGAT ATTTACCACT CGTTCCCGCT CCTCGACAAG TGGCCCCACC ACGGGTAGGA CCAGCTCGAC

631  GACGGGCGACG TAAACGGCCA CAAGTTCAGC GTGTCCCGCC AGGGCGAGGG CGATGCCACC TACGGCAAGC
     CTGCCGCTGC ATTTGCCGGT GTTCAAGTCG CACAGGGCGG TCCCGCTCCC GCTACGGTGG ATGCCGTTCG

701  TGACCCTGAA GTTCATCTGC ACCACCGGCA AGTTGCCCGT GCCCTGGCCC ACCCTCGTGA CCACCCTGAC
     ACTGGGACTT CAAGTAGACG TGGTGGCCGT TCGAGGGGCA CGGGACCGGG TGGGAGCACT GGTGGGACTG

771  CTACGGCGTG CAGTGCTTCA GCCGCTACCC CGACCACATG AAGCAGCACG ACTTCTTCAA GTCCGCCATG
     GATGCCGCAC GTCACGAAGT CGGCGATGGG GCTGGTGTAC TTCGTCGTGC TGAAGAAGTT CAGGCGGTAC

841  CCCGAAGGCT ACGTCCAGGA GCGCACCATC TTCTTCAAGG ACGACGGCAA CTACAAGACC CGGGCCGAGG
     GGGCTTCCGA TGCAGGTCCT CGCGTGGTAG AAGAAGTTCC TGCTGCCGTT GATGTTCTGG GCCGGCCTCC

911  TGAAGTTCGA GGGCGACACC CTGGTGAACC GCATCGAGCT GAAGGGCATC GACTTCAAGG AGGACGGCAA
     ACTTCAAGCT CCCGCTGTGG GACCACTTGG CGTAGCTCGA CTTCCCGTAG CTGAAGTTCC TCCTGCCGTT

981  CATCCTGGGG CACAAGCTGG AGTACAACTA CAACAGCCAC AACGTCTATA TCATGGCCGA CAAGCAGAAG
     GTAGGACCCC GTGTTCGACC TCATGTTGAT GTTGTCGGTG TTGCAGATAT AGTACCGGCT GTTCGTCTTC

1051 AACGGCATCA AGTGAACTT CAAGATCCGC CACAACATCG AGGACGGCAG CGTGCAGCTC GCCGACCACT
     TTGCCGTAGT TCCACTTGAA GTTCTAGGCG GTGTTGTAGC TCCTGCCGTC GCACGTCGAG CGGCTGGTGA
```

FIG. 8-2

```
1121 ACCAGCAGAA CACCCCCATC GGCGACGGCC CCGTGCTGCT GCCCGACAAC CACTACCTGA GCACCCAGTC
     TGGTCGTCTT GTGGGGGTAG CCGCTGCCGG GGCACGACGA CGGGCTGTTG GTGATGGACT CGTGGGTCAG

1191 CGCCCTGAGC AAAGACCCCA ACGAGAAGCG CGATCACATG GTCCTGCTGG AGTTCGTGAC CGCGGCCGGG
     GCGGGACTCG TTTCTGGGGT TGCTCTTCGC GCTAGTGTAC CAGGACGACC TCAAGCACTG GCGCCGGCCC
                                                           SacI (1298)
1261 ATCACTCTCG GCATGCACGA GCTGTACAAG TAAGAGCTCG AGGACGGGAG AATTAATTAG TATTGTACAA
     TAGTGAGAGC CGTACGTGCT CGACATGTTC ATTCTCGAGC TCCTGCCCTC TTAATTAATC ATAACATGTT

1331 GAAGCCATTT TATCTCTAAA TTTACGAATT AAGATTTTAA ATTTTAAACA TAAAGATGAT GATACGTATA
     CTTCGGTAAA ATAGAGATTT AAATGCTTAA TTCTAAAATT TAAAATTTGT ATTTCTACTA CTATGCATAT

1401 TACACTTTTG TAAAATATTA TTCGGTGTCT ATAACGGAAC AAACGCTACT ATATATTATC ATAGACCTCT
     ATGTGAAAAC ATTTTATAAT AAGCCACAGA TATTGCCTTG TTTGCGATGA TATATAATAG TATCTGGAGA
                                                                        XhoI (1529)
1471 AACGGGATAT ATGAATAATGA TTTCAGATAC TATATTTGTT CCTGTAGATA ATAACTAACT CGAGCCCGCT
     TTGCCCTATA TACTTATACT AAAGTCTATG ATATAAACAA GGACATCTAT TATTGATTGA GCTCGGGCGA

1541 GGTACCCGGG CTAAAATTG AAAATAAATA CAAAGGTTCT TGAGGGTTGT GTTAAATTGA AAGCAGAAA
     CCATGGGCCC GATTTTAAC TTTTATTTAT GTTTCCAAGA ACTCCCAACA CAATTTAACT TTCGCTCTTT
       SmaI (1627)      SalI (1642)
                                  PstI (1652)
1611 TAATCATAAA TAAGCCCCGG GATCCTCTAG AGTCGACCTG CAGTCAAACT CTAATGACCA CATCTTTTT
     ATTAGTATTT ATTCGGGGCC CTAGGAGATC TCAGCTGGAC GTCAGTTTGA GATTACTGGT GTAGAAAAA
```

FIG. 8-3

1681  TACAGATGAA AAATTTTCCA CATCTCCTTT TGTAGACACG ACTAACATT TTCCAGAAAA AAGTTTATTA
      ATCTTACTT TTTAAAGGT GTAGAGGAAA ACATCTGTGC TGATTTGTAA AACGTCTTTT TTCAAATAAT

1751  GTGTTTAGAT AATCGTATAC TTCATCAGTG TAGATAGTAA ATGTGAACAG ATAAAAGGTA TTCTTGCTCA
      CACAAATCTA TTAGCATATG AAGTAGTCAC ATCTATCATT TACACTTGTC TATTTTCCAT AAGAACGAGT

1821  ATAGATTGGT AAATTCCCATA GAATATATTA ATCCTTTCTT CTTGAGATCC CACATCATTT CAACCAGAGA
      TATCTAACCA TTTAAGGTAT CTTATATAAT TAGGAAAGAA GAACTCTAGG GTGTAGTAAA GTTGGTCTCT

1891  CGTTTTATCC AATGATTTAC CTCGTACTAT ACCACATACA AAACTAGATT TTGCAGTGAC GTCGTATCTG
      GCAAAATAGG TTACTAAATG GAGCATGATA TGGTGTATGT TTTGATCTAA AACGTCACTG CAGCATAGAC

1961  GTATTCCTAC CAAACAAAAT TTTACTTTTA GTTCTTTTAG AAAATTCTAA GGTAGAATCT CTATTTGCCA
      CATAAGGATG GTTTGTTTTA AAATGAAAAT CAAGAAATC TTTTAAGATT CCATCTTAGA GATAAACGGT

2031  ATATGTCATC TATGGAATTA CCACTAGCAA AAAATGATAG AAATATATAT TGATACATCG CAGCTGGTTT
      TATACAGTAG ATACCTTAAT GGTGATCGTT TTTTACTATC TTTATATATA ACTATGTAGC GTCGACCAAA

2101  TGATTCACTA TACTTTAAAA ACGAATCAGA TTCCATAATT GCCTGTATAT CATCAGCTGA AAAACTATGT
      ACTAGATGAT ATGAAATTTT TGCTTAGTCT AAGGTATTAA CGGACATATA GTAGTCGACT TTTTGATACA

2171  TTTACACGTA TTCCTTCGGC ATTTCTTTTT AATGATATAT CTTGTTTAGA CAATGATAAA GTTATCATGT
      AAATGTGCAT AAGGAAGCCG TAAAGAAAAA TTACTATATA GAACAAATCT GTTACAAATCTT CAATAGTACA

FIG. 8-4

```
2241 CCATGAGAGA CCCGCTCCG  TATCGTATAA ATATTCATT  AGATGTTAGA CGGTTCATTA GGGGTATACT
     GGTACTCTCT GGCGAGAGC  ATAGCATATT TATAAAGTAA TCTACAATCT GCGAAGTAAT CCCCATATGA
                                                        HindIII (2356)
2311 TCTATAAGGT  TTCCTTAATCA GTCCATCATT GGTTGGGTCA AGAACAAGCT TGTCTCCCTA TAGTGACTCG
     AGATATTCCA  AAGRATTAGT CAGGTAGTAA CCAACCCAGT TCTTGTTCGA ACAGAGGGAT ATCACTGAGC 2381 TATTAGAGCT  TGGCGTAATC ATGGTCATAG CTGTTTCCTG TGTGAAATTG TTATCCGCTC ACAATTCCAC
     ATAATCTCGA  ACCGCATTAG TACCAGTATC GACAAAGGAC ACACTTTAAC AATAGGCGAG TGTTAAGGTG 2451 ACAACATACG  AGCCGGAAGC ATAAAGTGTA AAGCCTGGGG TGCCTAATGA GTGAGCTAAC TCACATTAAT
     TGTTGTATGC  TCGGCCTTCG TATTTCACAT TTCGGACCCC ACGGATTACT CACTCGATTG AGTGTAATTA 2521 TGGCTTCGGC  TCACTGCCCG CTTTCCAGTC GGGAAACCTG TCGTGCCAGC TGCATTAATG AATCGGCCAA
     ACGCAAGCCG  AGTGACGGGC GAAAGGTCAG CCCTTTGGAC AGCACGGTCG ACGTAATTAC TTAGCCGGTT 2591 CGCGCGGGGA  GAGGCGGTTT GCGTATTGGG CGCTCTTCCG CTTCCTCGCT CACTGACTCG CTGCGCTCGG
     GCGCGCCCCT  CTCCGCCAAA CGCATAACCC GCGAGAAGGC GAAGGAGCGA GTGACTGAGC GACGCGAGCC 2661 TCGTTCGGCT  GCGGCGAGCG GTATCAGCTC ACTCAAAGGC GGTAATACGG TTATCCACAG AATCAGGGGA
     AGCAAGCCGA  CGCCGCTCGC CATAGTCGAG TGAGTTTCCG CCATTATGCC AATAGGTGTC TTAGTCCCCT 2731 TAACGCAGGA  AAGAACATGT GAGCAAAAGG CCAGCAAAAG GCCAGGAACC GTAAAAAGGC CCGCGTTGCTG
     ATTGCGTCCT  TTCTTGTACA CTCGTTTTCC GGTCGTTTTC CGGTCCTTGG CATTTTTCCG GGCGAACGAC
```

FIG. 8-5

```
2801  GCGTTTTTCG ATAGGCTCCG CCCCCCTGAC GAGCATCACA AAAATCGACG CTCAAGTCAG AGGTGGCGAA
      CGCAAAAAGC TATCCGAGGC GGGGGGACTG CTCGTAGTGT TTTTAGCTGC GAGTTCAGTC TCCACCGCTT

2871  ACCCGACAGG ACTATAAGA TACCAGGCGT TTCCCCCTGG AAGCTCCCTC GTGCGCTCTC CTGTTCCGAC
      TGGGCTGTCC TGATATTTCT ATGGTCCGCA AAGGGGGACC TTCGAGGGAG CACGCGAGAG GACAAGGCTG

2941  CCTGCCGCTT ACCGGATACC TGTCCGCCTT TCTCCCTTCG GGAAGCGTGG CGCTTTCTCA TAGCTCACGC
      GGACGGCGAA TGGCCTATGG ACAGGCGGAA AGAGGGAAGC CCTTCGCACC GCGAAAGAGT ATCGAGTGCG

3011  TGTAGTGATC TCAGTTCGGT GTAGGTCGTT CGCTCCAAGC TGGGCTGTGT GCACGAACCC CCGTTCAGC
      ACATCACTAG AGTCAAGCCA CATCCAGCAA GCGAGGTTCG ACCCGACACA CGTGCTTGGG GGCAAGTCG

3081  CCGACCGCTG CGCCTTATCC GGTAACTATC GTCTTGAGTC CAACCCGGTA AGACACGACT TATCGCCACT
      GGCTGGCGAC GCGGAATAGG CCATTGATAG CAGAACTCAG GTTGGGCCAT TCTGTGCTGA ATAGCGGTGA

3151  GGCAGCAGCC ACTGGTAACA GGATTAGCAG AGCGAGGTAT GTAGGCGGTG CTACAGAGTT CTTGAAGTGG
      CCGTCGTCGG TGACCATTGT CCTAATCGTC TCGCTCCATA CATCCGCCAC GATGTCTCAA GAACTTCACC

3221  TGGCTAACT ACGGCTACAC TAGAAGGACA GTATTTGGTA TCTGCGCTCT GCTGAAGCCA GTTACCTTCG
      ACCGATTGA TGCCGATGTG ATCTTCCTGT CATAAACCAT AGACGCGAGA CGACTTCGGT CAATGGAAGC

3291  GAAAAGAGT TGGTAGCTCT TGATCCGGCA AACAAACCAC CGCTGGTAGC GGTGGTTTTT TTGTTTGCAA
      CTTTTTCTCA ACCATCGAGA ACTAGGCCGT TTGTTTGGTG GCGACCATCG CCACCAAAAA AACAAACGTT
```

FIG. 8-6

```
3361  GCAGCAGATT ACGGCAGAA AAAAGGATC TCAAGAAGAT CCTTGATCT TTTCTACGGG GTCTGACGCT
      CGTCGTCTAA TGCGCGTCTT TTTTTCCTAG AGTTCTTCTA GGAAACTAGA AAAGATGCCC CAGACTGCGA

3431  CAGTGGAACG AAAACTCACG TTAAGGGATT TGGTCATGA GATTATCAAA AAGGATTC ACCTAGATCC
      GTCACCTTGC TTTTGAGTGC AATTCCCTAA AACCAGTACT CTAATAGTTT TCCTAAGAAG TGGATCTAGG

3501  TTTTAAATTA AAAATGAAGT TTTAAATCAA TCTAAAGTAT ATATGAGTAA ACTGGTCTG ACAGTTACCA
      AAATTTAAT TTTACTTCA ARATTTAGTT AGATTTCATA TATACTCATT TGAACCAGAC TGTCAATGGT

3571  ATGCTTAATC AGTGAGGCAC CTATCTCAGC GATCTGTCTA TTTCGTTCAT CCATAGTTGC CTGACTCCCC
      TACGAATTAG TCACTCCGTG GATAGAGTCG CTAGACAGAT AAAGCAAGTA GGTATCAACG GACTGAGGGG

3641  GTCGTGTAGA TAACTACGAT ACGGGAGGGC TTACCATCTG GCCCCAGTGC TGCAATGATA CCGCGAGACC
      CAGCACATCT ATTGATGCTA TGCCCTCCCG AATGGTAGAC ACGTTACTAT GGCGGCTCTGG

3711  CACGCTCACC GGCTCCAGAT TTATCAGCAA TAAACCAGCC AGCCGGAAGG GCCGAGCGCA GAAGTGGTCC
      GTGCGAGTGG CCGAGGTCTA AATAGTCGTT ATTGGTCGG TCGGCCTTCC CGGCTCGCGT CTTCACCAGG

3781  TGCAACTTTA TCCGCCTCCA TCCAGTCTAT TAATTGTTGC CGGGAAGCTA GAGTAAGTAG TTCGCCAGTT
      ACGTTGCAAAT AGGCGGAGT AGGTCAGATA ATTAACAACG GCCCTTCGAT CTCATTCATC AAGCGGTCAA

3851  AATAGTTTGC GCAACGTTGT TGGCATTGCT ACAGGCATCG TGGTGTCACG CTCGTCGTTT GGTATGGCTT
      TTATCAAACG CGTTGCAACA ACCGTAACGA TGTCCGTAGC ACCACAGTGC GAGCAGGCAA CCATACCGAA
```

FIG. 8-7

3921 CATTCAGCTC CGGTTCCCAA CGATCAAGGC GAGTTACAAG ATCCCCCATG TTGTGCAAAA AAGCGGTAG
     GTAGTCGAG GCCAAGGGTT GCTAGTTCCG CTCAATGTAC TAGGGGGTAC AACACGTTTT TTCGCCAATC

3991 CTCCTTCGGT CCTCCGATCG TTGTCAGAAG TAAGTGGCC GCAGTGTTAT CACTCATGGT TATGCCAGCA
     GAGGAAGCCA GGAGGCTAGC AACAGTCTTC ATTCAACCGG CGTCACAATA GTGAGTACCA ATACGTCGT

4061 CTGCATAATT CTCTTACTGT CATGCCATCC GTAAGATGCT TTTCTGTGAC TGGTGAGTAC TCAACCAAGT
     GACGTATTAA GAGAATGACA GTACGGTAGG CATTCTACGA AAAGACACTG ACCACTCATG AGTTGGTTCA

4131 CATTCTGAGA ATAGTGTATG CGGGGACCGA GTTGCTCTG CCCGGCGTCA ATACGGGATA ATACCGCGC
     GTAAGACTCT TATCACATAC GCCCCTGGCT CAACGAGAAC GGGCCGCAGT TATGCCCTAT TATGGGCGG

4201 ACATAGCAGA ACTTTAAAAG TGCTCATCAT TGGAAAACGT TCTTCGGGGC GAAAACTCTC AAGGATCTTA
     TGTATCGTCT TGAAATTTTC ACGAGTAGTA ACCTTTTGCA AGAAGCCCCG CTTTTGAGAG TTCCTAGAAT

4271 CCGGCTGTTGA GATCCAGTTC GATGTAACCC ACTCGTGCAC CCAACTGATC TTCAGCATCT TTTACTTTCA
     GGCGACAACT CTAGGTCAAG CTACATTGGG TGAGCACGTG GGTTGACTAG AAGTCGTAGA AAATGAAAGT

4341 CCAGCGTTTC TGGGTGAGCA AAAACAGGAA GGCAAAATGC CGCAAAAAAG GGAATAAGGG CGACACGGAA
     GGTCGCAAAG ACCCACTCGT TTTTGTCCTT CCGTTTTACG GCGTTTTTTC CCTTATTCCC GCTGTGCCTT

4411 ATGTTGAATA CTCCATATCT TCCTTTTTCA ATATTATTGA AGCATTTATC AGGGTTATTG TCTCATGAGC
     TACAACTTAT GAGGTATAGA AGGAAAAAGT TATAATAACT TCGTAAATAG TCCCAATAAC AGAGTACTCG

FIG. 8-8

4481 GGATACATAT TTGAATGTAT TTAGAAAAAT AAACAAATAG GGGTTCCGCG CACATTTCCC CGAAAAGTGC
     CCTAGTATA AACTTACATA AATCTTTTTA TTTGTTTATC CCCAAGGCGC GTGTAAAGGG GCTTTTCACG

4551 CACCTGACGT CTAAGAAACC ATTATTATCA TGACATTAAC CTATAAAAAT AGGCGTATCA CGAGGCCCTT
     GTGGACTGCA GATTCTTTGG TAATAATAGT ACTGTAATTG GATATTTTTA TCCGCATAGT GCTCCGGGAA

4621 TGTTCTCGGG CGTTTCGGTG ATGACGGTGA AAACCTCTGA CACATGCAGC TCCCGGAGAC GGTCACAGCT
     ACAGAGAGCC GCAAAGCCAC TACTGCCACT TTTGGAGACT GTGTACGTCG AGGGCCTCTG CCAGTGTCGA

4691 TGTCTGTAAG CGGATGCCGG GAGCAGACAA GCCCGTCAGG GCCGGTCAGC GGGTGTTGCC GGGTGTCGGG
     ACAGACATTC GCCTACGGCC CTCGTCTGTT CGGGCAGTCG CGGCCAGTCG CCCACAACCG CCCACAGCCC

4761 GCTGGCTTAA CTATGCGGCA TCAGAGCAGA TTGTACTGAG AGTGCACCAT ATGCGGTGTG AAATACCGCA
     CGACCGAATT GATACGCCGT AGTCTCGTCT AACATGACTC TCACGTGGTA TACGCCACAC TTTATGGCGT

4831 CAGATGCGTA AGGAGAAAAT ACCGCATCAG GCGCCATTCG CCATTCAGGC TGCGCAACTG TTGGGAAGGG
     GTCTACGCAT TCCTCTTTTA TGGCGTAGTC CGCGGTAAGC GGTAAGTCCG ACGCGTTGAC AACCCTTCCC

4901 CGATCGGTGC GGGCCTCTTC GCTATTACGC CAGCTGGCGA AAGGGGGATG TGCTGCAAGG CGATTAAGTT
     GCTAGCCACG CCCGGAGAAG CGATAATGCG GTCGACCGCT TCCCCCCTAC ACGACGTTCC GCTAATTCAA

4971 GGGTAACGCC AGGGTTTTCC CAGTCACGAC GTTGTAAAAC GACGGCCAGT GAATTGGATT TAGGTGACAC
     CCCATTGCGG TCCCAAAAGG GTCAGTGCTG CAACATTTTG CTGCCGGTCA CTTAACCTAA ATCCACTGTG

5041 TATA
     ATAT

FIG. 8-9

```
ATGAGAGTGAGGGAGACAGTGAGGAATTATCAGCACTTGTGGAGATGGGGCATCATGCTCC
TTGGGATGTTAATGATATGTAGTGCTGCAGACCAGCTGTGGGTCACAGTGTATTATGGGGT
ACCTGTGTGGAAAGAAGCAACCACTACTCTATTTTGTGCATCAGATGCTAAAGCACATAAA
GCAGAGGCACATAATATCTGGGCTACACATGCCTGTGTACCAACAGACCCCAATCCACGAG
AAATAATACTAGGAAATGTCACAGAAAACTTTAACATGTGGAAGAATAACATGGTAGAGCA
GATGCATGAGGATATAATCAGTTTATGGATCAAAGTCTAAAACCATGTGTAAAATTAACC
CCACTCTGTGTTACTTTAAACTGCACTACATATTGGAATGGAACTTTACAGGGGAATGAAA
CTAAAGGGAAGAATAGAAGTGACATAATGACATGCTCTTTCAATATAACCACAGAAATAAG
AGGTAGAAAGAAGCAAGAAACTGCACTTTTCTATAAACTTGATGTGGTACCACTAGAGGAT
AAGGATAGTAATAAGACTACCAACTATAGCAGCTATAGATTAATAAATTGCAATACCTCAG
TCGTGACACAGGCGTGTCCAAAAGTAACCTTTGAGCCAATTCCCATACATTATTGTGCCCC
AGCTGGATTTGCGATTCTGAAATGTAATAATAAGACGTTCAATGGAACGGGTCCATGCAAA
AATGTCAGCACAGTACAGTGTACACATGGAATTAGGCCAGTAGTGTCAACTCAACTGTTGT
TGAATGGCAGTCTAGCAGAAGAAGAGATAATAATTAGATCTGAAAATATCACAAATAATGC
AAAAACCATAATAGTACAGCTTAATGAGTCTGTAACAATTGATTGCATAAGGCCCAACAAC
AATACAAGAAAAAGTATACGCATAGGACCAGGGCAAGCACTCTATACAACAGACATAATAG
GGAATATAAGACAAGCACATTGTAATGTTAGTAAAGTAAAATGGGGAAGAATGTTAAAAAG
GGTAGCTGAAAAATTAAAAGACCTTCTTAACCAGACAAAGAACATAACTTTTGAACCATCC
TCAGGAGGGGACCCAGAAATTACAACACACAGCTTTAATTGTGGAGGGGAATTCTTCTACT
GCAATACATCAGGACTATTTAATGGGAGTCTGCTTAATGAGCAGTTTAATGAGACATCAAA
TGATACTCTCACACTCCAATGCAGAATAAAACAAATTATAAACATGTGGCAAGGAGTAGGA
AAAGCAATGTATGCCCCTCCCATTGCAGGACCAATCAGCTGTTCATCAAATATTACAGGAC
TATTGTTGACAAGAGATGGTGGTAATACTGGTAATGATTCAGAGATCTTCAGACCTGGAGG
GGGAGATATGAGAGACAATTGGAGAAGTGAATTATACAAATATAAAGTAGTAAGAATTGAA
CCAATGGGTCTAGCACCCACCAGGGCAAAAAGAAGAGTGGTGGAAAGAGAAAAAAGAGCAA
TAGGACTGGGAGCTATGTTCCTTGGGTTCTTGGGAGCGGCAGGAAGCACGATGGGCGCAGC
GTCACTGACGCTGACGGTACAGGCCAGACAGTTATTGTCTGGTATAGTGCAACAGCAAAAC
AATTTGCTGAGAGCTATAGAGGCGCAACAGCATCTGTTGCAACTCACAGTCTGGGGCATTA
AACAGCTCCAGGCAAGAGTCCTGGCTATGGAAAGCTACCTAAAGGATCAACAGCTCCTAGG
AATTTGGGGTTGCTCTGGAAAACACATTTGCACCACTACTGTGCCCTGGAACTCTACCTGG
AGTAATAGATCTGTAGAGGAGATTTGGAATAATATGACCTGGATGCAGTGGGAAAGAGAAA
TTGAGAATTACACAGGTTTAATATACACCTTAATTGAAGAATCGCAAACCCAGCAAGAAAA
GAATGAACAAGAACTATTGCAATTGGATAAATGGGCAAGTTTGTGGAATTGGTTTAGTATA
ACAAAATGGCTGTGGTATATAAAATATTCATAATGATAGTAGGAGGCTTAATAGGTTTAA
GAATAGTTTTTGCTGTGCTTTCTTTAGTAAATAGAGTTAGGCAGGGATATTCACCTCTGTC
TTTTCAGACCCTCCTCCCAGCCCCGAGGGGACCCGACAGGCCCGAAGGAATAGAAGAAGAA
GGTGGAGAGCAAGGCTAA
```

Fig. 9

ATGGGTGCGAGAGCGTCAGTATTAAGCGGAGGAAAATTAGATGAATGGGAAAAAATT
CGGTTACGGCCAGGAGGAAACAAAAAATATAGATTAAAACATTTAGTATGGGCAAGC
AGGGAGCTAGAACGATTTGCACTTAATCCTGGTCTTTTAGAAACATCAGAAGGCTGT
AGACAAATAATAGAACAGCTACAACCATCTATTCAGACAGGATCAGAGGAACTTAAA
TCATTACATAATACAGTAGTAACCCTCTATTGTGTACATGAAAGGATAAAGGTAGCA
GATACCAAGGAAGCTTTAGATAAGATAAAGGAAGAACAAACCAAAAGTAAGAAAAAA
GCACAGCAAGCAACAGCTGACAGCAGCCAGGTCAGCCAAAATTATCCTATAGTACAA
AACCTACAGGGACAAATGGTACACCAGTCCTTATCACCTAGGACTTTGAATGCATGG
GTAAAAGTAATAGAAGAGAAGGCTTTCAGCCCAGAAGTAATACCCATGTTTTCAGCA
TTATCAGAAGGAGCCACACCAACAGATTTAAACACCATGCTAAACACAGTAGGAGGA
CATCAAGCAGCCATGCAAATGTTAAAAGAGACTATCAATGAGGAAGCTGCAGAATGG
GATAGGCTACATCCAGTGCCTGCAGGGCCTGTTGCACCAGGCCAAATGAGAGAACCA
AGAGGAAGTGATATAGCAGGAACTACCAGTACCCTTCAGGAACAAAGAAATCTATAA
AAGATGGATAATCCTAGGATTAAATAAAATAGTAAGAATGTATAGCCCTGTCAGCAT
TTTGGACATAAGACAAGGACCAAAGGAACCCTTTAGAGACTATGTAGATCGGTTCTA
TAAAACTCTACGAGCCGAGCAAGCTTCACAGGATGTAAAAAATTGGATGACTGAAAC
CTTGTTAGTCCAAAATGCGAATCCAGATTGTAAAACTATCTTAAAAGCATTGGGACC
AGCGGCTACATTAGAAGAAATGATGACAGCATGTCAGGGAGTGGGGGGACCCAGTCA
TAAAGCAAGAGTTTTGGCTGAGGCAATGAGCCAAGCATCAAACACAAATGCTGTTAT
AATGATGCAGAGGGGCAATTTCAAGGGCAAGAAAATCATTAAGTGTTTCAACTGTGG
CAAAGAAGGACACCTAGCAAAAAATTGTAGGGCTCCTAGGAAAAGAGGCTGTTGGAA
ATGTGGAAAGGAAGGGCACCAAATGAAAGATTGTAATGAAAGACAGGCTAATTTTTT
AGGGAGAATTTGGCCTTCCCACAAGGGGAGGCCAGGGAATTTCCTTCAGAGCAGACC
AGAGCCAACAGCCCCACCAGCAGAGAGCTTCGGGTTTGGGGAAGAGATAACACCCTC
CCAGAAACAGGAGGGGAAAGAGGAGCTGTATCCTTCAGCCTCCCTCAAATCACTCTT
TGGCAACGACCCCTAGTCACAATAAAAATAGGGGGACAGCTAAAGGAAGCTCTATTA
GATACAGGAGCAGATGATACAGTAGTAGAAGAAATGAATTTGCCAGGAAAATGGAAA
CCAAAAATGATAGGGGGAATTGGGGGCTTTATCAAAGTAAGACAGTATGATCAAATA
CTCGTAGAAATCTATGGATATAAGGCTACAGGTACAGTATTAGTAGGACCTACACCT
GTCAACATAATTGGAAGAAATTTGTTGACTCAGATTGGTTGCACTTTAAATTTTCCA
ATTAGTCCTATTGAAACTGTACCAGTAAAATTAAAGTCAGGGATGGATGGTCCAAGA
GTTAAACAATGGCCATTGACAGAAGAGAAAATAAAAGCACTAATAGAAATTTGTACA
GAAATGGAAAAGGAAGGAAAACTTTCAAGAATTGGACCTGAAAATCCATACAATACT
CCAATATTTGCCATAAAGAAAAAGACAGTACTAAGTGGAGAAAATTAGTAGATTTC
AGAGAACTTAATAAGAGAACTCAAGATTTCTGGGAAGTTCAACTAGGAATACCACAT
CCTGCAGGGCTAAAAAAGAAAAAATCAGTAACAGTACTGGAGGTGGGTGATGCATAT
TTTTCAGTTCCCTTATATGAAGACTTTAGAAAATACACTGCATTCACCATACCTAGT
ATAAACAATGAGACACCAGGAATTAGATATCAGTACAATGTGCTTCCACAAGGATGG
AAAGGATCACCGGCAATATTCCAAAGTAGCATGACAAAAATTTTAGAACCTTTTAGA
AAACAAAATCCAGAAGTGGTTATCTACCAATACATGCACGATTTGTATGTAGGATCT
GACTTA

```
GAAATAGGGCAGCATAGAATAAAAATAGAGGAATTAAGGGGACACCTATTGAAGTGGG
GATTTACCACACCAGACAAAAATCATCAGAAGGAACCTCCATTTCTTTGGATGGGTTA
TGAACTCCATCCTGATAAATGGACAGTACAGCCTATAAAACTGCCAGAAAAAGAAAGC
TGGACTGTCAATGATCTGCAGAAGTTAGTGGGGAAATTAAATTGGGCAAGTCAAATTT
ATTCAGGAATTAAAGTAAGACAATTATGCAAATGCCTTAGGGGAACCAAAGCACTGAC
AGAAGTAGTACCACTGACAGAAGAAGCAGAATTAGAACTGGCAGAAAACAGGGAACTT
CTAAAAGAAACAGTACATGGAGTGTATTATGACCCATCAAAAGACTTAATAGCAGAAA
TACAGAAACAAGGGCAAGACCAATGGACATATCAAATTTATCAAGAACAATATAAAAA
TTTGAAAACAGGAAAGTATGCAAAGAGGAGGAGTACCCACACTAATGATGTAAAACAA
TTAACAGAGGCAGTGCAAAAAATAGCCCAAGAATGTATAGTGATATGGGGAAAGACTC
CTAAATTCAGACTACCCATACAAAAGGAAACATGGGAAACATGGTGGACAGAGTATTG
GCAGGCCACCTGGATTCCTGAGTGGGAGTTTGTCAATACCCCTCCCTTGGTTAAATTA
TGGTACCAGTTAGAGAAGGAACCCATAGTAGGAGCAGAAACCTTCTAA
```

Fig. 10-2

A
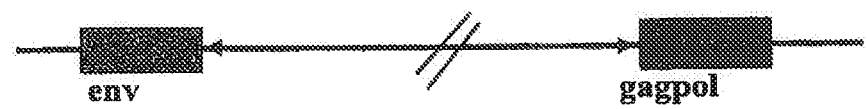
B
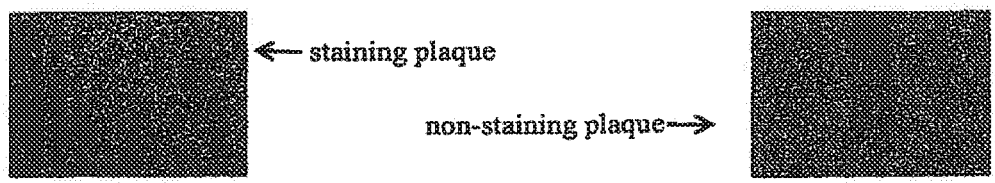
Fig. 11

INTERGENIC SITES BETWEEN CONSERVED GENES IN THE GENOME OF MODIFIED VACCINIA ANKARA (MVA) VACCINIA VIRUS

CROSS-REFERENCE TO RELATED APPLICATIONS

This application is a divisional of U.S. patent application Ser. No. 12/377,847, filed Feb. 17, 2010; which claims the benefit and priority to, and is a U.S. National Phase of International Patent Application No. PCT/IB2007/004575, filed on Aug. 24, 2007, designating the United States of America and published in the English language; which is an International application of and claims the benefit of priority to U.S. Provisional Patent Application Ser. No. 60/840,093, filed Aug. 25, 2006, and U.S. Provisional Patent Application Ser. No. 60/840,755, filed Aug. 28, 2006; the disclosures of all the foregoing being hereby expressly incorporated by reference in their entireties.

FIELD OF THE INVENTION

The present invention relates to insertion sites useful for the stable integration of exogenous DNA sequences into the MVA genome.

DESCRIPTION OF THE RELATED ART

The members of the poxvirus family have large double-stranded DNA genomes encoding several hundred proteins (Moss, B. 2007 "Poxviridae: The Viruses and Their Replication" in *Fields Virology*, 5$^{th}$ Ed. (D. M. Knipe, P. M. Howley, D. E. Griffin, R. A. Lamb, M. A. Martin, B. Roizman, and S. E. Straus, Eds), Lippincott Williams & Wilkins, Philadelphia, Pa.). The genomic sequence of the highly attenuated vaccinia strain modified vaccinia Ankara (MVA) (Mayr, A. et al. 1978 *Zentralbl Bakteriol* 167:375-390), which cannot grow in most mammalian cells and which is a good candidate for a recombinant vaccine vector, is known (Sutter, G. and Moss, B. 1992 *Proc Natl Acad Sci USA* 89:10847-10851; and Sutter, G. et al. 1994 *Vaccine* 12:1032-1040) has been passaged over 570 times in chicken embryo fibroblasts, during which six major deletions relative to the parental wild-type strain Ankara, accompanied by a severe restriction in host range, have occurred (Meyer, H. et al. 1991 *J Gen Virol* 72:1031-1038).

SUMMARY OF THE INVENTION

The present invention relates to new insertion sites useful for the integration of exogenous sequences into an intergenic region (IGR) of a vaccinia virus genome, where the IGR is located between or is flanked by two adjacent open reading frames (ORFs) of the vaccinia virus genome, and where the ORFs correspond to conserved genes, and to related plasmid vectors useful to insert exogenous DNA into the genome of a vaccinia virus, and further to recombinant vaccinia viruses comprising an exogenous sequence inserted into said new insertion site as a medicine or vaccine.

BRIEF DESCRIPTION OF THE DRAWINGS

FIG. 3. Tropic and biologic properties of HIV-1 isolates.

FIG. 8-1 through FIG. 8-9. Nucleotide sequence of the pLW-73 transfer vector (top strand, SEQ ID NO: 2; bottom strand, SEQ ID NO: 3).

FIG. 9. Nucleotide sequence encoding Ugandan clade D Env protein (isolate AO7412) (SEQ ID NO: 4).

FIG. 10-1 through FIG. 10-2. Codon altered nucleotide sequence encoding Ugandan clade D gagpol protein (isolate AO3349) (SEQ ID NO: 5).

FIG. 11. Generation of recombinant MVAs and analysis of stability of inserted genes. A) Schematic diagram of insertion of env and gagpol into Del II and Del III sites, respectively. B) Evaluation of stability by immunostaining.

DEPOSIT OF MICROORGANISM

Figure 1:
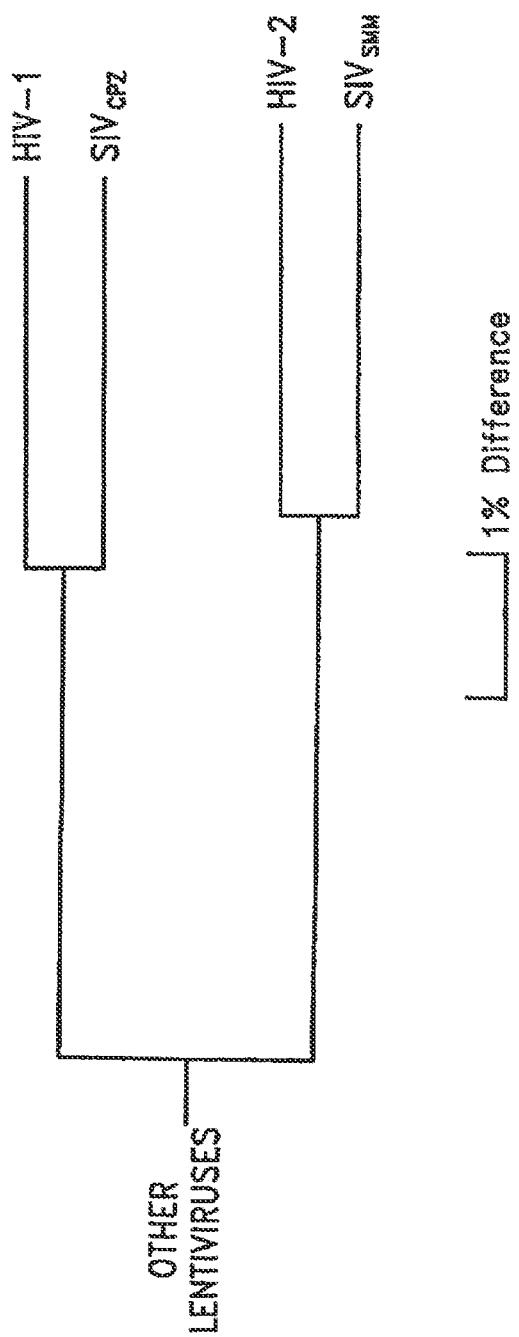
FIG. 1. Phylogenetic relationships of HIV-1 and HIV-2 based on identity of pol gene sequences. SIV$_{cpz}$ and SIV$_{smm}$ are subhuman primate lentiviruses recovered from a chimpanzee and sooty mangabey monkey, respectively.

The following microorganism has been deposited in accordance with the terms of the Budapest Treaty with the American Type Culture Collection (ATCC), Manassas, Va., on the date indicated:

| Microorganism | Accession No. | Date |
|---|---|---|
| MVA 1974/NIH Clone 1 | PTA-5095 | Mar. 27, 2003 |

MVA 1974/NIH Clone 1 was deposited as ATCC Accession No.: PTA-5095 on Mar. 27, 2003 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology*, 3rd ed., J. Wiley & Sons, Chichester, N.Y., 2001 and *Fields Virology*, 5th Ed. (D. M. Knipe, P. M. Howley, D. E. Griffin, R. A. Lamb, M. A. Martin, B. Roizman, and S. E. Straus, eds), Lippincott Williams & Wilkins, Philadelphia, Pa., 2007.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

Poxviruses are divided into the subfamilies Chordopoxvirinae and Entomopoxvirinae, based on vertebrate and insect host range. The subfamily Chordopoxvirinae consists of eight genera: *Orthopoxvirus, Parapaxvirus, Avipoxvirus, Capripoxvirus, Leporipoxvirus, Suipoxvirus, Molluscipoxvirus*, and *Yatapoxvirus*. The prototypal member of the genus *Orthopoxvirus* is vaccinia virus.

Complete genome sequences have been reported for at least one member of each chordopoxvirus genus and two entomopoxviruses. Nearly 100 genes are conserved in all chordopoxviruses, and about half of these are also present in entomopoxviruses. Based on the above, several generalizations can be made: Genes are largely nonoverlapping, tend to occur in blocks pointing toward the nearer end of the genome, are usually located in the central region if highly conserved and concerned with essential replication functions, and are usually located in the end regions if variable and concerned with host interactions. The arrangement of the central genes is remarkably similar in all chordopoxviruses. A convention for naming vaccinia virus genes or ORFs (open reading frames), originating prior to sequencing the entire genome and subsequently used for the complete sequence of the Copenhagen strain of vaccinia virus, consists of using the HindIII restriction endonuclease DNA fragment letter, followed by the ORF number (from left to right) within the fragment, and L or R, depending on the direction of the ORF. An exception to this rule was made for the HindIII C fragment; the ORFs were numbered from the right in order to avoid starting at the highly variable left end of the genome. Polypeptide names correspond to gene names, except that L or R is dropped. In most subsequent complete poxvirus genome sequences, ORFs were numbered successively from one end of the genome to the other. Nevertheless, the old letter designations have been retained as common names to provide continuity in the literature. The ORF number of the Western Reserve (WR) strain of vaccinia virus is commonly shown in reference books because this strain has been used for the great majority of biochemical and genetic studies.

The inventors of an embodiment of the present invention identified new sites for the insertion of exogenous DNA sequences into the genome of modified vaccinia Ankara (MVA) virus. The new insertion sites are located in the intergenic regions (IGRs) of the viral genome, wherein the IGRs are, in turn, located between or are flanked by two adjacent open reading frames (ORFs) of the MVA genome, and wherein the ORFs correspond to conserved genes.

Accordingly, an embodiment of the invention relates to a recombinant MVA comprising a heterologous DNA sequence inserted into an IGR of the viral genome. According to the present embodiment, one or more exogenous DNA sequences may be inserted into one or more IGRs.

It was surprisingly found that exogenous DNA sequences remain stable inserted into IGRs of the MVA genome. The genome of MVA is to be considered as being quite unstable. It seems that genes or DNA sequences non-essential for propagation of the virus are deleted or fragmented. Although it was—on the one hand—found that stable recombinant MVAs are obtained when heterologous DNA sequences are inserted into the naturally occurring deletion sites of the MVA genome, it was—on the other hand—found that sometimes these recombinant MVAs are unstable. Therefore, it could be concluded that inserting heterologous DNA sequences non-essential for viral propagation into spaces between ORFs would be expected to be deleted by the virus as well.

While the nucleotide sequence of an ORF encodes an amino acid sequence forming a peptide, polypeptide or protein, the IGRs between two ORFs have no coding capacity, but may comprise regulatory elements, binding sites, promoter and/or enhancer sequences essential for or involved in the transcriptional control of the viral gene expression. Thus, the IGR may be involved in the regulatory control of the viral life cycle. However, the inventors of the present embodiment have also shown that the new insertion sites have the unexpected advantage that exogenous DNA sequences can be stably inserted into the MVA genome without influencing or changing the typical characteristics and gene expression of MVA. The new insertion sites are especially useful, since no ORF or coding sequence of MVA is altered.

The nucleotide sequence of an ORF regularly starts with a start codon and ends with a stop codon. Depending on the orientation of the two adjacent ORFs the IGR, the region in between these ORFs, is flanked either by the two stop codons of the two adjacent ORFs, or, by the two start codons of the two adjacent ORFs, or, by the stop codon of the first ORF and the start codon of the second ORF, or, by the start codon of the first ORF and the stop codon of the second ORF.

Accordingly, the insertion site for the exogenous DNA sequence into the IGR may be downstream or 3' of the stop codon of a first ORF. In case the adjacent ORF, also termed second ORF, has the same orientation as the first ORF, this insertion site downstream of the stop codon of the first ORF lies upstream or 5' of the start codon of the second ORF.

In case the second ORF has an opposite orientation relative to the first ORF, which means the orientation of the two adjacent ORFs points to each other, then the insertion site lies downstream of the stop codons of both ORFs.

As a third alternative, in case the two adjacent ORFs read in opposite directions, but the orientation of the two adjacent ORFs points away from each other, which is synonymous with a positioning that is characterized in that the start codons of the two ORFs are adjacent to each other, then the exogenous DNA is inserted upstream relative to both start codons.

ORFs in the MVA genome occur in two coding directions. Consequently, mRNA synthesis activity occurs from left to right, i.e., forward direction and, correspondingly, from right to left (reverse direction). It is common practice in poxvirology and it became a standard classification for vaccinia viruses to identify ORFs by their orientation and their position on the different HindIII restriction digest fragments of the genome. For the nomenclature, the different HindIII fragments are named by descending capital letters corresponding with their descending size. The ORF are numbered from left to right on each HindIII fragment and the orientation of the ORF is indicated by a capital L (standing for transcription from right to Left) or R (standing for transcription from left to Right). Additionally, there is a more recent publication of the MVA genome structure, which uses a different nomenclature, simply numbering the ORF from the left to the right end of the genome and indicating their orientation with a capital L or R (Antoine, G. et al. 1998 *Virology* 244:365-396). As an example the I8R ORF, according to the old nomenclature, corresponds to the 069R ORF according to Antoine et al.

In their efforts to make recombinants of modified vaccinia virus Ankara (MVA) expressing HIV genes as candidate vaccines, the inventors have observed instability in the expression of the HIV genes. They have determined that one of the causes of instability is due to deletions of the foreign gene and flanking MVA. To overcome this problem they set out to insert foreign genes between conserved genes in order to prevent viable deletions from occurring in recombinant MVAs. Viruses with such deletions have a growth advantage and will thus overgrow rMVA virus populations. If one inserts foreign genes between conserved genes in the vaccinia genome (these genes are considered to be required for vaccinia virus replication and are therefore "essential genes"), any deletion of an essential gene would inhibit virus replication, and, therefore, not overgrow the recombinant MVAs. Thus, the stable expression of the rMVA population is maintained. The strain of MVA that the inventors have been using to make their recombinants was provided by them to the Centers for Disease Control and Prevention (CDC) and was subsequently sequenced by Acambis (Genbank Accession number AY603355). The strain of MVA that Bavarian Nordic has based their WO03/097845 publication on is vaccinia virus strain modified vaccinia Ankara (Genbank Accession number U94848) sequenced by Antoine, G. et al. 1998 *Virology* 244:365-396. (Please note that the gene numbers in these two sequences for a given gene are different.)

The inventors initially looked at genes conserved in the Poxviridae family as well as those genes conserved in subfamily Chordopoxvirinae (the vertebrate poxviruses) (Upton, C. et al. 2003 *Journal of Virology* 77:7590-7600). These genes are listed in the nomenclature of Copenhagen vaccinia virus (Genbank Accession number M35027) given on the Poxvirus Bioinformatics Resource Center found on the world wide web at poxvirus.org. These genes total 49 conserved genes in the Poxvirus family and 41 additional genes conserved in chordopoxviruses, making a total of 90 conserved genes. From these 90 conserved genes, the inventors listed intergenic sites between conserved gene pairs. These gene pairs are listed in Table 1. (Please note that genes are marked that have not been included in the Bavarian Nordic WO03/097845 publication). The orientations of these genes are variable, with some being transcribed to the right, some to the left. This means that some of the intergenic sites contain promoters that would have to be preserved in the construction of the insertion vector. In addition, for overlapping conserved genes, during vector construction the genes would have to be reconstructed using alternative codons to minimize the repeating sequences.

In a preferred embodiment, the inventors focused on conserved genes whose orientation is "end to end" such that the 3' stop codon of the genes are in close proximity to one another. The construction of transfer vectors used in these sites are facilitated by the fact that there would be no promoter in this region between the stop codons. If there are intergenic nucleotides separating the stop codons, then construction of the insertion vector is straightforward. If the stop codon of one gene is within the 3' end of the other gene, then during construction of the plasmid transfer vector, the gene can be reconstructed using alternative codons to minimize repeating sequences, or, depending on the size of the overlap, simply corrected in the PCR of the flanks so as not to overlap. Table 2 gives the intergenic sites that meet the requirement of the orientation of the conserved genes being "end to end". Those intergenic sites in bolded text have no overlapping ends and therefore are simplest to construct.

The inventors specifically focused on the six intergenic sites that have no overlapping ends. In a working example, of these six, they chose the intergenic site, 071-072 (I8R-G1L), to insert their foreign gene.

Besides using the requirement of conserved genes as listed above in the Upton publication, for any gene that has been experimentally deleted and virus replication is reduced by 10 fold in the mutant, this gene could be considered as an "essential gene". If this gene lies adjacent to another essential or conserved gene, the intergenic site between the two genes could be considered as a different site of insertion for a foreign gene.

TABLE 1

Intergenic Sites between Conserved Genes

| Genes/ Copenhagen | CDC/Acambis Genes | Antoine et al. Genes | Listed in WO03/097845 publ ? N = No |
|---|---|---|---|
| F9L-F10L | 040-041 | 038L-039L | |
| F12L-F13L | 044-045 | 042L-043L | N |
| F17R-E1L | 049-050 | 047R-048L | N |
| E1L-E2L | 050-051 | 048L-049L | N |
| E8R-E9L | 057-058 | 055R-056L | |
| E9L-E10R | 058-059 | 056L-057L | N |
| I1L-I2L | 064-065 | 062L-063L | N |
| I2L-I3L | 065-066 | 063L-064L | N |
| I5L-I6L | 068-069 | 066L-067L | |
| I6L-I7L | 069-070 | 067L-068L | N |
| I7L-I8R | 070-071 | 068L-069R | N |
| I8R-G1L | 071-072 | 069R-070L | N |
| G1L-G3L | 072-073 | 070L-071L | N |
| G3L-G2R | 073-074 | 071L-072R | N |
| G2R-G4L | 074-075 | 072R-073L | N |
| G4L-G5R | 075-076 | 073L-074R | N |
| G5R-G5.5R | 076-077 | 074R-075R | N |
| G5.5R-G6R | 077-078 | 075R-076R | N |
| G6R-G7L | 078-079 | 076R-077L | N |
| G7L-G8R | 079-080 | 077L-078R | |
| G8R-G9R | 080-081 | 078R-079R | |
| G9R-L1R | 081-082 | 079R-080R | N |
| L1R-L2R | 082-083 | 080R-081R | |
| L2R-L3L | 083-084 | 081R-082L | |
| L3L-L4R | 084-085 | 082L-083R | |
| L4R-L5R | 085-086 | 083R-084R | N |
| L5R-J1R | 086-087 | 084R-085R | N |
| J3R-J4R | 089-090 | 087R-088R | N |
| J4R-J5L | 090-091 | 088R-089L | |
| J5L-J6R | 091-092 | 089L-090R | |
| J6R-H1L | 092-093 | 090R-091L | N |
| H1L-H2R | 093-094 | 091L-092R | N |
| H2R-H3L | 094-095 | 092R-093L | |
| H3L-H4L | 095-096 | 093L-094L | N |
| H4L-H5R | 096-097 | 094L-095R | |
| H5R-H6R | 097-098 | 095R-096R | N |
| H6R-H7R | 098-099 | 096R-097R | |
| H7R-D1R | 099-100 | 097R-098R | |
| D1R-D2L | 100-101 | 098R-099L | N |
| D2L-D3R | 101-102 | 099L-100R | N |
| D3R-D4R | 102-103 | 100R-101R | N |
| D4R-D5R | 103-104 | 101R-102R | |
| D5R-D6R | 104-105 | 102R-103R | N |
| D6R-D7R | 105-106 | 103R-104R | |
| D9R-D10R | 108-109 | 106R-107R | N |
| D10R-D11L | 109-110 | 107R-108L | |
| D11L-D12L | 110-111 | 108L-109L | |
| D12L-D13L | 111-112 | 109L-110L | |
| D13L-A1L | 112-113 | 110L-111L | |
| A1L-A2L | 113-114 | 111L-112L | N |
| A2L-A2.5L | 114-115 | 112L-113L | N |
| A2.5L-A3L | 115-116 | 113L-114L | |
| A3L-A4L | 116-117 | 114L-115L | |
| A4L-A5R | 117-118 | 115L-116R | |
| A5R-A6L | 118-119 | 116R-117L | N |
| A6L-A7L | 119-120 | 117L-118L | |
| A7L-A8R | 120-121 | 118L-119R | |
| A8R-A9L | 121-122 | 119R-120L | N |
| A9L-A10L | 122-123 | 120L-121L | N |
| A10L-A11R | 123-124 | 121L-122R | N |
| A11R-A12L | 124-125 | 122R-123L | |
| A12L-A13L | 125-126 | 123L-124L | |
| A13L-A14L | 126-127 | 124L-125L | |
| A14L-A14.5L | 127-128 | 125L-125.5L | N |
| A14.5L-A15L | 128-129 | 125.5L-126L | N |
| A15L-A16L | 129-130 | 126L-127L | N |
| A16L-A17L | 130-131 | 127L-128L | N |
| A17L-A18R | 131-132 | 128L-129R | N |
| A18R-A19L | 132-133 | 129R-130L | N |
| A19L-A21L | 133-134 | 130L-131L | N |
| A21L-A20R | 134-135 | 131L-132R | N |
| A20R-A22R | 135-136 | 132R-133R | N |
| A22R-A23R | 136-137 | 133R-134R | |
| A23R-A24R | 137-138 | 134R-135R | |

TABLE 1-continued

Intergenic Sites between Conserved Genes

| Genes/ Copenhagen | CDC/Acambis Genes | Antoine et al. Genes | Listed in WO03/097845 publ ? N = No |
|---|---|---|---|
| A28L-A29L | 141-142 | 139L-140L | N |
| A29L-A30L | 142-143 | 140L-141L | N |

TABLE 2

Conserved genes with "end to end" orientation

| Genes end to end | Overlapping ends | CDC/Acambis genes | Antoine genes |
|---|---|---|---|
| F17R-E1L | Yes | 049-050 | 047R-048L |
| E8R-E9L | No | 057-058 | 055R-056L |
| I8R-G1L | No | 071-072 | 069R-070L |
| G2R-G4L | Yes | 074-075 | 072R-073L |
| G6R-G7L | Yes | 078-079 | 076R-077L |
| L2R-L3L | Yes | 083-084 | 081R-082L |
| J4R-J5L | No | 090-091 | 088R-089L |
| J6R-H1L | Yes | 092-093 | 090R-091L |
| H2R-H3L | No | 094-095 | 092R-093L |
| D1R-D2L | Yes | 100-101 | 098R-099L |
| D10R-D11L | No | 109-110 | 107R-108L |
| A5R-A6L | Yes | 118-119 | 116R-117L |
| A8R-A9L | Yes | 121-122 | 119R-120L |
| A11R-A12L | No | 124-125 | 122R-123L |
| A18R-A19L | Yes | 132-133 | 129R-130L |

Genes in bolded text have no overlapping ends and thus are simplest to use as intergenic sites.

According to the present invention, heterologous DNA sequences can be inserted into one or more IGRs in between two adjacent ORFs selected from the group consisting of (using the nomenclature according to CDC/Acambis):

044-045, 049-050, 050-051, 058-059, 064-065, 065-066, 069-070, 070-071, 071-072, 072-073, 073-074, 074-075, 075-076, 076-077, 077-078, 078-079, 081-082, 085-086, 086-087, 089-090, 092-093, 093-094, 095-096, 097-098, 100-101, 101-102, 102-103, 104-105, 108-109, 113-114, 114-115, 118-119, 121-122, 122-123, 123-124, 127-128, 128-129, 129-130, 130-131, 131-132, 132-133, 133-134, 134-135, 135-136, 141-142, and 142-143, in an exemplary manner or corresponding thereto in other strains of vaccinia virus.

In a preferred embodiment, the heterologous sequence is inserted into an IGR flanked by two adjacent ORFs with "end to end" orientation selected from the group consisting of 049-050, 071-072, 074-075, 078-079, 092-093, 100-101, 118-119, 121-122, and 132-133.

In a working example, the heterologous DNA sequence is inserted into an IGR in which the conserved genes have no overlapping ends 071-072.

Heterologous or exogenous DNA sequences are sequences which, in nature, are not normally found associated with the poxvirus as used according to the present invention. According to a further embodiment of the present invention, the exogenous DNA sequence comprises at least one coding sequence. The coding sequence is operatively linked to a transcription control element, preferably to a poxviral transcription control element. Additionally, also combinations between poxviral transcription control element and, e.g., internal ribosomal entry sites can be used.

According to a further embodiment, the exogenous DNA sequence can also comprise two or more coding sequences linked to one or several transcription control elements.

Preferably, the coding sequence encodes one or more proteins, polypeptides, peptides, foreign antigens or antigenic epitopes, especially those of therapeutically interesting genes.

Therapeutically interesting genes according to the present invention may be genes derived from or homologous to genes of pathogenous or infectious microorganisms which are disease causing. Accordingly, in the context of the present invention such therapeutically interesting genes are presented to the immune system of an organism in order to affect, preferably induce a specific immune response and, thereby, vaccinate or prophylactically protect the organism against an infection with the microorganism. In further preferred embodiments of the present invention the therapeutically interesting genes are selected from genes of infectious viruses, e.g.,—but not limited to—dengue virus, hepatitis virus B or C, or human immunodeficiency viruses such as HIV.

According to a preferred embodiment of the present invention the heterologous DNA sequence is derived from HIV and encodes HIV env, wherein the HIV env gene is preferably inserted into the IGR between the ORFs 071-072 (I8R-G1L).

Furthermore, therapeutically interesting genes according to the present invention also comprise disease related genes, which have a therapeutic effect on proliferative disorder, cancer or metabolic diseases. For example, a therapeutically interesting gene regarding cancer could be a cancer antigen that has the capacity to induce a specific anti-cancer immune reaction.

According to a further embodiment of the present invention, the coding sequence comprises at least one marker or selection gene.

Selection genes transduce a particular resistance to a cell, whereby a certain selection method becomes possible. The skilled practitioner is familiar with a variety of selection genes, which can be used in a poxviral system. Among these are, e.g., neomycin resistance gene (NPT) or phosphoribosyl transferase gene (gpt).

Marker genes induce a color reaction in transduced cells, which can be used to identify transduced cells. The skilled practitioner is familiar with a variety of marker genes, which can be used in a poxviral system. Among these are the gene encoding, e.g., β-galactosidase (β-gal), β-glucosidase (β-glu), green fluorescence protein (EGFP) or blue fluorescence protein.

According to still a further embodiment of the present invention the exogenous DNA sequence comprises a spacing sequence, which separates poxviral transcription control element and/or coding sequence in the exogenous DNA sequence from the stop codon and/or the start codon of the adjacent ORFs. This spacer sequence between the stop/start codon of the adjacent ORF and the inserted coding sequence in the exogenous DNA has the advantage to stabilize the inserted exogenous DNA and, thus, any resulting recombinant virus. The size of the spacer sequence is variable as long as the sequence is without its own coding or regulatory function.

According to a further embodiment, the spacer sequence separating the poxviral transcription control element and/or the coding sequence in the exogenous DNA sequence from the stop codon of the adjacent ORF is at least one nucleotide long.

According to another embodiment of the present invention, the spacing sequence separating the poxviral transcription control element and/or the coding sequence in the exogenous DNA sequence from the start codon of the adjacent ORF is at least 30 nucleotides. Particularly, in cases where a typical vaccinia virus promoter element is identified upstream of a start codon the insertion of exogenous DNA may not separate the promoter element from the start codon of the adjacent ORF. A typical vaccinia promoter element can be identified by scanning for e.g., the sequence "TAAAT" for late promoters (Davison & Moss 1989 *J. Mol. Biol.;* 210:771-784) and an A/T rich domain for early promoters. A spacing sequence of about 30 nucleotides is the preferred distance to secure that a poxviral promoter located upstream of the start codon of the ORF is not influenced. Additionally, according to a further preferred embodiment, the distance between the inserted exogenous DNA and the start codon of the adjacent ORF is around 50 nucleotides and more preferably around 100 nucleotides.

According to a further preferred embodiment of the present invention, the spacing sequence comprises an additional poxviral transcription control element which is capable to control the transcription of the adjacent ORF.

A typical MVA strain which can be used according to the present invention for generating a recombinant MVA is MVA 1974/NIH Clone 1 that has been deposited as ATCC Accession No.: PTA-5095 on Mar. 27, 2003 with the American Type Culture Collection (ATCC), 10801 University Blvd., Manassas, Va. 20110-2209, USA.

The term "derivatives" of a virus according to the present invention refers to progeny viruses showing the same characteristic features as the parent virus but showing differences in one or more parts of its genome. The term "derivative of MVA" describes a virus, which has the same functional characteristics compared to MVA. For example, a derivative of MVA 1974/NIH Clone 1 has the characteristic features of MVA 1974/NIH Clone 1. One of these characteristics of MVA 1974/NIH Clone 1 or derivatives thereof is its attenuation and severe restriction in host range.

The recombinant MVA according to the present invention is useful as a medicament or vaccine. It is, according to a further embodiment, used for the introduction of the exogenous coding sequence into a target cell, said sequence being either homologous or heterologous to the genome of the target cell.

The introduction of an exogenous coding sequence into a target cell may be done in vitro to produce proteins, polypeptides, peptides, antigens or antigenic epitopes. This method comprises the infection of a host cell with the recombinant MVA according to the invention, cultivation of the infected host cell under suitable conditions, and isolation and/or enrichment of the polypeptide, peptide, protein, antigen, epitope and/or virus produced by said host cell.

Furthermore, the method for introduction of one or more homologous or one or more heterologous sequence into cells may be applied for in vitro and in vivo therapy. For in vitro therapy, isolated cells that have been previously (er vivo) infected with the recombinant MVA according to the invention are administered to the living animal body for affecting, preferably inducing an immune response. For in vive therapy, the recombinant poxvirus according to the invention is directly administered to the living animal body for affecting, preferably inducing an immune response. In this case, the cells surrounding the site of inoculation, but also cells where the virus is transported to via, e.g., the blood stream, are directly infected in vivo by the recombinant MVA according to the invention. After infection, these cells synthesize the proteins, peptides or antigenic epitopes of the therapeutic genes, which are encoded by the exogenous coding sequences and, subsequently, present them or parts thereof on the cellular surface. Specialized cells of the immune system recognize the presentation of such heterologous proteins, peptides or epitopes and launch a specific immune response.

Since the MVA is highly growth restricted and, thus, highly attenuated, it is useful for the treatment of a wide range of mammals including humans, including immune-compromised animals or humans. The present invention also provides pharmaceutical compositions and vaccines for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the recombinant poxvirus according to the invention is converted into a physiologically acceptable form. This can be done based on the experience in the preparation of poxvirus vaccines used for vaccination against smallpox (as described by Stickl, H. et al. 1974 *Dtsch Med Wochenschr.* 99:2386-2392). For example, the purified virus is stored at −80° C. with a titer of 5×10E8 TCIDs/ml formulated in about 10 mM Tris, 140 mM NaCl pH 7.4. For the preparation of vaccine shots, e.g., 10E2-10E8 particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e., parenterally, subcutaneous, intramuscularly, by scarification or any other path of administration know to the skilled practitioner. The mode of administration, the dose and the number of administrations can be optimized by those skilled in the art in a known manner. However, most commonly a patient is vaccinated with a second shot about one month to six weeks after the first vaccination shot.

The present invention further relates to plasmid vectors, which can be used to generate recombinant MVA according to the present invention, and also relates to certain DNA sequences.

Regularly, the IGR located between or flanked by two adjacent ORFs comprises nucleotide sequences in which the exogenous DNA sequence of interest can be inserted. Accordingly, the plasmid vector according to the present invention comprises a DNA sequence derived from or homologous to the genome of MVA, wherein said DNA sequence comprises a complete or partial fragment of an IGR sequence located between or flanked by two adjacent ORFs of the viral genome. Preferably, the plasmid vector comprises inserted into said IGR-derived sequence at least one cloning site for the insertion of an exogenous DNA sequence of interest and, preferably, for the insertion of a poxviral transcription control element operatively linked to said heterologous DNA sequence. Optionally, the plasmid vector comprises a reporter- and/or selection gene cassette. The plasmid vector preferably also comprises sequences of the two adjacent ORFs flanking said complete or partial fragment of the IGR sequence.

Some IGRs have been identified which do not include nucleotide sequences. In these cases, the plasmid vector comprises DNA sequences of the IGR flanking sequences, i.e., DNA sequences of the two adjacent ORFs. Preferably, the cloning site for the insertion of the heterologous DNA sequence is inserted into the IGR. The DNA of the IGR flanking sequences is used to direct the insertion of exogenous DNA sequences into the corresponding IGR in the MVA genome. Such a plasmid vector may additionally include a complete or partial fragment of an IGR sequence which comprises the cloning site for the insertion of the heterologous DNA sequence and, optionally, of the, reporter- and/or selection gene cassette.

IGR-DNA sequences as well as IGR flanking sequences of the two adjacent ORFs are preferably selected from IGRs and ORFs, respectively, selected from the group consisting of (using the nomenclature according to CDC/Acambis):
044-045, 049-050, 050-051, 058-059, 064-065, 065-066, 069-070, 070-071, 071-072, 072-073, 073-074, 074-075, 075-076, 076-077, 077-078, 078-079, 081-082, 085-086, 086-087, 089-090, 092-093, 093-094, 095-096, 097-098, 100-101, 101-102, 102-103, 104-105, 108-109, 113-114, 114-115, 118-119, 121-122, 122-123, 123-124, 127-128, 128-129, 129-130, 130-131, 131-132, 132-133, 133-134, 134-135, 135-136, 141-142, and 142-143, in an exemplary manner or corresponding thereto in other strains of vaccinia virus.

The sequences are, more preferably, selected from IGRs and ORFs, respectively, selected from the group consisting of 049-050, 071-072, 074-075, 078-079, 092-093, 100-101, 118-119, 121-122, and 132-133.

In a working example, the IGR derived sequence is selected as 071-072.

The DNA sequences are preferably derived from or homologous to the genome of the MVA deposited as ATCC Accession No.: PTA-5095 on Mar. 27, 2003 with the American Type Culture Collection (ATCC), 10801 University Blvd., Manassas, Va. 20110-2209, USA.

To generate a plasmid vector according to the present invention the sequences are isolated and cloned into a standard cloning vector, such as pBluescript (Stratagene), wherein they flank the exogenous DNA to be inserted into the MVA genome. Optionally, such a plasmid vector comprises a selection- or reporter gene cassette, which can be deleted from the final recombinant virus, due to a repetitive sequence included into said cassette.

Methods to introduce exogenous DNA sequences by a plasmid vector into an MVA genome and methods to obtain recombinant MVA are well known to the person skilled in the art and, additionally, can be deduced can be deduced from *Molecular Cloning. A Laboratory Manual*, Second Edition, J. Sambrook, E. F. Fritsch and T. Maniatis, Cold Spring Harbor Laboratory Press, 1989 and *Current Protocols in Molecular Biology*, John Wiley and Son Inc. 1998, Chapter 16, section IV, "Expression of proteins in mammalian cells using vaccinia viral vectors".

The MVA according to the present invention may be produced by transfecting a cell with a plasmid vector according to the present invention, infecting the transfected cell with an MVA and, subsequently, identifying, isolating and, optionally, purifying the MVA according to the invention.

The DNA sequences according to the invention can be used to identify or isolate the MVA or its derivatives according to the invention and cells or individuals infected with an MVA according to the present invention. The DNA sequences are, e.g., used to generate PCR-primers, hybridization probes or are used in array technologies.

HIVs and Their Replication

The etiological agent of acquired immune deficiency syndrome (AIDS) is recognized to be a retrovirus exhibiting characteristics typical of the lentivirus genus, referred to as human immunodeficiency virus (HIV). The phylogenetic relationships of the human lentiviruses are shown in FIG. 1. HIV-2 is more closely related to $SIV_{smm}$, a virus isolated from sooty mangabey monkeys in the wild, than to HIV-1. It is currently believed that HIV-2 represents a zoonotic transmission of $SIV_{smm}$ to man. A series of lentiviral isolates from captive chimpanzees, designated $SIV_{cpz}$, are close genetic relatives of HIV-1.

Figure 2:
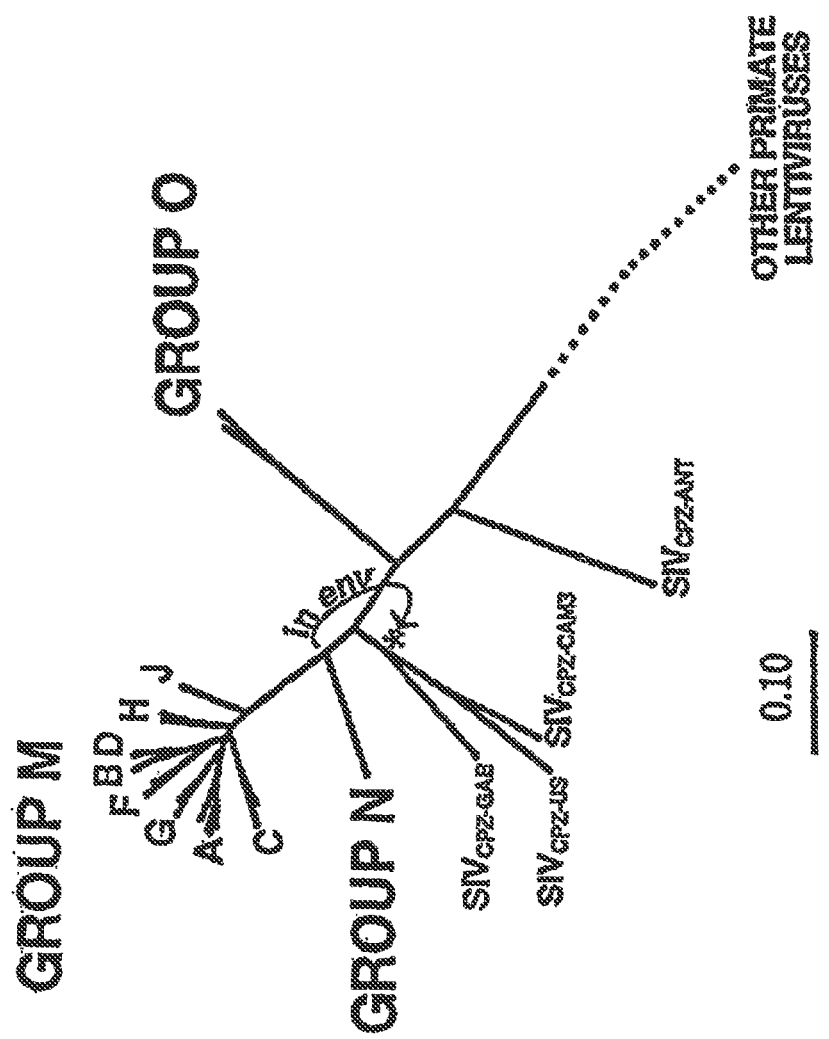
FIG. 2. Phylogenetic relationships of HIV-1 groups M, N and O with four different SIV$_{cpz}$ isolates based on full-length pol gene sequences. The bar indicates a genetic distance of 0.1 (10% nucleotide divergence) and the asterisk positions group N HIV-1 isolates based on env sequences.

The earliest phylogenetic analyses of HIV-1 isolates focused on samples from Europe/North America and Africa; discrete clusters of viruses were identified from these two areas of the world. Distinct genetic subtypes or clades of HIV-1 were subsequently defined and classified into three groups: M (major); O (outlier); and N (non-M or O) (FIG. 2). The M group of HIV-1, which includes over 95% of the global virus isolates, consists of at least eight discrete clades (A, B, C, D, F, G, H, and J), based on the sequence of complete viral genomes. Members of HIV-1 group O have been recovered from individuals living in Cameroon, Gabon, and Equatorial Guinea; their genomes share less than 50% identity in nucleotide sequence with group M viruses. The more recently discovered group N HIV-1 strains have been identified in infected Cameroonians, fail to react serologically in standard whole-virus enzyme-linked immunosorbent assay (ELISA), yet are readily detectable by conventional Western blot analysis.

Most current knowledge about HIV-1 genetic variation comes from studies of group M viruses of diverse geographic origin. Data collected during the past decade indicate that the HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

All of the HIV-1 group M subtypes can be found in Africa. Clade A viruses are genetically the most divergent and were the most common HIV-1 subtype in Africa early in the epidemic. With the rapid spread of HIV-1 to southern Africa during the mid to late 1990s, clade C viruses have become the dominant subtype and now account for 48% of HIV-1 infections worldwide. Clade B viruses, the most intensively studied HIV-1 subtype, remain the most prevalent isolates in Europe and North America.

High rates of genetic recombination are a hallmark of retroviruses. It was initially believed that simultaneous infections by genetically diverse virus strains were not likely to be established in individuals at risk for HIV-1. By 1995, however, it became apparent that a significant fraction of the HIV-1 group M global diversity included interclade viral recombinants. It is now appreciated that HIV-1 recombinants will be found in geographic areas such as Africa, South America, and Southeast Asia, where multiple HIV-1 subtypes coexist and may account for more than 10% of circulating HIV-1 strains. Molecularly, the genomes of these recombinant viruses resemble patchwork mosaics, with juxtaposed diverse HIV-1 subtype segments, reflecting the multiple crossover events contributing to their generation. Most HIV-1 recombinants have arisen in Africa and a majority contains segments originally derived from clade A viruses. In Thailand, for example, the composition of the predominant circulating strain consists of a clade A gag plus pol gene segment and a clade E env gene. Because the clade E env gene in Thai HIV-1 strains is closely related to the clade E env present in virus isolates from the Central African Republic, it is believed that the original recombination event occurred in Africa, with the subsequent introduction of a descendent virus into Thailand. Interestingly, no full-length HIV-1 subtype E isolate (i.e., with subtype E gag, pol, and env genes) has been reported to date.

The discovery that α and β chemokine receptors function as coreceptors for virus fusion and entry into susceptible CD4+ cells has led to a revised classification scheme for HIV-1 (FIG. 3). Isolates can now be grouped on the basis of chemokine receptor utilization in fusion assays in which HIV-1 gp120 and CD4+ coreceptor proteins are expressed in separate cells. As indicated in FIG. 3, HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

Figure 4:
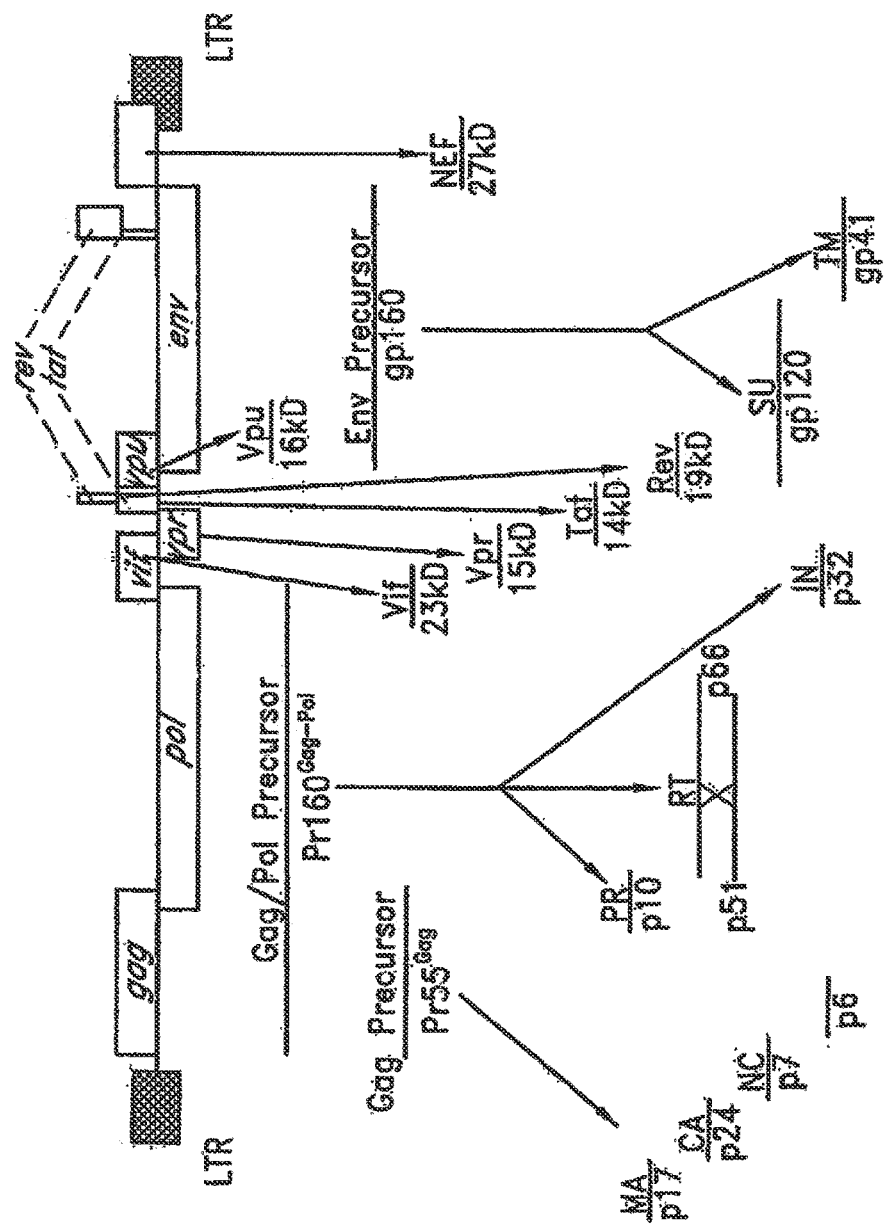
FIG. 4. HIV-encoded proteins. The location of the HIV genes, the sizes of primary translation products (in some cases polyproteins), and the processed mature viral proteins are indicated.

As is the case for all replication-competent retroviruses, the three primary HIV-1 translation products, all encoding structural proteins, are initially synthesized as polyprotein precursors, which are subsequently processed by viral or cellular proteases into mature particle-associated proteins (FIG. 4). The 55-kd Gag precursor $Pr55^{Gag}$ is cleaved into the matrix (MA), capsid (CA), nucleocapsid (NC), and p6 proteins. Autocatalysis of the 160-kd Gag-Pol polyprotein, $Pr160^{Gag-Pol}$, gives rise to the protease (PR), the heterodimeric reverse transcriptase (RT), and the integrase (IN) proteins, whereas proteolytic digestion by a cellular enzyme(s) converts the glycosylated 160-kd Env precursor gp160 to the gp120 surface (SU) and gp41 transmembrane (TM) cleavage products. The remaining six HIV-1-encoded proteins (Vif, Vpr, Tat, Rev, Vpu, and Nef) are the primary translation products of spliced mRNAs.

Gag

Figure 5:
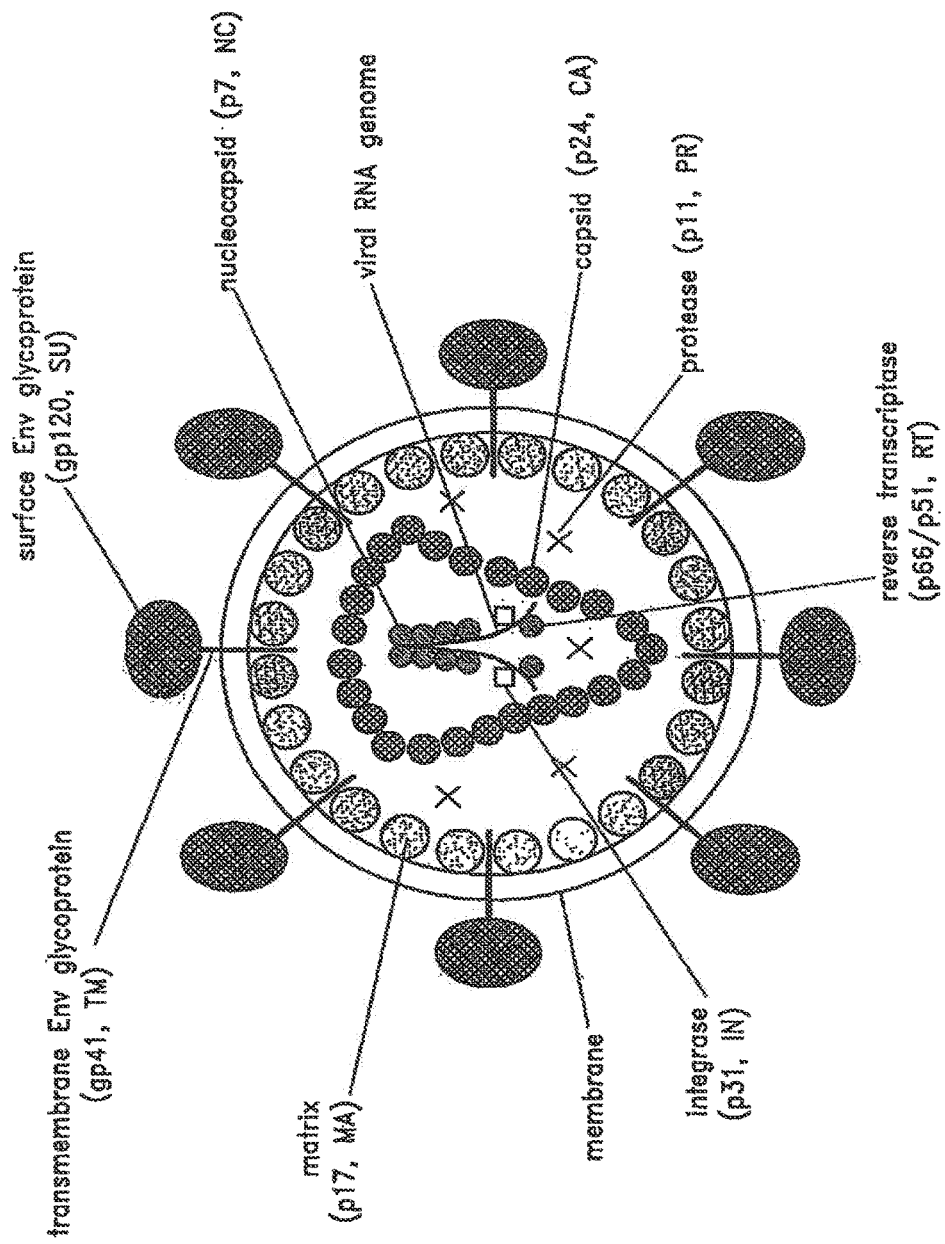
FIG. 5. Schematic representation of a mature HIV-1 virion.

The Gag proteins of HIV, like those of other retroviruses, are necessary and sufficient for the formation of noninfectious, virus-like particles. Retroviral Gag proteins are generally synthesized as polyprotein precursors; the HIV-1 Gag precursor has been named, based on its apparent molecular mass, $Pr55^{Gag}$. As noted previously, the mRNA for $Pr55^{Gag}$ is the unspliced 9.2-kb transcript (FIG. 4) that requires Rev for its expression in the cytoplasm. When the pol ORF is present, the viral protease (PR) cleaves $Pr55^{Gag}$ during or shortly after budding from the cell to generate the mature Gag proteins p17 (MA), p24 (CA), p7 (NC), and p6 (see FIG. 4). In the virion, MA is localized immediately inside the lipid bilayer of the viral envelope, CA forms the outer portion of the cone-shaped core structure in the center of the particle, and NC is present in the core in a ribonucleoprotein complex with the viral RNA genome (FIG. 5).

The HIV $Pr55^{Gag}$ precursor oligomerizes following its translation and is targeted to the plasma membrane, where particles of sufficient size and density to be visible by EM are assembled. Formation of virus-like particles by Pr55$^{Gag}$ is a self-assembly process, with critical Gag-Gag interactions taking place between multiple domains along the Gag precursor. The assembly of virus-like particles does not require the participation of genomic RNA (although the presence of nucleic acid appears to be essential), pol-encoded enzymes, or Env glycoproteins, but the production of infectious virions requires the encapsidation of the viral RNA genome and the incorporation of the Env glycoproteins and the Gag-Pol polyprotein precursor Pr160$^{Gag-Pol}$.

Pol

Downstream of gag lies the most highly conserved region of the HIV genome, the pol gene, which encodes three enzymes: PR, RT, and IN (see FIG. 4). RT and IN are required, respectively, for reverse transcription of the viral RNA genome to a double-stranded DNA copy, and for the integration of the viral DNA into the host cell chromosome. PR plays a critical role late in the life cycle by mediating the production of mature, infectious virions. The pol gene products are derived by enzymatic cleavage of a 160-kd Gag-Pol fusion protein, referred to as Pr160$^{Gag-Pol}$. This fusion protein is produced by ribosomal frameshifting during translation of Pr55$^{Gag}$ (see FIG. 4). The frame-shifting mechanism for Gag-Pol expression, also utilized by many other retroviruses, ensures that the pol-derived proteins are expressed at a low level, approximately 5% to 10% that of Gag. Like Pr55$^{Gag}$, the N-terminus of Pr160$^{Gag-Pol}$ is myristylated and targeted to the plasma membrane.

Protease

Early pulse-chase studies performed with avian retroviruses clearly indicated that retroviral Gag proteins are initially synthesized as polyprotein precursors that are cleaved to generate smaller products. Subsequent studies demonstrated that the processing function is provided by a viral rather than a cellular enzyme, and that proteolytic digestion of the Gag and Gag-Pol precursors is essential for virus infectivity. Sequence analysis of retroviral PRs indicated that they are related to cellular "aspartic" proteases such as pepsin and renin. Like these cellular enzymes, retroviral PRs use two apposed Asp residues at the active site to coordinate a water molecule that catalyzes the hydrolysis of a peptide bond in the target protein. Unlike the cellular aspartic proteases, which function as pseudodimers (using two folds within the same molecule to generate the active site), retroviral PRs function as true dimers. X-ray crystallographic data from HIV-1 PR indicate that the two monomers are held together in part by a four-stranded antiparallel β-sheet derived from both N- and C-terminal ends of each monomer. The substrate-binding site is located within a cleft formed between the two monomers. Like their cellular homologs, the HIV PR dimer contains flexible "flaps" that overhang the binding site and may stabilize the substrate within the cleft; the active-site Asp residues lie in the center of the dimer. Interestingly, although some limited amino acid homology is observed surrounding active-site residues, the primary sequences of retroviral PRs are highly divergent, yet their structures are remarkably similar.

Reverse Transciptase

By definition, retroviruses possess the ability to convert their single-stranded RNA genomes into double-stranded DNA during the early stages of the infection process. The enzyme that catalyzes this reaction is RT, in conjunction with its associated RNaseH activity. Retroviral RTs have three enzymatic activities: (a) RNA-directed DNA polymerization (for minus-strand DNA synthesis), (b) RNaseH activity (for the degradation of the tRNA primer and genomic RNA present in DNA-RNA hybrid intermediates), and (c) DNA-directed DNA polymerization (for second- or plus-strand DNA synthesis).

The mature HIV-1 RT holoenzyme is a heterodimer of 66 and 51 kd subunits. The 51-kd subunit (p51) is derived from the 66-kd (p66) subunit by proteolytic removal of the C-terminal 15-kd RNaseH domain of p66 by PR (see FIG. 4). The crystal structure of HIV-1 RT reveals a highly asymmetric folding in which the orientations of the p66 and p51 subunits differ substantially. The p66 subunit can be visualized as a right hand, with the polymerase active site within the palm, and a deep template-binding cleft formed by the palm, fingers, and thumb subdomains. The polymerase domain is linked to RNaseH by the connection subdomain. The active site, located in the palm, contains three critical Asp residues (110, 185, and 186) in close proximity, and two coordinated $Mg^{2+}$ ions. Mutation of these Asp residues abolishes RT polymerizing activity. The orientation of the three active-site Asp residues is similar to that observed in other DNA polymerases (e.g., the Klenow fragment of E. coli DNA polI). The p51 subunit appears to be rigid and does not form a polymerizing cleft; Asp 110, 185, and 186 of this subunit are buried within the molecule. Approximately 18 base pairs of the primer-template duplex lie in the nucleic acid binding cleft, stretching from the polymerase active site to the RNaseH domain.

In the RT-primer-template-dNTP structure, the presence of a dideoxynucleotide at the 3' end of the primer allows visualization of the catalytic complex trapped just prior to attack on the incoming dNTP. Comparison with previously obtained structures suggests a model whereby the fingers close in to trap the template and dNTP prior to nucleophilic attack of the 3'-OH of the primer on the incoming dNTP. After the addition of the incoming dNTP to the growing chain, it has been proposed that the fingers adopt a more open configuration, thereby releasing the pyrophosphate and enabling RT to bind the next dNTP. The structure of the HIV-1 RNaseH has also been determined by x-ray crystallography; this domain displays a global folding similar to that of E. coli RNaseH.

Integrase

A distinguishing feature of retrovirus replication is the insertion of a DNA copy of the viral genome into the host cell chromosome following reverse transcription. The integrated viral DNA (the provirus) serves as the template for the synthesis of viral RNAs and is maintained as part of the host cell genome for the lifetime of the infected cell. Retroviral mutants deficient in the ability to integrate generally fail to establish a productive infection.

The integration of viral DNA is catalyzed by integrase, a 32-kd protein generated by PR-mediated cleavage of the C-terminal portion of the HIV-1 Gag-Pol polyprotein (see FIG. 4).

Retroviral IN proteins are composed of three structurally and functionally distinct domains: an N-terminal, zinc-finger-containing domain, a core domain, and a relatively nonconserved C-terminal domain. Because of its low solubility, it has not yet been possible to crystallize the entire 288-amino-acid HIV-1 IN protein. However, the structure of all three domains has been solved independently by x-ray crystallography or NMR methods. The crystal structure of the core domain of the avian sarcoma virus IN has also been determined. The N-terminal domain (residues 1 to 55), whose structure was solved by NMR spectroscopy, is composed of four helices with a zinc coordinated by amino acids His-12, His-16, Cys-40, and Cys-43. The structure of the N-terminal domain is reminiscent of helical DNA binding proteins that contain a so-called helix-turn-helix motif; however, in the HIV-1 structure this motif contributes to dimer formation. Initially, poor solubility hampered efforts to solve the structure of the core domain. However, attempts at crystallography were successful when it was observed that a Phe-to-Lys change at IN residue 185 greatly increased solubility without disrupting in vitro catalytic activity. Each monomer of the HIV-1 IN core domain (IN residues 50 to 212) is composed of a five-stranded β-sheet flanked by helices; this structure bears striking resemblance to other polynucleotidyl transferases including RNaseH and the bacteriophage MuA transposase. Three highly conserved residues are found in analogous positions in other polynucleotidyl transferases; in HIV-1 IN these are Asp-64, Asp-16 and Glu-152, the so-called D,D-35-E motif. Mutations at these positions block HIV IN function both in vivo and in vitro. The close proximity of these three amino acids in the crystal structure of both avian sarcoma virus and HIV-1 core domains supports the hypothesis that these residues play a central role in catalysis of the polynucleotidyl transfer reaction that is at the heart of the integration process. The C-terminal domain, whose structure has been solved by NMR methods, adopts a five-stranded β-barrel folding topology reminiscent of a Src homology 3 (SH3) domain. Recently, the x-ray structures of SIV and Rous sarcoma virus IN protein fragments encompassing both the core and C-terminal domains have been solved.

Env

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

Figure 6:
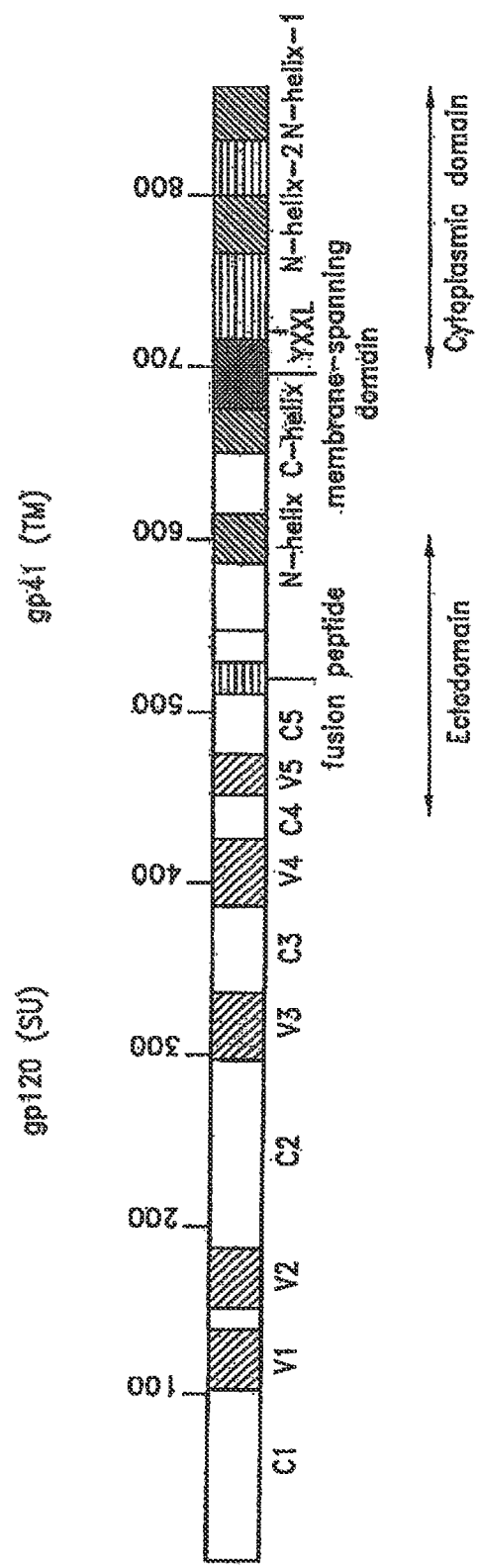
FIG. 6. Linear representation of the HIV-1 Env glycoprotein. The arrow indicates the site of gp160 cleavage to gp120 and gp41. In gp120, cross-hatched areas represent variable domains ($V_1$ to $V_5$) and open boxes depict conserved sequences ($C_1$ to $C_5$). In the gp41 ectodomain, several domains are indicated: the N-terminal fusion peptide, and the two ectodomain helices (N- and C-helix). The membrane-spanning domain is represented by a black box. In the gp41 cytoplasmic domain, the Tyr-X-X-Leu (YXXL) endocytosis motif (SEQ ID NO: 1) and two predicted helical domains (helix-1 and -2) are shown. Amino acid numbers are indicated.

The HIV Env glycoprotein is synthesized from the singly spliced 4.3-kb Vpu/Env bicistronic mRNA (see FIG. 4); translation occurs on ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41 (FIG. 6). The gp160 is cotranslationally glycosylated, forms disulfide bonds, and undergoes oligomerization in the ER. The predominant oligomeric form appears to be a trimer, although dimers and tetramers are also observed. The gp160 is transported to the Golgi, where, like other retroviral envelope precursor proteins, it is proteolytically cleaved by cellular enzymes to the mature SU glycoprotein gp120 and TM glycoprotein gp41 (see FIG. 6). The cellular enzyme responsible for cleavage of retroviral Env precursors following a highly conserved Lys/Arg-X-Lys/Arg-Arg motif is furin or a furin-like protease, although other enzymes may also catalyze gp160 processing. Cleavage of gp160 is required for Env-induced fusion activity and virus infectivity. Subsequent to gp160 cleavage, gp120 and gp41 form a noncovalent association that is critical for transport of the Env complex from the Golgi to the cell surface. The gp120-gp41 interaction is fairly weak, and a substantial amount of gp120 is shed from the surface of Env-expressing cells.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. As shown in FIG. 6, gp120 contains interspersed conserved ($C_1$ to $C_5$) and variable ($V_1$ to $V_5$) domains. The Cys residues present in the gp120s of different isolates are highly conserved and form disulfide bonds that link the first four variable regions in large loops.

A primary function of viral Env glycoproteins is to promote a membrane fusion reaction between the lipid bilayers of the viral envelope and host cell membranes. This membrane fusion event enables the viral core to gain entry into the host cell cytoplasm. A number of regions in both gp120 and gp41 have been implicated, directly or indirectly, in Env-mediated membrane fusion. Studies of the $HA_2$ hemagglutinin protein of the orthomyxoviruses and the F protein of the paramyxoviruses indicated that a highly hydrophobic domain at the N-terminus of these proteins, referred to as the fusion peptide, plays a critical role in membrane fusion. Mutational analyses demonstrated that an analogous domain was located at the N-terminus of the HIV-1, HIV-2, and SIV TM glycoproteins (see FIG. 6). Nonhydrophobic substitutions within this region of gp41 greatly reduced or blocked syncytium formation and resulted in the production of noninfectious progeny virions.

C-terminal to the gp41 fusion peptide are two amphipathic helical domains (see FIG. 6) which play a central role in membrane fusion. Mutations in the N-terminal helix (referred to as the N-helix), which contains a Leu zipper-like heptad repeat motif, impair infectivity and membrane fusion activity, and peptides derived from these sequences exhibit potent antiviral activity in culture. The structure of the ectodomain of HIV-1 and SIV gp41, the two helical motifs in particular, has been the focus of structural analyses in recent years. Structures were determined by x-ray crystallography or NMR spectroscopy either for fusion proteins containing the helical domains, a mixture of peptides derived from the N- and C-helices, or in the case of the SIV structure, the intact gp41 ectodomain sequence from residue 27 to 149. These studies obtained fundamentally similar trimeric structures, in which the two helical domains pack in an antiparallel fashion to generate a six-helix bundle. The N-helices form a coiled-coil in the center of the bundle, with the C-helices packing into hydrophobic grooves on the outside.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Use of Recombinant MVA Virus to Boost CD+8 Cell Immune Response

The present invention relates to generation of a $CD8^+$ T cell immune response against an antigen and also eliciting an antibody response. More particularly, the present invention relates to "prime and boost" immunization regimes in which the immune response induced by administration of a priming composition is boosted by administration of a boosting composition. The present invention is based on prior experimental demonstration that effective boosting can be achieved using modified vaccinia Ankara (MVA) vectors, following priming with any of a variety of different types of priming compositions including recombinant MVA itself.

A major protective component of the immune response against a number of pathogens is mediated by T lymphocytes of the CD8+ type, also known as cytotoxic T lymphocytes (CTL). An important function of CD8+ cells is secretion of gamma interferon (IFNγ), and this provides a measure of CD8+ T cell immune response. A second component of the immune response is antibody directed to the proteins of the pathogen.

The present invention employs MVA which, as prior experiments show, has been found to be an effective means for providing a boost to a CD8+ T cell immune response primed to antigen using any of a variety of different priming compositions and also eliciting an antibody response.

Notably, prior experimental work demonstrates that use of predecessors of the present invention allows for recombinant MVA virus expressing an HIV antigen to boost a CD8+ T cell immune response primed by a DNA vaccine and also eliciting an antibody response. The MVA may be found to induce a CD8+ T cell response after immunization. Recombinant MVA may also be shown to prime an immune response that is boosted by one or more inoculations of recombinant MVA.

Non-human primates immunized with plasmid DNA and boosted with the MVA were effectively protected against intramucosal challenge with live virus (Amara et al 2001 *Science* 292:69-74). Advantageously, the inventors contemplate that a vaccination regime using intradermal, intramuscular or mucosal immunization for both prime and boost can be employed, constituting a general immunization regime suitable for inducing CD8+ T cells and also eliciting an antibody response, e.g., in humans.

The present invention in various aspects and embodiments employs an MVA vector encoding an HIV antigen for boosting a CD8+ T cell immune response to the antigen primed by previous administration of nucleic acid encoding the antigen and also eliciting an antibody response.

A general aspect of the present invention provides for the use of an MVA vector for boosting a CD8+ T cell immune response to an HIV antigen and also eliciting an antibody response.

One aspect of the present invention provides a method of boosting a CD8+ T cell immune response to an HIV antigen in an individual, and also eliciting an antibody response, the method including provision in the individual of an MVA vector including nucleic acid encoding the antigen operably linked to regulatory sequences for production of antigen in the individual by expression from the nucleic acid, whereby a CD8+ T cell immune response to the antigen previously primed in the individual is boosted.

An immune response to an HIV antigen may be primed by immunization with plasmid DNA or by infection with an infectious agent.

A further aspect of the invention provides a method of inducing a CD8+ T cell immune response to an HIV antigen in an individual, and also eliciting an antibody response, the method comprising administering to the individual a priming composition comprising nucleic acid encoding the antigen and then administering a boosting composition which comprises an MVA vector including nucleic acid encoding the antigen operably linked to regulatory sequences for production of antigen in the individual by expression from the nucleic acid.

A further aspect provides for use of an MVA vector, as disclosed, in the manufacture of a medicament for administration to a mammal to boost a CD8+ T cell immune response to an HIV antigen, and also eliciting an antibody response. Such a medicament is generally for administration following prior administration of a priming composition comprising nucleic acid encoding the antigen.

The priming composition may comprise DNA encoding the antigen, such DNA preferably being in the form of a circular plasmid that is not capable of replicating in mammalian cells. Any selectable marker should not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with a boosting composition, or first and second boosting compositions, the first and second boosting compositions being the same or different from one another. Still further boosting compositions may be employed without departing from the present invention. In one embodiment, a triple immunization regime employs DNA, then adenovirus as a first boosting composition, then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be encoded in respective priming and boosting compositions (however many boosting compositions are employed) need not be identical, but should share at least one CD8+ T cell epitope. The antigen may correspond to a complete antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

An HIV antigen of the invention to be encoded by a recombinant MVA virus includes polypeptides having immunogenic activity elicited by an amino acid sequence of an HIV Env, Gag, Pol, Vif, Vpr, Tat, Rev, Vpu, or Nef amino acid sequence as at least one CD8+ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full length Env precursor sequence is presented for use in the present invention, Env is optionally deleted of subsequences. For example, regions of the gp120 surface and gp41 transmembrane cleavage products can be deleted.

Although a full length Gag precursor sequence is presented for use in the present invention, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full length Pol precursor sequence is presented for use in the present invention, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Percent identity can be determined, for example, by comparing sequence information using the GAP computer program, version 6.0, available from the University of Wisconsin Genetics Computer Group (UWGCG). The GAP program utilizes the alignment method of Needleman and Wunsch (*J Mol Biol* 1970 48:443), as revised by Smith and Waterman (*Adv Appl Math* 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (*Nucl Acids Res* 1986 14:6745), as described by Schwartz and Dayhoff (eds., *Atlas of Protein Sequence and Structure*, National Biomedical Research Foundation, Washington, D.C. 1979, pp. 353-358); (2) a penalty of 3.0 for each gap and an additional 0.10 penalty for each symbol in each gap; and (3) no penalty for end gaps.

In a preferred embodiment, an Env of the present invention is a variant form of at least one HIV envelope protein. Preferably, the Env is composed of gp120 and the membrane-spanning and ectodomain of gp41 but lacks part or all of the cytoplasmic domain of gp41.

Known HIV sequences are readily available from commercial and institutional HIV sequence databases, such as GENBANK, or as published compilations, such as Myers et al. eds., *Human Retroviruses and AIDS, A Compilation and Analysis of Nucleic Acid and Amino Acid Sequences*, Vol. I and II, Theoretical Biology and Biophysics, Los Alamos, N. Mex. (1993), or on the world wide web at hiv-web.lanl.gov/.

Substitutions or insertions of an HIV Env, Gag, or Pol to obtain an additional HIV Env, Gag, or Pol, encoded by a nucleic acid for use in a recombinant MVA virus of the present invention, can include substitutions or insertions of at least one amino acid residue (e.g., 1-25 amino acids). Alternatively, at least one amino acid (e.g., 1-25 amino acids) can be deleted from an HIV Env, Gag, or Pol sequence. Preferably, such substitutions, insertions or deletions are identified based on safety features, expression levels, immunogenicity and compatibility with high replication rates of MVA.

Amino acid sequence variations in an HIV Env, Gag, or Pol of the present invention can be prepared e.g., by mutations in the DNA. Such HIV Env, Gag, or Pol include, for example, deletions, insertions or substitutions of nucleotides coding for different amino acid residues within the amino acid sequence. Obviously, mutations that will be made in nucleic acid encoding an HIV Env, Gag, or Pol must not place the sequence out of reading frame and preferably will not create complementary domains that could produce secondary mRNA structures.

HIV Env, Gag, or Pol-encoding nucleic acid of the present invention can also be prepared by amplification or site-directed mutagenesis of nucleotides in DNA or RNA encoding an HIV Env, Gag, or Pol and thereafter synthesizing or reverse transcribing the encoding DNA to produce DNA or RNA encoding an HIV Env, Gag, or Pol, based on the teaching and guidance presented herein.

Recombinant MVA viruses expressing HIV Env, Gag, or Pol of the present invention, include a finite set of HIV Env, Gag, or Pol-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., 1978 *Principles of Protein Structure*, Springer-Verlag, New York, N.Y., and Creighton, T. E., 1983 *Proteins: Structure and Molecular Properties*, W. H. Freeman & Co., San Francisco, Calif. For a presentation of nucleotide sequence substitutions, such as codon preferences, see Ausubel et al. eds. *Current Protocols in Molecular Biology*, Greene Publishing Assoc., New York, N.Y. 1994 at §§ A.1.1-A.1.24, and Sambrook, J. et al. 1989 *Molecular Cloning: A Laboratory Manual*, Second Edition, Cold Spring Harbor Laboratory Press, Cold Spring Harbor, N.Y. at Appendices C and D.

Thus, one of ordinary skill in the art, given the teachings and guidance presented herein, will know how to substitute other amino acid residues in other positions of an HIV env, gag, or pol DNA or RNA to obtain alternative HIV Env, Gag, or Pol, including substitutional, deletional or insertional variants.

Within the MVA vector, regulatory sequences for expression of the encoded antigen will include a promoter. By "promoter" is meant a sequence of nucleotides from which transcription may be initiated of DNA operably linked downstream (i.e., in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, marker genes and other sequences may be included as appropriate, in accordance with the knowledge and practice of the ordinary person skilled in the art: see, for example, Moss, B. (2001). Poxviridae: the viruses and their replication. In Fields Virology, D. M. Knipe, and P. M. Howley, eds. (Philadelphia, Lippincott Williams & Wilkins), pp. 2849-2883. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* 1998 Ausubel et al. eds., John Wiley & Sons.

Promoters for use in aspects and embodiments of the present invention may be compatible with poxvirus expression systems and include natural, modified and synthetic sequences.

Either or both of the priming and boosting compositions may include an adjuvant, such as granulocyte macrophage-colony stimulating factor (GM-CSF) or encoding nucleic acid therefor.

Administration of the boosting composition is generally about 1 to 6 months after administration of the priming composition, preferably about 1 to 3 months.

Preferably, administration of priming composition, boosting composition, or both priming and boosting compositions, is intradermal, intramuscular or mucosal immunization.

Administration of MVA vaccines may be achieved by using a needle to inject a suspension of the virus. An alternative is the use of a needleless injection device to administer a virus suspension (using, e.g., Biojector™ needleless injector) or a resuspended freeze-dried powder containing the vaccine, providing for manufacturing individually prepared doses that do not need cold storage. This would be a great advantage for a vaccine that is needed in rural areas of Africa.

MVA is a virus with an excellent safety record in human immunizations. The generation of recombinant viruses can be accomplished simply, and they can be manufactured reproducibly in large quantities. Intradermal, intramuscular or mucosal administration of recombinant MVA virus is therefore highly suitable for prophylactic or therapeutic vaccination of humans against AIDS which can be controlled by a $CD8^+$ T cell response.

The individual may have AIDS such that delivery of the antigen and generation of a $CD8^+$ T cell immune response to the antigen is of benefit or has a therapeutically beneficial effect.

Most likely, administration will have prophylactic aim to generate an immune response against HIV or AIDS before infection or development of symptoms.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, nasal, intramuscular, intraperitoneal routes.

As noted, administration is preferably intradermal, intramuscular or mucosal.

Physiological saline solution, dextrose or other saccharide solution or glycols such as ethylene glycol, propylene glycol or polyethylene glycol may be included.

For intravenous, cutaneous, subcutaneous, intramuscular or mucosal injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included as required.

A slow-release formulation may be employed.

Following production of MVA particles and optional formulation of such particles into compositions, the particles may be administered to an individual, particularly human or other primate. Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* 16th edition, 1980, Osol, A. (ed.).

In one preferred regimen, DNA is administered at a dose of 300 μg to 3 mg/injection, followed by MVA at a dose of $10^6$ to $10^9$ infectious virus particles/injection.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against HIV or AIDS.

A Shuttle Plasmid, Recombinant MVA/HIV1 Clinical Vaccine Construct and Mechanism for Retention of Intact Foreign Gene Inserts in Recombinant MVA by Codon Alteration of the Foreign Gene and Insertion of the Foreign Gene Between Two Vaccinia Virus Essential Genes The invention provides mechanisms for:

retention of intact foreign genes by inserting them between two vaccinia virus genes that are essential for MVA replication. Deletion of the foreign gene can provide a significant growth advantage for the recombinant MVA allowing it to compete with MVA containing the intact foreign gene upon repeated passage. However, most deletions of a foreign gene include loss of some part of the flanking vaccinia virus DNA. If that vaccinia virus DNA is essential, then those viruses with deletions will not replicate and compete with the MVA containing the intact foreign gene. This methodology will be useful in production of recombinant vaccinia viruses that must be amplified to large scale such as for use in clinical trials, and stabilizing foreign gene inserts by alteration of specific "hot spots" that otherwise readily undergo mutation after repeated passage of the recombinant virus. This methodology is useful in production of recombinant viruses that must be amplified to large scale such as for use in clinical trials.

And describes:

the shuttle plasmid, pLW-73, used for insertion of a foreign gene between 2 essential vaccinia virus genes; and the recombinant MVA/HIV-1 clinical vaccine construct MVA/UGD4d, a material that embodies use of these two mechanisms.

Novel Methods for Generation of Stable Recombinant MVA Viruses

The inventors have made modified vaccinia virus Ankara (MVA) recombinants expressing env and gagpol genes from HIV-1 isolates from different geographical locations. The foreign genes were inserted into 2 sites, Deletion II and Deletion III of MVA. The stability of these genes after repeated passage of recombinant MVA in tissue culture has proven to be variable. The inventors demonstrated that the instability was due to either deletion of the entire foreign gene and some flanking DNA or specific point mutations resulting in propagation of progeny virions that have a growth advantage because they do not express the foreign gene. Here the inventors describe two novel methods of retaining the intact foreign gene recombinant MVA. First, the inventors constructed a transfer vector that directs insertion of a foreign gene between two essential vaccinia virus genes in the conserved central region of the genome. Use of this site for insertion of genes prevents the outgrowth of variants containing large deletions that include the essential vaccinia virus DNA. In addition, this plasmid can be used for insertion of additional genes into recombinant viruses. Second, analysis of isolates with point mutations revealed certain "hot spots" with a propensity for insertion or deletion of a single base that causes premature termination during translation. The inventors showed that generation of silent mutations in these sites resulted in stabilization of the inserted gene.

I. Novel Transfer Vector Construction and Application

Construction of Novel Transfer Vector, pLW-73

1. The central region of the MVA genome, K7R-A24R, was examined for 1) pairs of genes conserved in the poxvirus family or chordopoxvirus subfamily and 2) genes that are in opposite orientation such that their 3' ends are in close proximity, thereby providing an insertion site that would not disrupt a vaccina promoter. The site chosen as the new insertion site was between two essential genes, I8R and G1L.

2. The left flank of the new vector was constructed in the following way: Plasmid LAS-1 was cut with restriction enzymes EcoRI and XhoI to remove the del III MVA flank, GFP, and direct repeat of MVA flank. This insert was cut with AscI and SacI and the GFP fragment was isolated. Five hundred thirty one base pairs at the end of the I8R gene (including the TAA stop codon) was PCR amplified with EcoRI and AscI restriction sites on the ends of the PCR product. PCR amplification of 229 base pairs of the direct repeat (from the end of the I8R gene including the TAA stop codon) was performed with oligonucleotides containing SacI and XhoI restriction sites. All four pieces of DNA, 1) the vector backbone with EcoRI and XhoI ends, 2) new left flank containing end of I8R with EcoRI and AscI ends, 3) GFP with AcsI and SacI ends and the 4) direct repeat of the I8R flank with SacI and XhoI ends were ligated together to make plasmid pLW-72.

Figure 7:
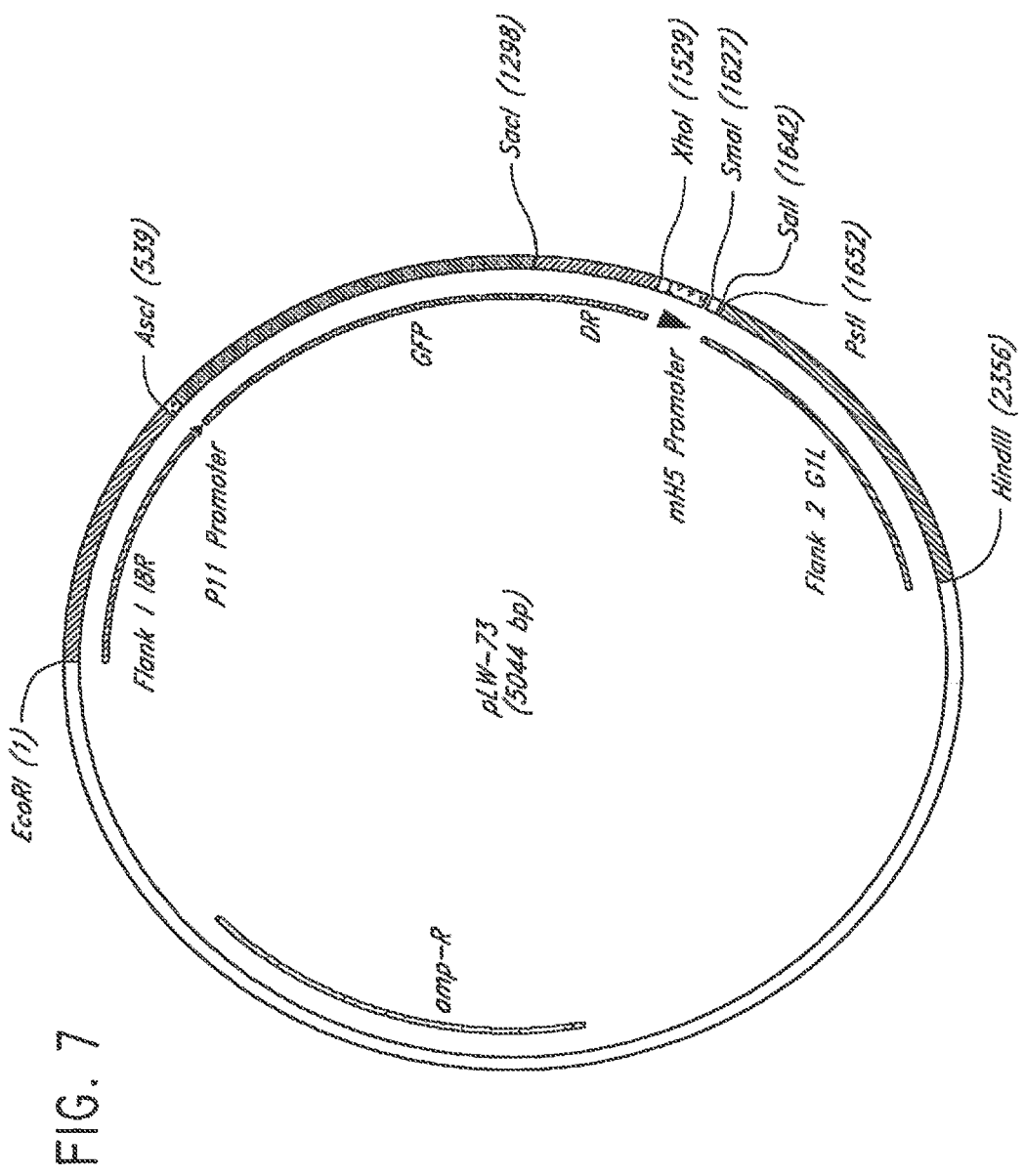
FIG. 7. pLW-73 transfer vector.

3. The right flank was made as follows: pLW-72 was cut with restriction enzymes PstI and HindIII to release del III flank of the MVA in the plasmid. Seven hundred and two base pairs at the end of the G1L gene was PCR amplified with PstI and HindIII restriction enzyme sites on the ends and ligated into the pLW-72 vector to make pLW-73 (FIG. 7). The sequence of pLW-73 is given in FIG. 8.

4. The salient features of pLW-73 are: 1) the vector was designed for insertion of foreign genes between essential genes in MVA genome. The left flank consists of end of I8R gene and right flank consists of end of G1L gene. 2) the GFP gene is included for easy initial selection of recombinant virus 3) the GFP is flanked by direct repeats of the I8R gene which allows for transient expression of GFP as the GFP will be lost upon repeated passage of the recombinant virus. Referring to WO 2004/087201, features 2 and 3 were also contained in earlier plasmids used for making MVA/HIV recombinants, pLAS-1 and pLAS-2.

Application of pLW-73

1. The env gene from the clade B ADA isolate of HIV-1 was cloned into pLW-73 and a recombinant MVA virus was made. DNA sequencing confirmed the location and integrity of the env gene.

2. A recombinant MVA virus expressing the Ugandan clade D (isolate AO7412) env gene (FIG. 9) in the Deletion II site of MVA proved to be unstable, i.e., after repeated serial passage in culture, the gene was deleted from a significant portion of the virus progeny. The same gene was then cloned into pLW-73 and a recombinant MVA virus was made and characterized. The env gene insert was stable after repeated serial passage (8×) in culture i.e., no deletions of the inserted gene or the MVA flanking region were found. In addition, no other mutations arose when the gene was inserted into this site.

II. Point Mutation of "Hot Spots"

Analysis of Point Mutations

A recombinant MVA virus expressing the Ugandan Clade D (isolate AO3349) gagpol gene in the Deletion III site of MVA proved to be unstable. The major genetic alteration was the generation of single point mutations in runs of 4-6 G or C residues (Table 3). In addition, similar point mutations were found in non-staining plaques from similar recombinant viruses expressing the gagpol genes from a Kenyan clade A isolate and a Tanzanian clade C isolate of HIV-1.

Mutagenesis of Hot Spots and Analysis of Stability in Recombinant Virus

Using site-directed mutagenesis, silent mutations were made in 6 such regions of the gag gene from the Ugandan HIV-1 isolate. This altered gene, UGD 4d gagpol orf (FIG. 10), was cloned into pLAS-1 and recombined into the same Deletion III site of MVA as was done in construction of the unstable virus. After repeated serial passage (8×) in culture, no non-expressing plaques were found. DNA sequencing of the passage 8 virus stock verified that the integrity of the gagpol gene was maintained.

III. Double Recombinant Construction

MVA/UGD4d Virus

MVA/UGD4d virus, a recombinant virus that expresses the Ugandan subtype D AO7412 envelope and the AO3349 gagpol, was constructed in the following way: The envelope and gagpol genes were inserted into MVA 1974/NIH Clone 1 by homologous recombination utilizing shuttle plasmids pLW-73 and pLAS-1, respectively. MVA/UGD4d was isolated by 6 rounds of plaque purification in chicken embryo fibroblast cells and subsequently amplified and characterized.

SUMMARY

1. A plasmid transfer vector was constructed that directs recombination of a foreign gene between two essential genes, I8R and G1L, in the conserved central region of the MVA genome. The use of this site was shown to inhibit selection of mutant viruses with deletions of inserted gene/MVA flanks.

2. Highly mutable runs of G and C residues were altered by site-directed mutagenesis and silent mutations in the coding sequence were generated. This change was shown to stabilize the gene when inserted into Deletion III of MVA.

3. Utilizing these two methods above, UGD4d double MVA recombinant that stably expresses both the env and gagpol of Ugandan Clade D was constructed.

Example 1

Recombinant MVAs expressing HIV-1 env and gagpol genes from many different isolates have been made. The stability of inserted genes after repeated passage in tissue culture has proven to be variable. Here the inventors (1) demonstrate that the instability represents a combination of spontaneous mutation or deletion of the inserted gene and selection for non-expressing mutants and (2) describe novel methods for reducing instability.

Overview

Recombinant MVAs expressing env and gagpol from many different isolates were constructed. Each virus was subjected to repeated passages in chicken embryo fibroblast cells to mimic the large-scale amplification required for production of virus for clinical trials. Insert stability was monitored by env and gag immunostaining of individual plaques. For some recombinant viruses, env and/or gag expression was found to be rapidly lost in a significant fraction of the virus population. To identify the mechanism(s) of loss of expression, individual plaques were isolated and the nature of the mutations was characterized. In some cases, specific DNA sequences with propensity to mutate by addition or deletion of a single nucleotide were identified. Generation of such mutations could be avoided by altering codons without changing the predicted translation product. In other cases, loss of expression was caused by large deletions that frequently extended into flanking non-essential MVA genes. To prevent this from occurring, a new shuttle plasmid was constructed that was designed to direct insertion of foreign genes between two essential MVA genes. Recombination into this site reduced deletions of the foreign DNA. In one case, however, the toxicity associated with high-level HIV env expression was so severe that the selection of rare mutants still resulted in an unstable population. In this case, only truncation of the transmembrane domain of env allowed the construction of a stable recombinant MVA.

Generation of Recombinant MVAs and Analysis of Stability of Inserted Genes

Env and gagpol genes were cloned into MVA shuttle vectors. Expression and function were analyzed by transient expression assays. Gagpol was recombined into MVA 1974/NIH Clone 1. Recombinant MVA were plaque purified with 6-8 rounds followed by amplification of virus. Env was recombined into the MVA/gagpol isolate and double-recombinant MVA (FIG. 11A) were plaque purified with 6-8 rounds and were amplified. To assess the stability of inserts, virus was serially passaged in CEF cells using a multiplicity of infection (m.o.i.) of ~1 pfu/cell to mimic large-scale production. Stability was evaluated by determining the percentage of cells expressing env or gag, as determined by immunostaining with monoclonal antibodies (FIG. 11B).

Stability of Recombinant MVAs

Recombinant MVAs expressing genes from HIV-1 isolates from different geographical locations were constructed. The env and gagpol genes were inserted into deletions II and III of MVA, respectively; both under control of the modified H5 promoter. The stability of env and gagpol genes from seven recombinant MVAs is shown in Table 4. Varying degrees of instability were observed in the seven viruses. In MVA/65A/G, expression of env was rapidly lost with only 25% of virions expressing env by passage 6. In MVA/UGD4a, both env and gagpol expression were increasingly lost with successive virus passages. Since at least 6-7 passages are required for production of a lot of virus for a Phase I trial, these two viruses were deemed unsuitable.

Analysis of Expression of MVA/65A/G

Figure 12:
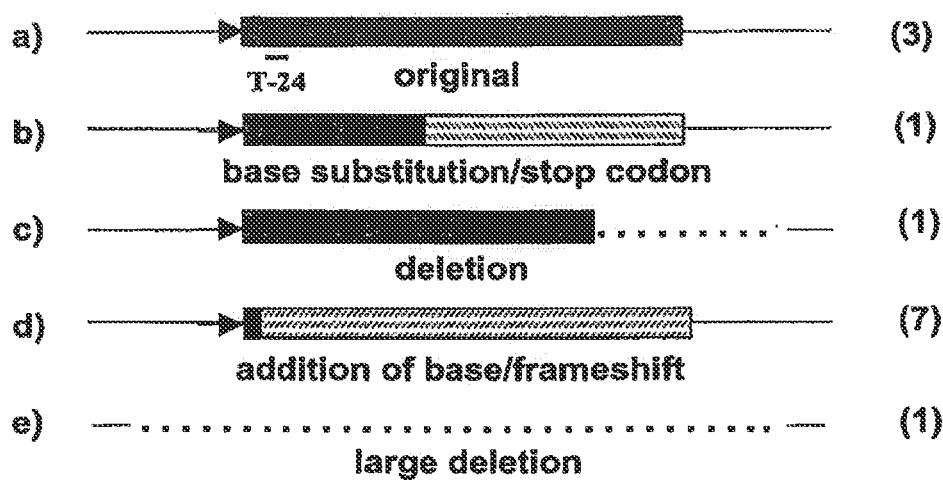
FIG. 12. Types and frequency of env mutations in MVA/65A/G env.

Referring to FIG. 12, thirteen plaques were randomly picked from P3 and P5 of MVA/65A/G and analyzed by immunostaining with T-24 mAb (binding site shown on a), Western blotting, PCR, and sequencing. Five types of plaques were found and the number of these plaques obtained for each type are given at right of FIG. 12. Plaques a, b, and c stained, but b and c were truncated versions due to base substitution (causing stop codon) (b) and deletion of the end of the env gene and part of MVA flank (c). Non-staining plaques d and e resulted from addition of G to a 5G run causing a frameshift (d) and large deletion of entire env gene and parts of MVA flanks (e). Thus, base pair addition, substitution, and deletions all contributed to unstable expression of the env gene in MVA/65A/G. This A/G env, the most unstable example worked with, was picked to study modifications that might enhance stability.

Modifications to A/G Constructs to Increase Stability

1. Synthetic envelope was made by removing 4 and 5 G and C runs by silent mutations to prevent point mutations.

Figure 13:
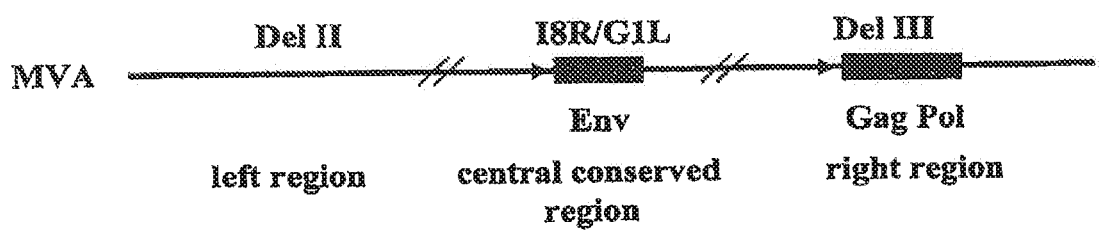
FIG. 13. Insertion of Env in I8R/G1L IGR and Gag Pol in Del III.

2. Vector I8/G1, i.e., pLW-73. was constructed with an insertion site between essential genes I8R and G1L to prevent deletions of genes and MVA flanks from being viable. The ends of the I8R (500 bp) and G1L (750 bp) genes of MVA were amplified by PCR and inserted into a vector containing vaccinia virus early/late mH5 promoter controlling foreign gene expression. This I8/G1 vector was used to insert foreign genes into MVA by homologous recombination (FIG. 13). Deletions of inserted genes and MVA flanking the inserted gene would not be viable because parts of essential genes would be deleted. Therefore, viruses with these mutations would not be able to overgrow the population with their normal growth advantage.

3. A/G gp140 envelope was mutated by deleting the transmembrane domain and the cytoplasmic tail of gp41, resulting in a secreted protein.

Testing Modifications to Increase Stability

Figure 14:
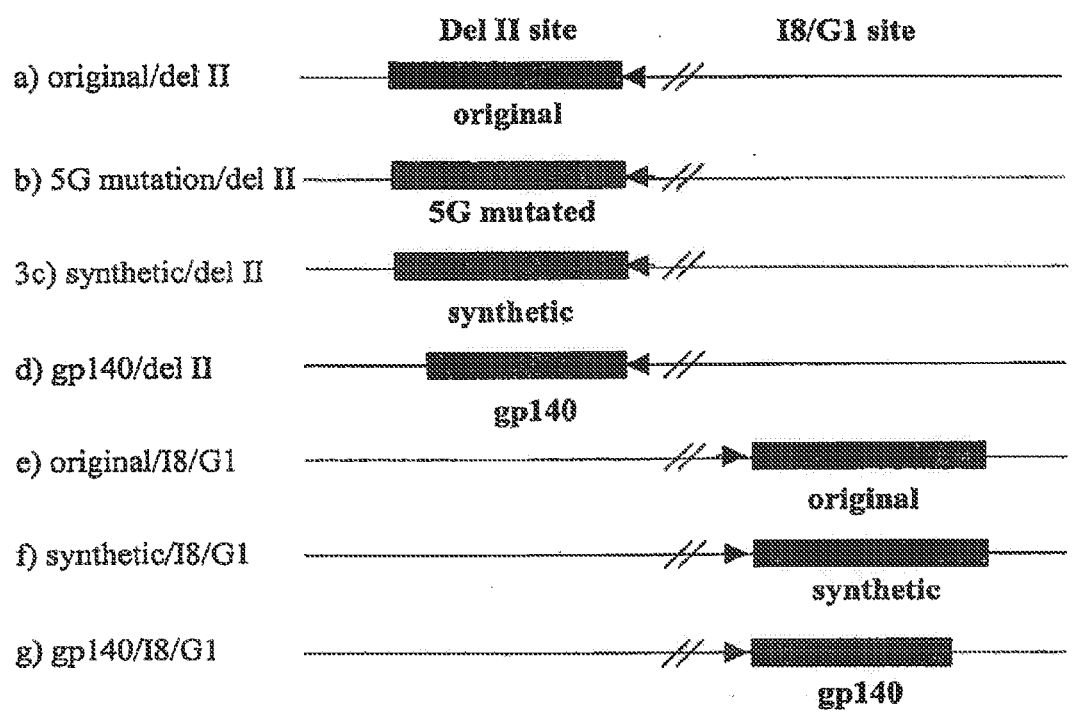
FIG. 14. Modifications to A/G constructs to increase stability.

Seven single recombinant viruses were made with env modifications and/or use of new vector as shown in FIG. 14. Five plaques of each virus were isolated and passaged independently in CEF to determine if modifications enhanced envelope stable expression. Passaged plaques were analyzed by immunostaining with mAb T-43 (binding site mapped to 101-125aa of env), Western blotting, PCR, and sequencing.

Env Expression after Plaque Passages

Figure 15:
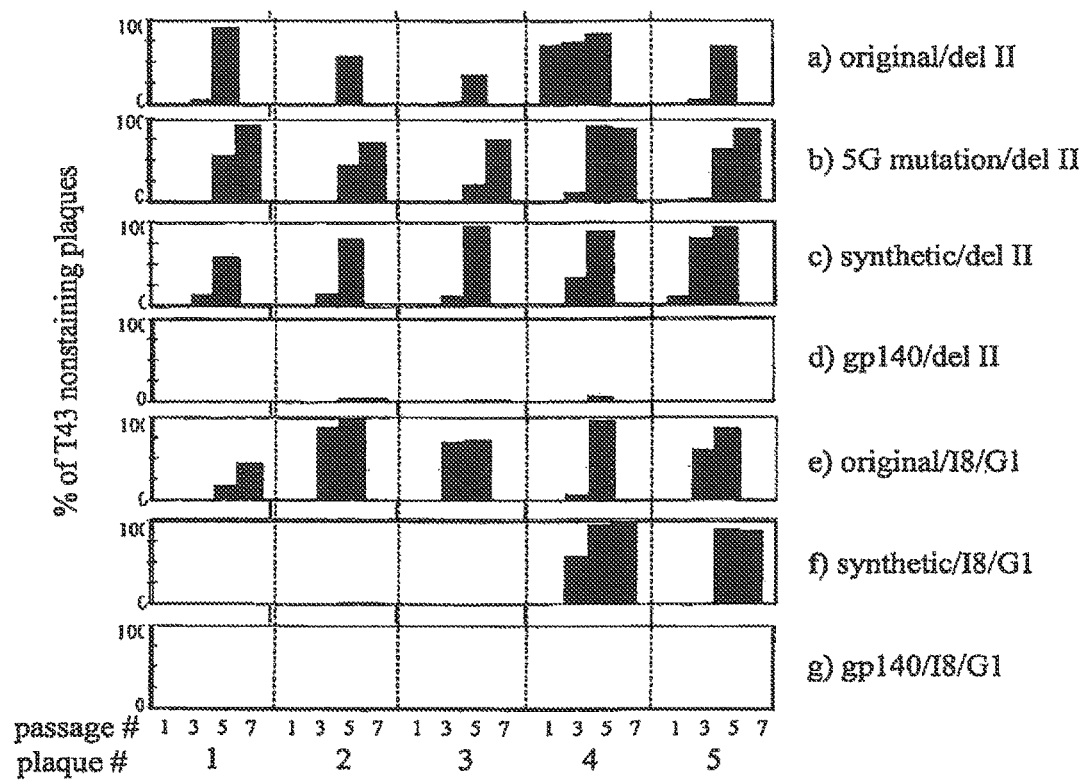
FIG. 15. Env expression after plaque passages.

Referring to FIG. 15, five independently passaged plaque isolates of each of the 7 recombinants listed above, were characterized at passages 1, 3, 5, and 7 by immunostaining with mAb T-43 (binds between 101-125a.a. in gp120). Four of 7 viruses (FIG. 15, a, b, c, e) had unstable protein expression in each of the 5 passaged plaques; two plaque passages of (FIG. 15f) also had unstable env expression. These included viruses with the synthetic env in both del II (FIG. 15c) and in the essential gene site (FIG. 15f) of MVA genome. Only recombinant viruses containing the envelope as truncated, secreted gp140 remained stably expressing envelope (FIGS. 15, d and g).

Western Blotting, PCR and Sequence Analyses

Figure 16:
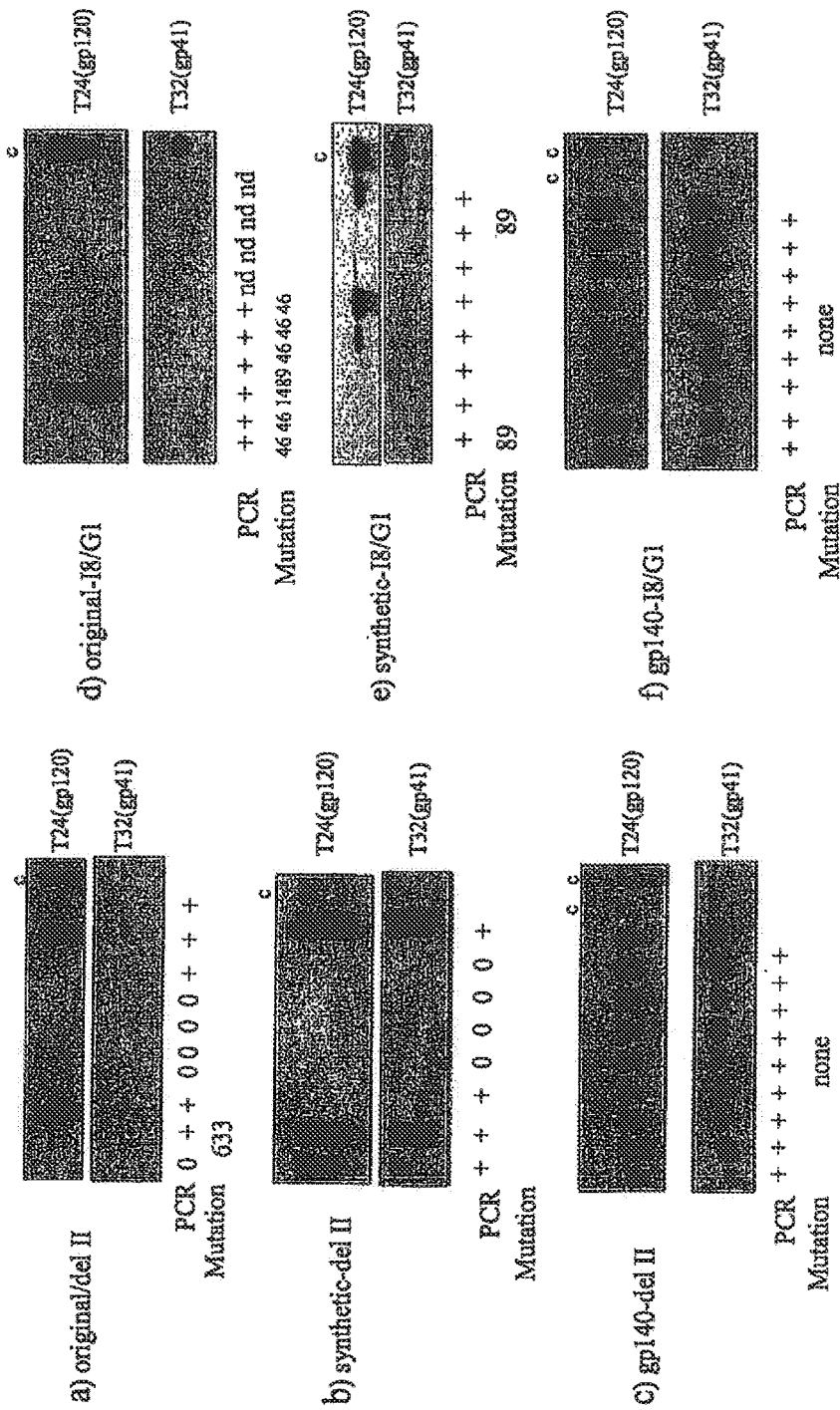
FIG. 16. PCR and Western blot analysis of individual clones.
Figure 17:
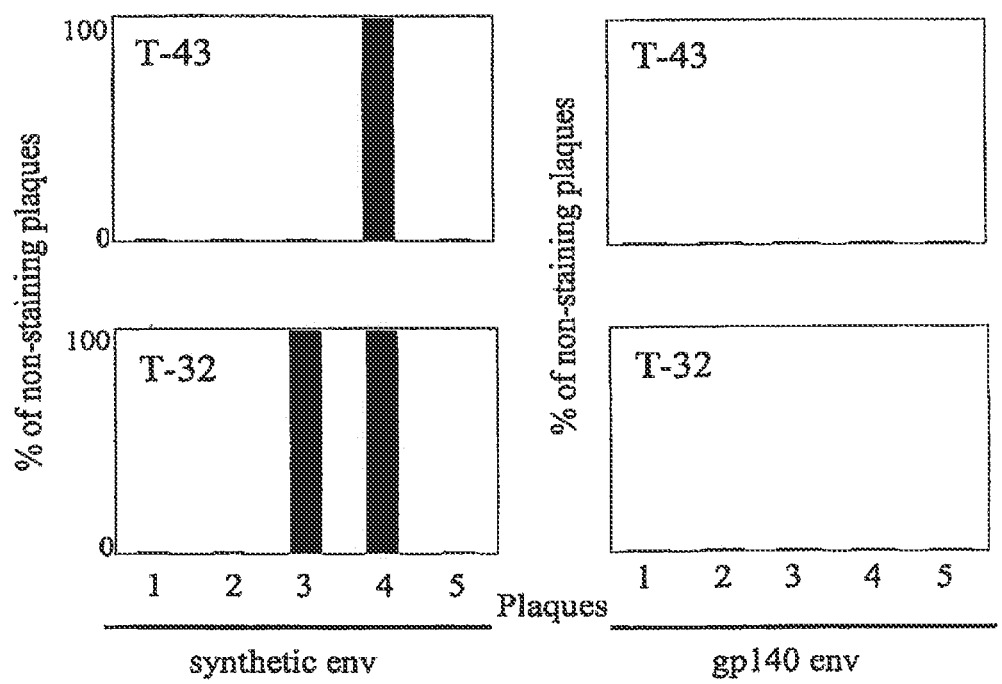
FIG. 17. Expression of A/G env by double recombinant MVA.
Figure 18:
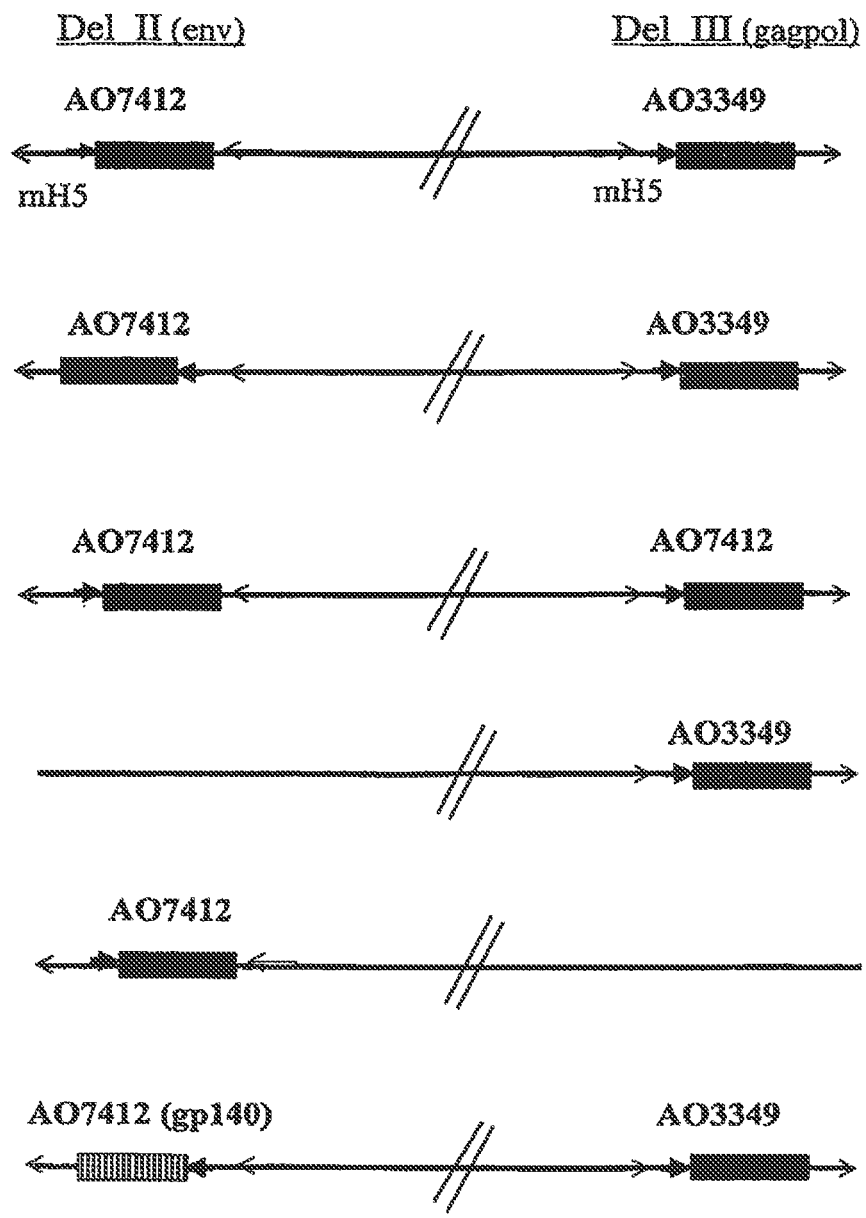
FIG. 18. Recombinant viruses expressing env and gagpol from Ugandan HIV-1 isolates.
Figure 19:
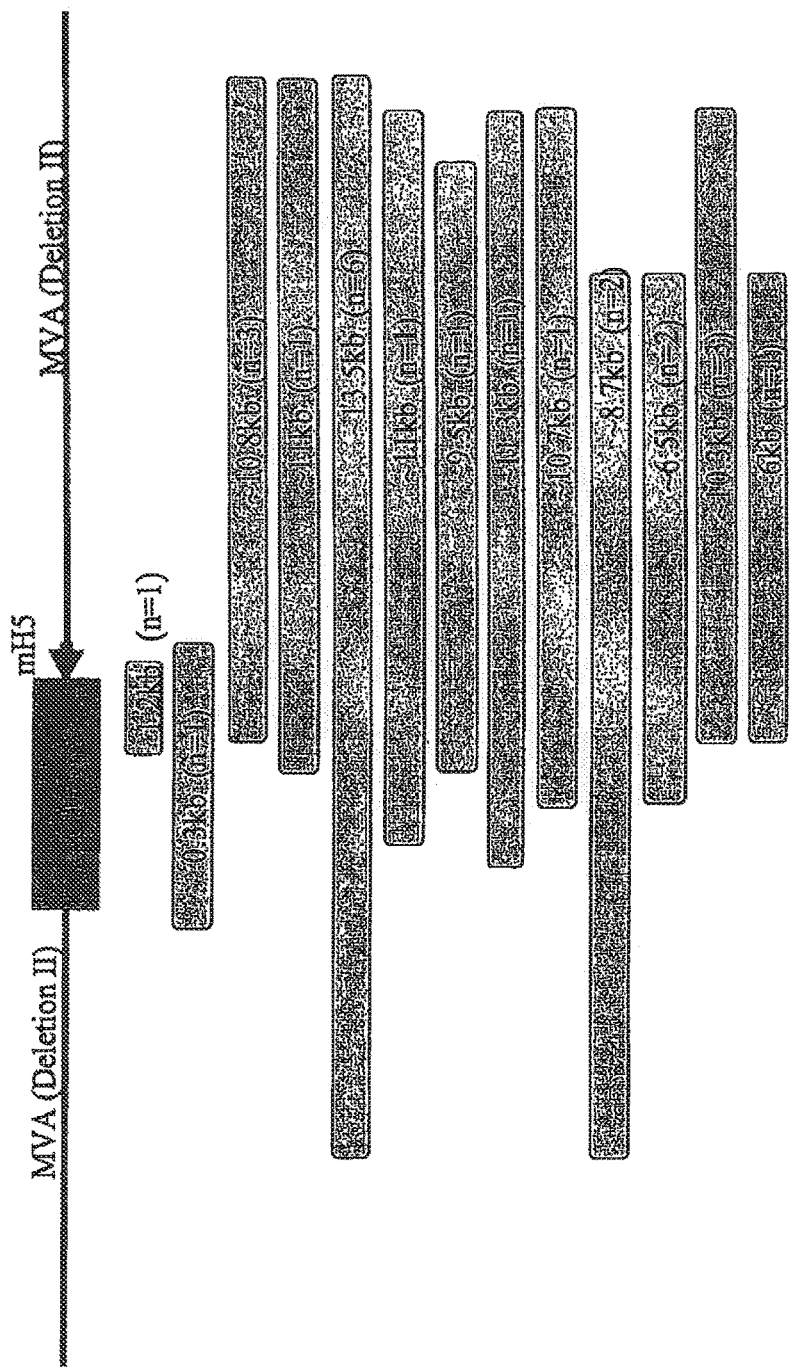
FIG. 19. MVA/UGD4a—analysis of non-staining env plaques.
Figure 20:
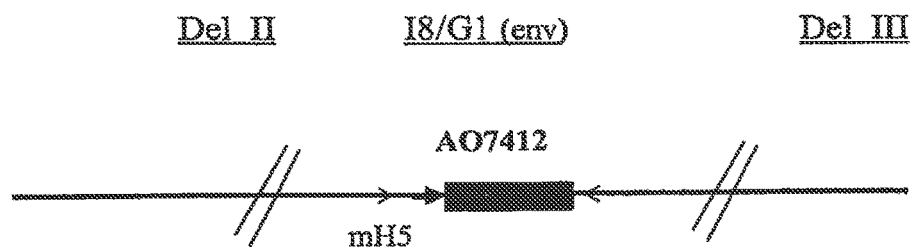
FIG. 20. Modification of UGD env gene in recombinant MVA.
Figure 21:
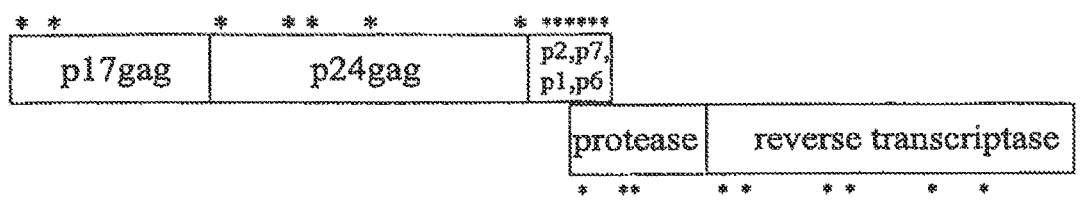
FIG. 21. MVA/UGD4b—analysis of non-staining gag plaques. *, location of runs of 4-6 G or C residues.
Figure 22:
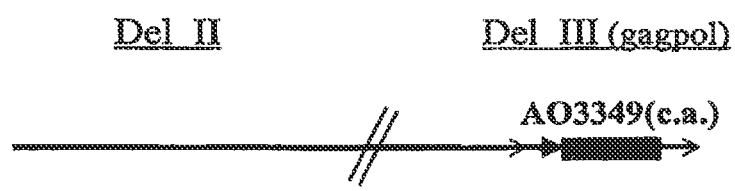
FIG. 22. Modification of UGD gagpol gene in recombinant MVA.
Figure 23:
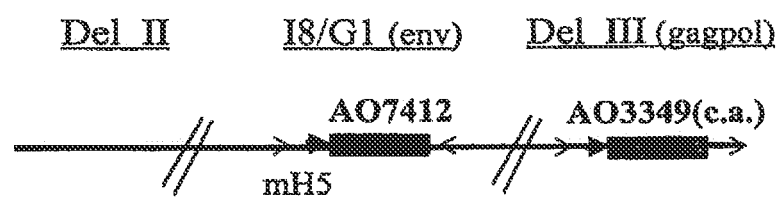
FIG. 23. Construction of stable recombinant MVA expressing UGD env and gagpol.
Figure 24:
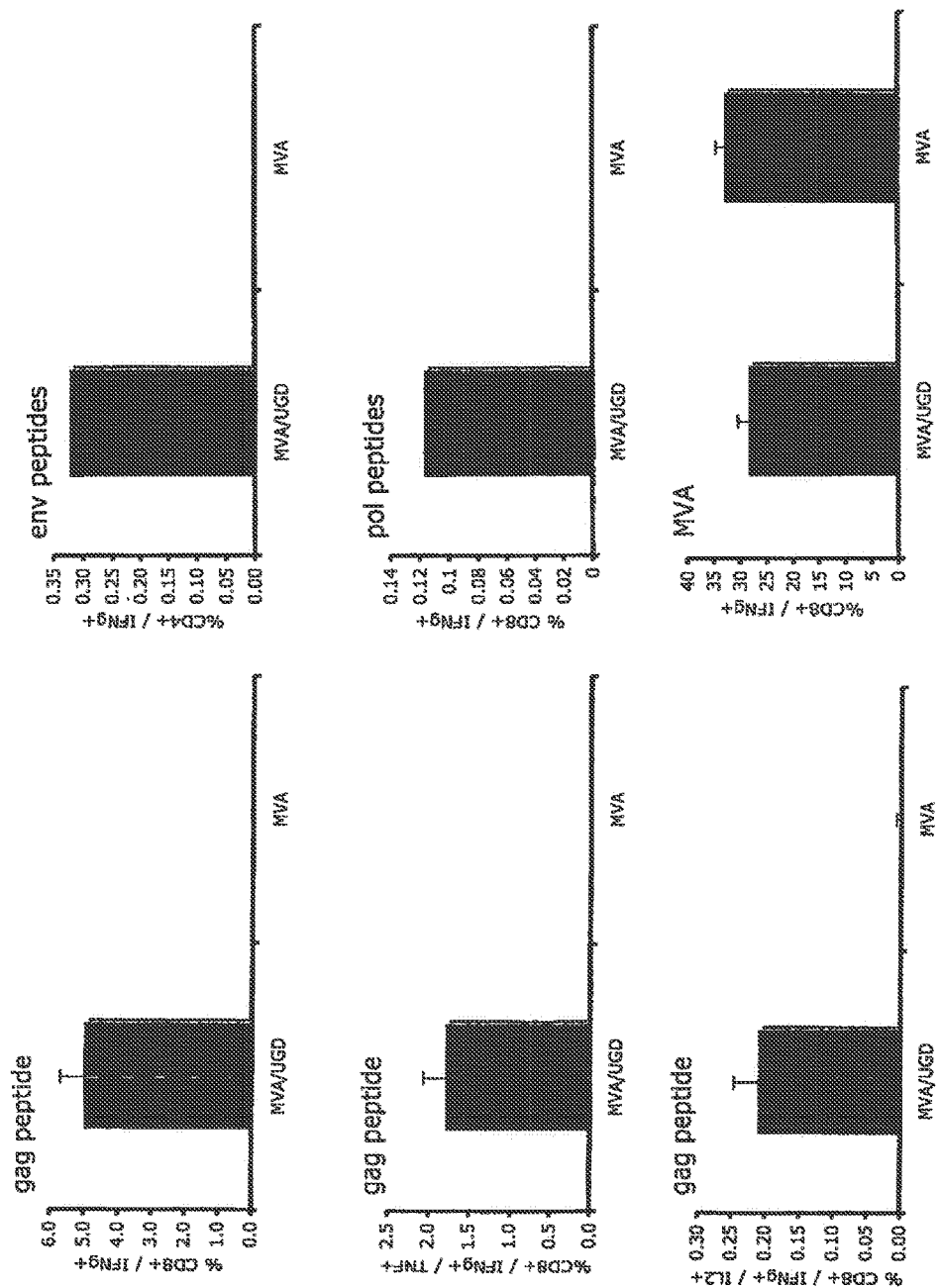
FIG. 24. Cellular responses elicited by MVA/UGD4d.
Figure 25:
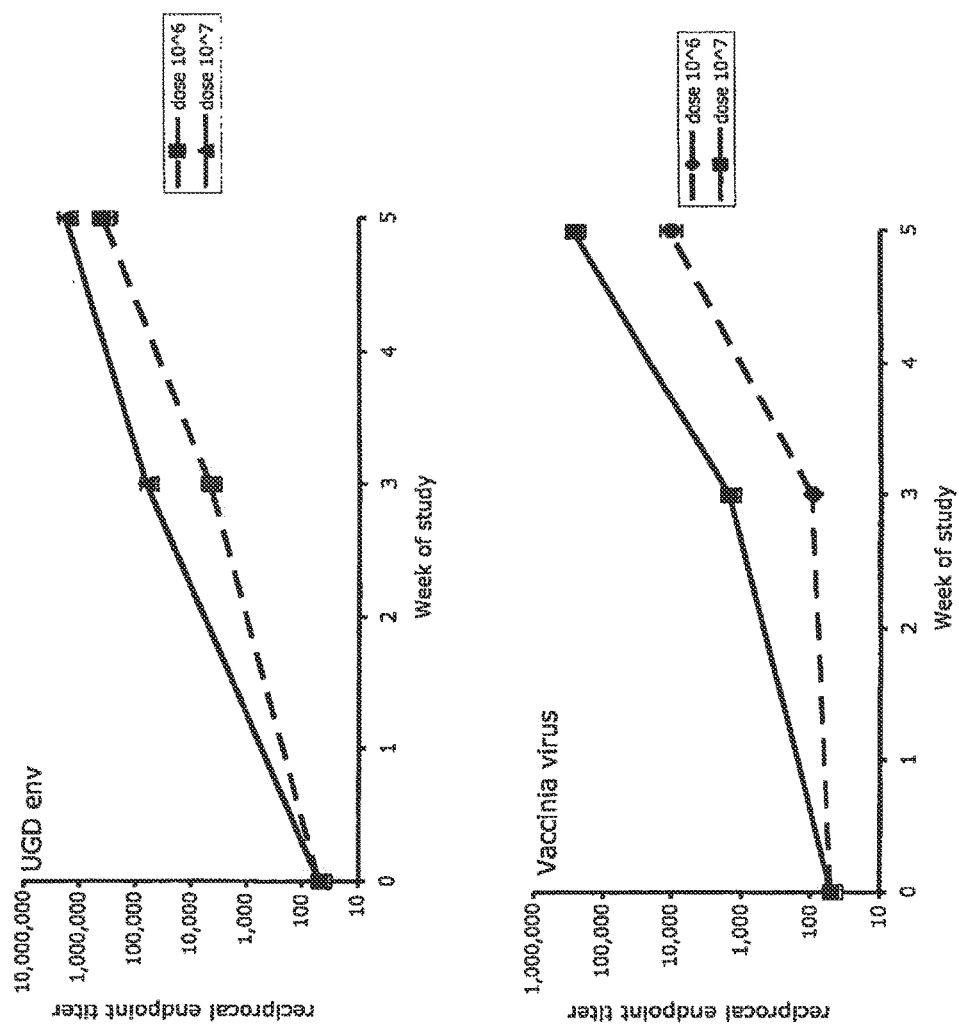
FIG. 25. Antibody responses elicited by MVA/UGD4d.

From selected plaque passages, clones were picked to analyze protein expression by Western blotting, PCR, and sequence analysis (FIG. 16). For Western blot analysis, T-24 and T-32 binding at the beginning and end of the clade A envelope, respectively, were used in order to determine if only partial or full length envelope was being made. Control viruses, marked c, are at the right of each blot. For the three viruses made in deletion II of MVA (FIGS. 16a, b, and c), only in FIG. 16c (i.e., gp140 clones), were all the clones expressing detectable protein in Western. This protein (as measured by T-32) was not truncated. When envelope was inserted into the essential gene site by vector I8/G1 (FIGS. 16d, e and f), again, only the gp140 envelope was being expressed in all clones and was not truncated. Although use of I8/G1 vector did not prevent mutations to the env sequence, it did prevent deletions which had been seen in envelope inserted into del II. (Note positive PCR products from all clones tested from I8/G1 vector, but negative PCR products from clones tested using del II vector.)

Expression of Env in Clade A/G Double Recombinant

Based on previous results with single env analysis, double recombinants expressing gagpol with either gp140 or the synthetic gp160 gene were made and tested for stability of env expression (FIG. 17). Five plaques were isolated from each as previously described, and passaged 7 times to analyze stability of env expression. At passage 7, the passaged plaques were immunostained with both T-43 and T-32 mAbs (which bind to gp120 and gp41, respectively). With T-43 mAb, one of five clones of recombinant expressing synthetic envelope consisted of only non-staining plaques. Subsequent T-32 staining of these plaques showed another plaque had truncated envelope expression. All passaged plaques from double recombinant containing gp140 envelope appeared stable by both T-43 and T-32 immunostaining. Titers were also 2 logs higher than with the other double recombinant. Thus a clade A/G double recombinant stably expressing envelope could only be made with gp140 envelope.

Recombinant Viruses Expressing Env and Gagpol from Ugandan HIV-1 Isolates

Recombinant MVA viruses expressing HIV-1 env and gagpol genes from Ugandan isolates AO7412 and AO3349 were constructed as shown in FIG. 18. Four to six independent isolates of each were serially passaged and both genes were found to be unstable whether expressed alone or in combination (Table 5). In contrast, expression of gp140 instead of membrane bound gp160 resulted in stability of the env gene after serial passage (FIG. 18 and Table 5).

MVA/UGD4a—Analysis of Non-Staining Env Plaques

To determine the mechanism of instability, 24 individual non-staining plaques (using Mab T-43) were isolated from passage 6 of MVA/UGD4a, amplified, and characterized. Two small deletions (1.2 and 0.3 kb) were identified by PCR amplification and DNA sequencing (FIG. 19). All other isolates contained very large deletions that extended into the flanking MVA. The approximate break-points for these deletions were identified using primer pairs from within the env gene or flanking MVA regions.

Modification of UGD Env Gene in Recombinant MVA

To ameliorate the problem of instability of the UGD env gene, the AO7412 env gene was inserted into MVA using the new vector, I8/G1, which directs recombination of a foreign gene between 2 essential vaccinia virus genes, I8 and G1 and uses the modified H5 promoter (FIG. 20). Four independent plaques were serially passaged and analyzed for env expression by immunostaining with Mabs T-43 and T-32 at passage 5. In all isolates, the gene was stable (Table 6).

MVA/UGD4b—Analysis of Non-Staining Gag Plaques

To determine the mechanism of instability of the gag gene, 8 individual non-staining plaques (using Mab 183-H12-5C-NIAID AIDS Repository) were picked from passage 6 of MVA/UGD4b, amplified, and the gagpol insert was sequenced (Table 7). In 7 isolates, an insertion or deletion of a single G residue at position 564-569 was found. In one isolate, a C residue was deleted from the sequence CCCC at position 530-534. Furthermore, non-staining plaques from high-passage stocks of MVA/KEA and MVA/TZC revealed a similar hot-spot for mutation, i.e., position 564-569. Examination of the full sequence of the UGD AO7412 gagpol gene demonstrated 22 runs of 4 or more G or C residues (FIG. 21).

Modification of UGD Gagpol Gene in Recombinant MVA

Since the mechanism of instability of the gagpol gene was primarily insertion or deletion of a single nucleotide within a run of 4-6 G or C residues, the strategy to improve the stability of this gene was to generate silent mutations at such sites. Thus, site-directed mutagenesis at 6 sites in p17 and p24 gag (Table 3) was employed. The resulting codon altered (c.a.) gene inserted into MVA at the same location, i.e., Deletion III, proved to be stable upon serial passage (FIG. 22 and Table 8).

Construction of Stable, Recombinant MVA Expressing UGD Env and Gagpol

A recombinant virus expressing the UGD env gene in the I8/G1 locus and the codon altered gagpol gene in Deletion III of MVA was constructed (FIG. 23). Serial passage demonstrated no instability of either gene. Furthermore, the level of protein expression and DNA sequence were unaltered during passage (Table 9).

CONCLUSIONS

Instability of env and gagpol inserts is attributed to the generation of point mutations and deletions and the growth advantage of non-expressing MVA mutants. Instability can generally be reduced by codon alteration and/or insertion into an essential region of the MVA genome (MVA/UGD4d) but env had to be altered in one case (MVA/65A/G).

Example 2

Immunogenicity of MVA/UGD4d in BALB/c Mice

Groups of 10 mice each were immunized by the intraperitoneal route with either $10^6$ or $10^7$ infectious units of MVA/UGD4d. Groups of 5 mice each were similarly immunized with parental MVA-1974. Mice were immunized at weeks 0 and 3 and bled at weeks 0, 3, and 5. Spleens were harvested at week 5.

Cellular responses were measured in fresh splenocytes by intracellular cytokine staining. Splenocytes were separately stimulated with the following: 1) immunodominant gag peptide (AMQMLKETI (SEQ ID NO: 6)), 2) env peptides (DTEVHNVWATHACVP (SEQ ID NO: 7) and QQQSN-LLRAIEAQQH (SEQ ID NO: 8)), 3) pol peptides (8 peptides with single amino acid variants of ELRQHLLR-WGLTT (SEQ ID NO: 9) and HGVYYDPSKDLIAE (SEQ ID NO: 10)), and 4) MVA.

Cells were stained for surface expression of CD4 and CD8 and then for intracellular expression of IFN-γ and either IL2 or TNF. As shown in FIG. 24, MVA/UGD4d elicited CD8/IFN-γ responses to the gag peptide, pol peptides, and MVA. The gag peptide responses were multifunctional, expressing both IFN-γ and either IL2 or TNF. Also, CD4/IFN-γ responses were elicited to the pool of env peptides.

Humoral responses were measured by ELISA (FIG. 25). Strong responses to UGD env were demonstrated at 3 weeks after one immunization and were boosted by the second immunization. In addition, strong vaccinia virus responses were elicited after one and two immunizations.

TABLE 3

MVA/UGD Nucleotide Changes Made to Eliminate Runs of G and C (HIV-1 isolate AO3349)

| Nucleotide # starting with ATG | Original Sequence | Modified Sequence |
|---|---|---|
| 28-32 | GGGGG | GGAGG |
| 70-74 | GGGGG | GGAGG |

TABLE 3-continued

MVA/UGD Nucleotide Changes Made to Eliminate Runs of G and C (HIV-1 isolate AO3349)

| Nucleotide # starting with ATG | Original Sequence | Modified Sequence |
|---|---|---|
| 408-411 | GGGG | GGGA |
| 530-533 | CCCC | CACC |
| 564-569 | GGGGGG | AGGAGG |
| 686-689 | GGGG | GAGG |

TABLE 6

Modification of UGD env Gene in Recombinant MVA

| | passage | % non-staining env | gag |
|---|---|---|---|
| UGD9 | 5 | 0.5 | |
| | 5 | | 0.4 |
| | 5 | | 0.0 |
| | 5 | | 0.5 |

TABLE 4

Stability of Recombinant MVAs

| | | | LVD seed | | passage 3/4 | | passage 6/7 | | passage 8/9 | | passage 10-13 | | vaccine lot | |
|---|---|---|---|---|---|---|---|---|---|---|---|---|---|---|
| Virus | Clade | Geographical origin | env | gag | env | gag | env | gag | env | gag | env | gag | env | gag |
| KEA5b | A | Kenya | <1 | <1 | 0.13 | 0.33 | 0.34 | 0.36 | | | 0.54 | 2.4 | 0.64 | 0.77 |
| 65A/G | A/G | Ivory Coast | <2 | <1 | 28 | 1 | 75 | | | | | | | |
| 62B | B | US | <1 | <1 | <1 | <1 | | | 6 | <1 | 10 | 1 | | |
| TZCa | C | Tanzania | <1 | <1 | <1 | <1 | 1.7 | 2.8 | 3.6 | 3.7 | | | | |
| 71C | C | India | <1 | <1 | <1 | 1 | <1 | 2 | 12 | 14 | | | | |
| UGD4a | D | Uganda | <1 | <1 | 3 | 0.28 | 6.7 | 6 | 12.2 | 17.4 | | | | |
| CMDR | E/A | Thailand | <1 | <1 | <1 | <1 | <1 | <1 | | | | | <1 | <1 |

TABLE 5

Recombinant Viruses Expressing env and gagpol from Ugandan HIV-1 isolates

| | passage | % non-staining env | gag |
|---|---|---|---|
| UGD4a | 9 | 12.2 | 17.4 |
| | 5 | 5.8 | 2.6 |
| | 5 | 2.7 | 17.6 |
| | 5 | 8.4 | 7.2 |
| | 5 | 11.4 | 8.0 |
| UGD4b | 6 | 1.5 | 17.0 |
| | 5 | 3.3 | 9.3 |
| | 5 | 3.7 | 8.3 |
| | 5 | 7.9 | 4.4 |
| | 5 | 15.2 | 5.0 |
| UGD1a | 4 | nd | 18.8 |
| | 4 | nd | 46.7 |
| | 4 | nd | 64.9 |
| | 4 | nd | 38.1 |
| | 5 | 7.9 | 44.8 |
| UGD gag3349 | 8 | | 36.6 |
| | 8 | | 25.4 |
| | 6 | | 22.9 |
| | 6 | | 33.1 |
| UGD env | 8 | 9.0 | |
| | 8 | 2.9 | |
| | 8 | 13.3 | |
| | 8 | 12.5 | |
| | 8 | 14.3 | |
| UGDgag/gp140 | 5 | 1.2 | 18.9 |
| | 5 | 2.3 | 17.6 |

TABLE 7

MVA/UGD4b- Analysis of Non-Staining gag Plaques

| | | | # individual plaques with mutation | | |
|---|---|---|---|---|---|
| gene | base # | sequence | MVA/UGD | MVA/KEA | MVA/TZC |
| p17 | 28 | GGGGG | | | |
| | 70 | GGGGG | | n = 1 | |
| p24 | 408 | GGGG | | | |
| | 530 | CCCC | n = 1 | | |
| | 564 | GGGGGG | n = 7 | n = 16 | n = 21 |
| | 686 | GGGG | | | |
| | 1050 | GGGGGG | | | |
| p7 | 1133 | GGGG | | | |
| p1 | 1320 | GGGG | | | |
| p6 | 1361 | CCCC | | | |
| | 1387 | GGGG | | | |
| | 1419 | GGGG | | | |
| | 1473 | CCCC | | | |
| Protease | 1494 | GGGGG | | | |
| RT | 1590 | GGGGG | | | |
| | 1599 | GGGGG | | | |
| | 2362 | GGGG | | | |
| | 2380 | GGGG | | | |
| | 2528 | GGGGG | | | |
| | 2596 | GGGG | | | |

TABLE 7-continued

MVA/UGD4b- Analysis of Non-Staining gag Plaques

| gene | base # | sequence | # individual plaques with mutation | | |
|---|---|---|---|---|---|
| | | | MVA/UGD | MVA/KEA | MVA/TZC |
| | 2893 | GGGG | | | |
| | 3001 | CCCC | | | |

TABLE 8

Modification of UGD gagpol Gene in Recombinant MVA

| | Passage | % non-staining | |
|---|---|---|---|
| | | env | gag |
| UGD gag (c.a.) | 6 | | 0.9 |
| | 6 | 0.0 | |
| | 6 | | 0.5 |

TABLE 9

Construction of Stable Recombinant MVA Expressing UGD env and gagpol

| | Passage | % non-staining | |
|---|---|---|---|
| | | env | gag |
| UGD4d | 11 | 0.0 | 0.7 |

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A plasmid vector comprising a cloning site flanked by:
   a) a first nucleic acid sequence derived from at least a portion of the 3' terminus of a first essential ORF from vaccinia virus genome; and
   b) a second nucleic acid sequence derived from at least a portion of the 3' terminus of a second essential ORF from vaccinia virus genome;

wherein the first and second essential ORFs are adjacent to one another in the vaccinia virus genome;

wherein the first and second essential ORFs are oriented 3' end-to-3' end in the vaccinia virus genome; and, wherein the first and second nucleic acid sequences are capable of effecting homologous recombination with the genome of an MVA virus.

2. The plasmid vector of claim 1, wherein the plasmid vector comprises a heterologous DNA sequence inserted between the first and second nucleic acid sequences.

3. The plasmid vector of claim 2, wherein the inserted heterologous DNA sequence is modified using a method comprising identifying runs of 4 or more contiguous guanine (G) or cytosine (C) residues in said insert, and making a silent mutation in said run so that the number of contiguous G or C nucleotide residues is reduced to less than four.

4. The plasmid vector of claim 1, wherein the vaccinia virus is selected from the group consisting of the MVA virus deposited at ATCC under accession number PTA-5095, the MVA virus having the sequence of GenBank AY603355, and the MVA virus having the sequence of GenBank accession number U94848.

5. The plasmid vector of claim 1, wherein the two adjacent ORFs are selected from the group consisting of: F17R-E1L, E8R-E9L, I8R-G1L, G2R-G4L, G6R-G7L, L2R-L3L, J4R-J5L, J6R-H1L, H2R-H3L, D1R-D2L, D10R-D11L, A5R-A6L, A8R-A9L, A11RA12L, and A18R-A19L, from GenBank accession number AY603355.

6. The plasmid vector of claim 1, wherein the plasmid vector comprises the sequence of pLW-73.

7. A method for producing a recombinant vaccinia virus comprising a heterologous DNA sequence inserted between two adjacent open reading frames (ORFs) of the vaccinia virus genome, wherein the two adjacent ORFs correspond to essential vaccinia virus ORFs, the method comprising:

a) transfecting a cell with the plasmid vector of claim 1 the heterologous DNA sequence, wherein the plasmid vector comprises the heterologous DNA sequence in the cloning site; and, b) infecting the transfected cell with a vaccinia virus.

8. The method of claim 7, wherein the vaccinia virus is selected from the group consisting of the MVA virus deposited at ATCC under accession number PTA-5095, the MVA virus having the sequence of GenBank accession number AY603355, and the MVA virus having the sequence of GenBank accession number U94848.

9. The method of claim 7, wherein the two adjacent ORFs are selected from the group consisting of: F17R-E1L, E8R-E9L, I8R-G1L, G2R-G4L, G6R-G7L, L2R-L3L, J4R-J5L, J6R-H1L, H2R-H3L, D1R-D2L, D10R-D11L, A5R-A6L, A8R-A9L, A11RA12L, and A18R-A19L, from GenBank accession number AY603355.

10. The method of claim 7, wherein the heterologous DNA sequence is modified using a method comprising identifying runs of 4 or more contiguous guanine (G) or cytosine (C) residues in said insert, and making a silent mutation in said run so that the number of contiguous G or C nucleotide residues is reduced to less than four.

11. A plasmid vector comprising an intergenic region (IGR) flanked by:

a) a first nucleic acid sequence derived from at least a portion of one end of a first essential ORF from a vaccinia virus; and, b) a second nucleic acid sequence derived from at least a portion of one end of a second essential ORF from a vaccinia virus;

wherein the first and second essential ORFs are adjacent to one another in the vaccinia virus genome;

wherein the end of the first essential ORF and the end of second essential ORF are proximal to one another in the vaccinia virus genome;

wherein the first and second nucleic acid sequences are capable of homologous recombination with an MVA virus genome; and, wherein the IGR comprises the IGR of the first and second essential ORFs in the vaccinia virus genome.

12. The plasmid vector of claim 11, wherein the plasmid vector comprises a heterologous DNA sequence in the IGR.

13. The plasmid vector of claim 12, wherein the inserted heterologous DNA sequence is modified using a method comprising identifying runs of 4 or more contiguous guanine (G) or cytosine (C) residues in said insert, and making a silent mutation in said run so that the number of contiguous G or C nucleotide residues is reduced to less than four.

14. The plasmid vector of claim 11, wherein the vaccinia virus is selected from the group consisting of the MVA virus deposited at ATCC under accession number PTA-5095, the MVA virus having the sequence of GenBank AY603355, and the MVA virus having the sequence of GenBank accession number U94848.

15. The plasmid vector of claim 11, wherein the two adjacent ORFs are selected from the group consisting of: F12L-F13L, F17R-E1L, E1L-E2L, E9L-E10R, I1L-I2L, I2L-I3L, I6L-I7L, I7L-I8R, I8R-G1L, G1L-G3L, G3L-G2R, G2R-G4L, G4L-G5R, G5R-G5.5R, G5.5R-G6R, G6R-G7L, G9R-L1R, L4R-L5R, L5R-J1R, J3R-J4R, J6R-H1L, H1L-H2R, H3L-H4L, H5R-H6R, D1R-D2L, D2L-D3R, D3R-D4R, D5R-D6R, D9R-D10R, A1L-A2L, A2L-A2.5LA5R-A6L, A8R-A9L, A9L-A10L, A10L-A11R, A14L-A14.5L, A14.5L-A15L, A15L-A16L, A16L-A17L, A17L-A18R, A18R-A19L, A19L-A21L, A21L-A20R, A20R-A22R, A28L-A29L, and A29L-A30L from GenBank accession number AY603355.

16. The plasmid vector of claim 11, wherein the plasmid vector comprises the sequence of pLW-73.

* * * * *

```
                        SEQUENCE LISTING

<160> NUMBER OF SEQ ID NOS: 10

<210> SEQ ID NO 1
<211> LENGTH: 4
<212> TYPE: PRT
<213> ORGANISM: Human immunodeficiency virus type 1
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Tyr Xaa Xaa Leu
1

<210> SEQ ID NO 2
<211> LENGTH: 5044
<212> TYPE: DNA
<213> ORGANISM: Artificial Sequence
<220> FEATURE:
<223> OTHER INFORMATION: pLW-73 Plasmid DNA, top strand

<400> SEQUENCE: 2
gaattccctg ggacatacgt atatttctat gatctgtctt atatgaagtc tatacagcga      60
atagattcag aatttctaca taattatata ttgtacgcta ataagtttaa tctaacactc     120
cccgaagatt tgtttataat ccctacaaat ttggatattc tatggcgtac aaaggaatat     180
atagactcgt tcgatattag tacagaaaca tggaataaat tattatccaa ttattatatg     240
aagatgatag agtatgctaa actttatgta ctaagtccta ttctcgctga ggagttggat     300
aattttgaga ggacgggaga attaactagt attgtacaag aagccatttt atctctaaat     360
ttacgaatta agattttaaa ttttaaacat aaagatgatg atacgtatat acacttttgt     420
aaaatattat tcggtgtcta taacggaaca aacgctacta tatattatca tagacctcta     480
acgggatata tgaatatgat ttcagatact atatttgttc ctgtagataa taactaaggc     540
gcgcctttca ttttgttttt ttctatgcta taaatggtga gcaagggcga ggagctgttc     600
accggggtgg tgcccatcct ggtcgagctg gacgcgacg taaacggcca caagttcagc     660
gtgtccggcg agggcgaggg cgatgccacc tacggcaagc tgaccctgaa gttcatctgc     720
```

```
accaccggca agctgcccgt gccctggccc accctcgtga ccaccctgac ctacggcgtg      780
cagtgcttca gccgctaccc cgaccacatg aagcagcacg acttcttcaa gtccgccatg      840
cccgaaggct acgtccagga gcgcaccatc ttcttcaagg acgacggcaa ctacaagacc      900
cgcgccgagg tgaagttcga gggcgacacc ctggtgaacc gcatcgagct gaagggcatc      960
gacttcaagg aggacggcaa catcctgggg cacaagctgg agtacaacta caacagccac     1020
aacgtctata tcatggccga caagcagaag aacggcatca aggtgaactt caagatccgc     1080
cacaacatcg aggacggcag cgtgcagctc gccgaccact accagcagaa cacccccatc     1140
ggcgacggcc ccgtgctgct gcccgacaac cactacctga gcacccagtc cgccctgagc     1200
aaagacccca acgagaagcg cgatcacatg gtcctgctgg agttcgtgac cgccgccggg     1260
atcactctcg gcatgcacga gctgtacaag taagagctcg gaggcgggag aattaactag     1320
tattgtacaa gaagccattt tatctctaaa tttacgaatt aagattttaa attttaaaca     1380
taaagatgat gatacgtata tacacttttg taaaatatta ttcggtgtct ataacggaac     1440
aaacgctact atatattatc atagacctct aacgggatat atgaatatga tttcagatac     1500
tatatttgtt cctgtagata taactaact cgaggccgct ggtacccaac ctaaaaattg     1560
aaaataaata caaaggttct tgagggttgt gttaaattga aagcgagaaa taatcataaa     1620
taagcccggg gatcctctag agtcgacctg cagtcaaact ctaatgacca catctttttt     1680
tagagatgaa aaattttcca catctccttt tgtagacacg actaaacatt ttgcagaaaa     1740
aagtttatta gtgtttagat aatcgtatac ttcatcagtg tagatagtaa atgtgaacag     1800
ataaaaggta ttcttgctca atagattggt aaattccata gaatatatta atcctttctt     1860
cttgagatcc cacatcattt caaccagaga cgttttatcc aatgatttac ctcgtactat     1920
accacataca aaactagatt ttgcagtgac gtcgtatctg gtattcctac caaacaaaat     1980
tttactttta gttcttttag aaaattctaa ggtagaatct ctatttgcca atatgtcatc     2040
tatgaaatta ccactagcaa aaaatgatag aaatatatat tgatacatcg cagctggttt     2100
tgatctacta tactttaaaa acgaatcaga ttccataatt gcctgtatat catcagctga     2160
aaaactatgt tttacacgta ttccttcggc atttcttttt aatgatatat cttgtttaga     2220
caatgataaa gttatcatgt ccatgagaga cgcgtctccg tatcgtataa atatttcatt     2280
agatgttaga cgcttcatta ggggtatact tctataaggt ttcttaatca gtccatcatt     2340
ggttgcgtca agaacaagct tgtctcccta tagtgagtcg tattagagct ggcgtaatc      2400 atggtcatag ctgtttcctg tgtgaaattg ttatccgctc acaattccac acaacatacg     2460
agccggaagc ataaagtgta aagcctgggg tgcctaatga gtgagctaac tcacattaat     2520
tgcgttgcgc tcactgcccg ctttcgagtc gggaaacctg tcgtgccagc tgcattaatg     2580
aatcggccaa cgcgcgggga gaggcggttt gcgtattggg cgctcttccg cttcctcgct     2640
cactgactcg ctgcgctcgg tcgttcggct gcggcgagcg gtatcagctc actcaaaggc     2700
ggtaatacgg ttatccacag aatcagggga taacgcagga aagaacatgt gagcaaaagg     2760
ccagcaaaag gccaggaacc gtaaaaaggc cgcgttgctg gcgtttttcg ataggctccg     2820
cccccctgac gagcatcaca aaaatcgacg ctcaagtcag aggtggcgaa acccgacagg     2880
actataaaga taccaggcgt ttccccctgg aagctccctc gtgcgctctc ctgttccgac     2940
cctgccgctt accggatacc tgtccgcctt tctcccttcg ggaagcgtgg cgctttctca     3000
tagctcacgc tgtaggtatc tcagttcggt gtaggtcgtt cgctccaagc tgggctgtgt     3060
gcacgaaccc cccgttcagc ccgaccgctg cgccttatcc ggtaactatc gtcttgagtc     3120
```

```
caacccggta agacacgact tatcgccact ggcagcagcc actggtaaca ggattagcag    3180
agcgaggtat gtaggcggtg ctacagagtt cttgaagtgg tggcctaact acggctacac    3240
tagaaggaca gtatttggta tctgcgctct gctgaagcca gttaccttcg gaaaaagagt    3300
tggtagctct tgatccggca aacaaaccac cgctggtagc ggtggttttt ttgtttgcaa    3360
gcagcagatt acgcgcagaa aaaaaggatc tcaagaagat cctttgatct tttctacggg    3420
gtctgacgct cagtggaacg aaaactcacg ttaagggatt ttggtcatga gattatcaaa    3480
aaggatcttc acctagatcc ttttaaatta aaaatgaagt tttaaatcaa tctaaagtat    3540
atatgagtaa acttggtctg acagttacca atgcttaatc agtgaggcac ctatctcagc    3600
gatctgtcta tttcgttcat ccatagttgc ctgactcccc gtcgtgtaga taactacgat    3660
acgggagggc ttaccatctg gccccagtgc tgcaatgata ccgcgagacc cacgctcacc    3720
ggctccagat ttatcagcaa taaaccagcc agccggaagg gccgagcgca gaagtggtcc    3780
tgcaacttta tccgcctcca tccagtctat taattgttgc cgggaagcta gagtaagtag    3840
ttcgccagtt aatagtttgc gcaacgttgt tgccattgct acaggcatcg tggtgtcacg    3900
ctcgtcgttt ggtatggctt cattcagctc cggttcccaa cgatcaaggc gagttacatg    3960
atcccccatg ttgtgcaaaa aagcggttag ctccttcggt cctccgatcg ttgtcagaag    4020
taagttggcc gcagtgttat cactcatggt tatggcagca ctgcataatt ctcttactgt    4080
catgccatcc gtaagatgct tttctgtgac tggtgagtac tcaaccaagt cattctgaga    4140
atagtgtatg cggcgaccga gttgctcttg cccggcgtca atacgggata ataccgcgcc    4200
acatagcaga actttaaaag tgctcatcat tggaaaacgt tcttcggggc gaaaactctc    4260
aaggatctta ccgctgttga gatccagttc gatgtaaccc actcgtgcac ccaactgatc    4320
ttcagcatct tttactttca ccagcgtttc tgggtgagca aaaacaggaa ggcaaaatgc    4380
cgcaaaaaag ggaataaggg cgacacggaa atgttgaata ctcatactct tcctttttca    4440
atattattga agcatttatc agggttattg tctcatgagc ggatacatat ttgaatgtat    4500
ttagaaaaat aaacaaatag gggttccgcg cacatttccc cgaaaagtgc cacctgacgt    4560
ctaagaaacc attattatca tgacattaac ctataaaaat aggcgtatca cgaggccctt    4620
tcgtctcgcg cgtttcggtg atgacggtga aaacctctga cacatgcagc tcccggagac    4680
ggtcacagct tgtctgtaag cggatgccgg gagcagacaa gcccgtcagg gcgcgtcagc    4740
gggtgttggc gggtgtcggg gctggcttaa ctatgcggca tcagagcaga ttgtactgag    4800
agtgcaccat atgcggtgtg aaataccgca cagatgcgta aggagaaaat accgcatcag    4860
gcgccattcg ccattcaggc tgcgcaactg ttgggaaggg cgatcggtgc gggcctcttc    4920
gctattacgc cagctggcga aggggggatg tgctgcaagg cgattaagtt gggtaacgcc    4980
agggttttcc cagtcacgac gttgtaaaac gacggccagt gaattggatt taggtgacac    5040
tata                                                                5044
```

<210> SEQ ID NO 3
<211> LENGTH: 5044
<212> TYPE: DNA
<213> ORGANISM: Artificial Sequence
<220> FEATURE:
<223> OTHER INFORMATION: pLW-73 Plasmid DNA, bottom strand, 5'-3'

<400> SEQUENCE: 3

```
tatagtgtca cctaaatcca attcactggc cgtcgtttta caacgtcgtg actgggaaaa      60
```

-continued

```
ccctggcgtt acccaactta atcgccttgc agcacatccc cctttcgcca gctggcgtaa      120
tagcgaagag gcccgcaccg atcgcccttc ccaacagttg cgcagcctga atggcgaatg      180
gcgcctgatg cggtattttc tccttacgca tctgtgcggt atttcacacc gcatatggtg      240
cactctcagt acaatctgct ctgatgccgc atagttaagc cagccccgac acccgccaac      300
acccgctgac gcgccctgac gggcttgtct gctcccggca tccgcttaca gacaagctgt      360
gaccgtctcc gggagctgca tgtgtcagag gttttcaccg tcatcaccga aacgcgcgag      420
acgaaagggc ctcgtgatac gcctattttt ataggttaat gtcatgataa taatggtttc      480
ttagacgtca ggtggcactt tcggggaaa tgtgcgcgga acccctattt gtttattttt       540
ctaaatacat tcaaatatgt atccgctcat gagacaataa ccctgataaa tgcttcaata     600
atattgaaaa aggaagagta tgagtattca acatttccgt gtcgcccctta ttcccttttt     660 tgcggcattt tgccttcctg ttttttgctca cccagaaacg ctggtgaaag taaaagatgc     720
tgaagatcag ttgggtgcac gagtgggtta catcgaactg gatctcaaca gcggtaagat     780
ccttgagagt tttcgccccg aagaacgttt tccaatgatg agcacttta aagttctgct      840 atgtggcgcg gtattatccc gtattgacgc cgggcaagag caactcggtc gccgcataca     900
ctattctcag aatgacttgg ttgagtactc accagtcaca gaaaagcatc ttacggatgg     960
catgacagta agagaattat gcagtgctgc cataaccatg agtgataaca ctgcggccaa    1020
cttacttctg acaacgatcg gaggaccgaa ggagctaacc gcttttttgc acaacatggg    1080
ggatcatgta actcgccttg atcgttggga accggagctg aatgaagcca taccaaacga    1140
cgagcgtgac accacgatgc ctgtagcaat ggcaacaacg ttgcgcaaac tattaactgg    1200
cgaactactt actctagctt cccggcaaca attaatagac tggatggagg cggataaagt    1260
tgcaggacca cttctgcgct cggcccttcc ggctggctgg tttattgctg ataaatctgg    1320
agccggtgag cgtgggtctc gcggtatcat tgcagcactg gggccagatg gtaagccctc    1380
ccgtatcgta gttatctaca cgacggggag tcaggcaact atggatgaac gaaatagaca    1440
gatcgctgag ataggtgcct cactgattaa gcattggtaa ctgtcagacc aagtttactc    1500
atatatactt tagattgatt taaaacttca ttttttaattt aaaaggatct aggtgaagat    1560 ccttttttgat aatctcatga ccaaaatccc ttaacgtgag ttttcgttcc actgagcgtc    1620
agaccccgta gaaaagatca aaggatcttc ttgagatcct ttttttctgc gcgtaatctg    1680
ctgcttgcaa acaaaaaaac caccgctacc agcggtggtt tgtttgccgg atcaagagct    1740
accaactctt tttccgaagg taactggctt cagcagagcg cagataccaa atactgtcct    1800
tctagtgtag ccgtagttag gccaccactt caagaactct gtagcaccgc ctacatacct    1860
cgctctgcta atcctgttac cagtggctgc tgccagtggc gataagtcgt gtcttaccgg    1920
gttggactca agacgatagt taccggataa ggcgcagcgg tcgggctgaa cggggggttc    1980
gtgcacacag cccagcttgg agcgaacgac ctacaccgaa ctgagatacc tacagcgtga    2040
gctatgagaa agcgccacgc ttcccgaagg gagaaaggcg gacaggtatc cggtaagcgg    2100
cagggtcgga acaggagagc gcacgaggga gcttccaggg ggaaacgcct ggtatcttta    2160
tagtcctgtc gggtttcgcc acctctgact tgagcgtcga ttttgtgat gctcgtcagg    2220 ggggcggagc ctatcgaaaa acgccagcaa cgcggccttt ttacggttcc tggccttttg    2280
ctggcctttt gctcacatgt tctttcctgc gttatcccct gattctgtgg ataaccgtat    2340
taccgccttt gagtgagctg ataccgctcg ccgcagccga acgaccgagc gcagcgagtc    2400
agtgagcgag gaagcggaag agcgcccaat acgcaaaccg cctctccccg cgcgttggcc    2460
```

```
gattcattaa tgcagctggc acgacaggtt tcccgactcg aaagcgggca gtgagcgcaa    2520
cgcaattaat gtgagttagc tcactcatta ggcaccccag gctttacact ttatgcttcc    2580
ggctcgtatg ttgtgtggaa ttgtgagcgg ataacaattt cacacaggaa acagctatga    2640
ccatgattac gccaagctct aatacgactc actatagggg acaagcttg ttcttgacgc     2700 aaccaatgat ggactgatta agaaaccttaa tagaagtata cccctaatga agcgtctaac   2760
atctaatgaa atatttatac gatacggaga cgcgtctctc atggacatga taactttatc    2820
attgtctaaa caagatatat cattaaaaag aaatgccgaa ggaatacgtg taaaacatag    2880
tttttcagct gatgatatac aggcaattat ggaatctgat tcgttttaa agtatagtag     2940 atcaaaacca gctgcgatgt atcaatatat atttctatca tttttgcta gtggtaattc     3000 catagatgac atattggcaa atagagattc taccttagaa ttttctaaaa gaactaaaag    3060
taaaattttg tttggtagga ataccagata cgacgtcact gcaaaatcta gttttgtatg    3120
tggtatagta cgaggtaaat cattggataa aacgtctctg gttgaaatga tgtgggatct    3180
caagaagaaa ggattaatat attctatgga atttaccaat ctattgagca agaatacctt    3240
ttatctgttc acatttacta tctacactga tgaagtatac gattatctaa acactaataa    3300
acttttttct gcaaaatgtt tagtcgtgtc tacaaaagga gatgtggaaa attttttcatc  3360 tctaaaaaaa gatgtggtca ttagagtttg actgcaggtc gactctagag gatcccggg    3420 cttatttatg attatttctc gctttcaatt taacacaacc ctcaagaacc tttgtattta    3480
ttttcaattt ttaggttggg taccagcggc ctcgagttag ttattatcta caggaacaaa    3540
tatagtatct gaaatcatat tcatatatcc cgttagaggt ctatgataat atatagtagc    3600
gtttgttccg ttatagacac cgaataatat tttacaaaag tgtatatacg tatcatcatc    3660
tttatgttta aaatttaaaa tcttaattcg taaatttaga gataaaatgg cttcttgtac    3720
aatactagtt aattctcccg tcctcgagct cttacttgta cagctcgtgc atgccgagag    3780
tgatcccggc ggcggtcacg aactccagca ggaccatgtg atcgcgcttc tcgttggggt    3840
ctttgctcag gcggactgg gtgctcaggt agtggttgtc gggcagcagc acggggccgt     3900
cgccgatggg ggtgttctgc tggtagtggt cggcgagctg cacgctgccg tcctcgatgt    3960
tgtggcggat cttgaagttc accttgatgc cgttcttctg cttgtcggcc atgatataga    4020
cgttgtggct gttgtagttg tactccagct tgtgccccag gatgttgccg tcctccttga    4080
agtcgatgcc cttcagctcg atgcggttca ccagggtgtc gccctcgaac ttcacctcgg    4140
cgcgggtctt gtagttgccg tcgtccttga agaagatggt gcgctcctgg acgtagcctt    4200
cgggcatggc ggacttgaag aagtcgtgct gcttcatgtg gtcggggtag cggctgaagc    4260
actgcacgcc gtaggtcagg gtggtcacga gggtgggcca gggcacgggc agcttgccgg    4320
tggtgcagat gaacttcagg gtcagcttgc cgtaggtggc atcgccctcg ccctcgccgg    4380
acacgctgaa cttgtggccg tttacgtcgc cgtccagctc gaccaggatg gcaccaccc     4440 cggtgaacag ctcctcgccc ttgctcacca tttatagcat agaaaaaaac aaaatgaaag    4500
gcgcgcctta gttattatct acaggaacaa atatagtatc tgaaatcata ttcatatatc    4560
ccgttagagg tctatgataa tatatagtag cgttgttcc gttatagaca ccgaataata   4620
ttttacaaaa gtgtatatac gtatcatcat ctttatgttt aaaatttaaa atcttaattc    4680
gtaaatttag agataaaatg gcttcttgta caatactagt taattctccc gtcctctcaa    4740
aattatccaa ctccctcagcg agaataggac ttagtacata agtttagca tactctatca    4800
```

-continued

```
tcttcatata ataattggat aataatttat tccatgtttc tgtactaata tcgaacgagt    4860
ctatatattc ctttgtacgc catagaatat ccaaatttgt agggattata acaaatctt     4920 cggggagtgt tagattaaac ttattagcgt acaatatata attatgtaga aattctgaat    4980
ctattcgctg tatagacttc atataagaca gatcatagaa atatacgtat gtcccaggga    5040
attc                                                                  5044
```

<210> SEQ ID NO 4
<211> LENGTH: 2214
<212> TYPE: DNA
<213> ORGANISM: Human Immunodeficiency virus type 1, env

<400> SEQUENCE: 4

```
atgagagtga gggagacagt gaggaattat cagcacttgt ggagatgggg catcatgctc      60
cttgggatgt taatgatatg tagtgctgca gaccagctgt gggtcacagt gtattatggg     120
gtacctgtgt ggaaagaagc aaccactact ctattttgtg catcagatgc taaagcacat     180
aaagcagagg cacataatat ctgggctaca catgcctgtg taccaacaga ccccaatcca     240
cgagaaataa tactaggaaa tgtcacagaa actttaaaca tgtggaagaa taacatggta     300
gagcagatgc atgaggatat aatcagttta tgggatcaaa gtctaaaacc atgtgtaaaa     360
ttaaccccac tctgtgttac tttaaactgc actacatatt ggaatggaac tttacagggg     420
aatgaaacta aagggaagaa tagaagtgac ataatgacat gctctttcaa tataaccaca     480
gaaataagag gtagaaagaa gcaagaaact gcacttttct ataaacttga tgtggtacca     540
ctagaggata aggatagtaa taagactacc aactatagca gctatagatt aataaattgc     600
aatacctcag tcgtgacaca ggcgtgtcca aaagtaacct ttgagccaat tcccatacat     660
tattgtgccc cagctggatt tgcgattctg aaatgtaata taagacgtt caatggaacg     720 ggtccatgca aaatgtcag cacagtacag tgtacacatg gaattaggcc agtagtgtca     780
actcaactgt tgttgaatgg cagtctagca gaagaagaga taataattag atctgaaaat     840
atcacaaata tgcaaaaac cataatagta cagcttaatg agtctgtaac aattgattgc     900
ataaggccca caacaatac aagaaaaagt atacgcatag gaccagggca agcactctat     960
acaacagaca taatagggaa tataagacaa gcacattgta atgttagtaa agtaaaatgg    1020
ggaagaatgt taaaagggt agctgaaaaa ttaaaagacc ttcttaacca gacaaagaac    1080
ataacttttg aaccatcctc aggagggggac ccagaaatta caacacacag ctttaattgt    1140
ggaggggaat tcttctactg caatacatca ggactatttta atgggagtct gcttaatgag    1200
cagtttaatg agacatcaaa tgatactctc acactccaat gcagaataaa acaaattata    1260
aacatgtggc aaggagtagg aaaagcaatg tatgcccctc ccattgcagg accaatcagc    1320
tgttcatcaa atattacagg actattgttg acaagagatg gtggtaatac tggtaatgat    1380
tcagagatct tcagacctgg agggggagat atgagagaca attggagaag tgaattatac    1440
aaatataaag tagtaagaat tgaaccaatg ggtctagcac ccaccagggc aaaaagaaga    1500
gtggtggaaa gagaaaaaag agcaataggga ctgggagcta tgttccttgg gttcttggga    1560
gcggcaggaa gcacgatggg cgcagcgtca ctgacgctga cggtacaggc cagacagtta    1620
ttgtctggta tagtgcaaca gcaaaacaat ttgctgagag ctatagaggc gcaacagcat    1680
ctgttgcaac tcacagtctg ggcattaaaa cagctccagg caagagtcct ggctatggaa    1740
agctacctaa aggatcaaca gctcctagga atttggggtt gctctggaaa acacatttgc    1800
accactactg tgccctggaa ctctacctgg agtaatagat ctgtagagga gatttggaat    1860
```

-continued

| | |
|---|---|
| aatatgacct ggatgcagtg ggaaagagaa attgagaatt acacaggttt aatatacacc | 1920 |
| ttaattgaag aatcgcaaac ccagcaagaa aagaatgaac aagaactatt gcaattggat | 1980 |
| aaatgggcaa gtttgtggaa ttggtttagt ataacaaaat ggctgtggta tataaaaata | 2040 |
| ttcataatga tagtaggagg cttaataggt ttaagaatag tttttgctgt gctttcttta | 2100 |
| gtaaatagag ttaggcaggg atattcacct ctgtcttttc agaccctcct cccagccccg | 2160 |
| aggggacccg acaggcccga aggaatagaa gaagaaggtg gagagcaagg ctaa | 2214 |

<210> SEQ ID NO 5
<211> LENGTH: 3068
<212> TYPE: DNA
<213> ORGANISM: Human Immunodeficiency virus type 1, gagpol

<400> SEQUENCE: 5

| | |
|---|---|
| atgggtgcga gagcgtcagt attaagcgga ggaaaattag atgaatggga aaaaattcgg | 60 |
| ttacggccag gaggaaacaa aaaatataga ttaaaacatt tagtatgggc aagcagggag | 120 |
| ctagaacgat ttgcacttaa tcctggtctt ttagaaacat cagaaggctg tagacaaata | 180 |
| atagaacagc tacaaccatc tattcagaca ggatcagagg aacttaaatc attacataat | 240 |
| acagtagtaa ccctctattg tgtacatgaa aggataaagg tagcagatac caaggaagct | 300 |
| ttagataaga taaggaagaa acaaaccaaa agtaagaaaa agcacagca agcaacagct | 360 |
| gacagcagcc aggtcagcca aaattatcct atagtacaaa acctacaggg acaaatggta | 420 |
| caccagtcct tatcacctag gactttgaat gcatgggtaa agtaatagaa gagaaggct | 480 |
| ttcagcccag aagtaatacc catgttttca gcattatcag aaggagccac caacagat | 540 |
| ttaaacacca tgctaaacac agtaggagga catcaagcag ccatgcaaat gttaaaagag | 600 |
| actatcaatg aggaagctgc agaatgggat aggctacatc cagtgcctgc agggcctgtt | 660 |
| gcaccaggcc aaatgagaga accaagagga agtgatatag caggaactac cagtacccttt | 720 |
| caggaacaaa taggatggat gacaagcaat ccacctatcc cagtaggaga atctataaaa | 780 |
| agatggataa tcctaggatt aaataaaata gtaagaatgt atagccctgt cagcattttg | 840 |
| gacataagac aaggaccaaa ggaacccttt agagactatg tagatcggtt ctataaaact | 900 |
| ctacgagccg agcaagcttc acaggatgta aaaaattgga tgactgaaac cttgttagtc | 960 |
| caaaatgcga atccagattg taaaactatc ttaaaagcat tgggaccagc ggctacatta | 1020 |
| gaagaaatga tgacagcatg tcagggagtg gggggaccca gtcataaagc aagagttttg | 1080 |
| gctgaggcaa tgagccaagc atcaaacaca atgctgtta taatgatgca gaggggcaat | 1140 |
| ttcaagggca agaaaatcat taagtgtttc aactgtggca agaaggaca cctagcaaaa | 1200 |
| aattgtaggg ctcctaggaa aagaggctgt tggaaatgtg gaaggaaggg caccaaatg | 1260 |
| aaagattgta atgaaagaca ggctaatttt ttagggagaa tttggccttc ccacaagggg | 1320 |
| aggccaggga atttccttca gagcagacca gagccaacag ccccaccagc agagagcttc | 1380 |
| gggtttgggg aagagataac accctcccag aaacaggagg ggaaagagga gctgtatcct | 1440 |
| tcagcctccc tcaaatcact ctttggcaac gaccctagt cacaataaaa ataggggac | 1500 |
| agctaaagga agctctatta gatacaggag cagatgatac agtagtagaa gaatgaatt | 1560 |
| tgccaggaaa atggaaacca aaaatgatag ggggaattgg gggctttatc aaagtaagac | 1620 |
| agtatgatca atactcgta gaaatctatg gatataaggc tacaggtaca gtattagtag | 1680 |
| gacctacacc tgtcaacata attggaagaa atttgttgac tcagattggt tgcactttaa | 1740 |

```
atttccaat tagtcctatt gaaactgtac cagtaaaatt aaagtcaggg atgatggtc    1800 caagagttaa acaatggcca ttgacagaag agaaaataaa agcactaata gaaatttgta   1860
cagaaatgga aaaggaagga aaactttcaa gaattggacc tgaaaatcca tacaatactc   1920
caatatttgc cataaagaaa aaagacagta ctaagtggag aaaattagta gatttcagag   1980
aacttaataa gagaactcaa gatttctggg aagttcaact aggaatacca catcctgcag   2040
ggctaaaaaa gaaaaaatca gtaacagtac tggaggtggg tgatgcatat ttttcagttc   2100
ccttatatga agactttaga aaatacactg cattcaccat acctagtata acaatgaga    2160 caccaggaat tagatatcag tacaatgtgc ttccacaagg atggaaagga tcaccggcaa   2220
tattccaaag tagcatgaca aaaatttag aaccttttag aaaacaaaat ccagaagtgg    2280
ttatctacca atacatggac gatttgtatg taggatctga cttagaaata gggcagcata   2340
gaataaaaat agaggaatta aggggacacc tattgaagtg gggatttacc acaccagaca   2400
aaaatcatca gaaggaacct ccatttcttt ggatgggtta tgaactccat cctgataaat   2460
ggacagtaca gcctataaaa ctgccagaaa agaaagctg gactgtcaat gatctgcaga    2520
agttagtggg gaaattaaat tgggcaagtc aaatttattc aggaattaaa gtaagacaat   2580
tatgcaaatg ccttagggga accaaagcac tgacagaagt agtaccactg acagaagaag   2640
cagaattaga actggcagaa aacagggaac ttctaaaaga aacagtacat ggagtgtatt   2700
atgacccatc aaaagactta atagcagaaa tacagaaaca aggcaagac caatggacat     2760 atcaaattta tcaagaacaa tataaaaatt tgaaacagg aaagtatgca agaggagga     2820 gtacccacac taatgatgta aaacaattaa cagaggcagt gcaaaaaata gcccaagaat   2880
gtatagtgat atggggaaag actcctaaat tcagactacc catacaaaag gaaacatggg   2940
aaacatggtg gacagagtat tggcaggcca cctggattcc tgagtgggag tttgtcaata   3000
ccctcccttt ggttaaatta tggtaccagt tagagaagga acccatagta ggagcagaaa   3060
ccttctaa                                                            3068

<210> SEQ ID NO 6
<211> LENGTH: 9
<212> TYPE: PRT
<213> ORGANISM: Human immunodeficiency virus type 1

<400> SEQUENCE: 6

Ala Met Gln Met Leu Lys Glu Thr Ile
1               5

<210> SEQ ID NO 7
<211> LENGTH: 15
<212> TYPE: PRT
<213> ORGANISM: Human immunodeficiency virus type 1

<400> SEQUENCE: 7

Asp Thr Glu Val His Asn Val Trp Ala Thr His Ala Cys Val Pro
1               5                   10                  15

<210> SEQ ID NO 8
<211> LENGTH: 15
<212> TYPE: PRT
<213> ORGANISM: Human immunodeficiency virus type 1

<400> SEQUENCE: 8

Gln Gln Gln Ser Asn Leu Leu Arg Ala Ile Glu Ala Gln Gln His
1               5                   10                  15
```

```
<210> SEQ ID NO 9
<211> LENGTH: 13
<212> TYPE: PRT
<213> ORGANISM: Human immunodeficiency virus type 1

<400> SEQUENCE: 9

Glu Leu Arg Gln His Leu Leu Arg Trp Gly Leu Thr Thr
1               5                   10

<210> SEQ ID NO 10
<211> LENGTH: 14
<212> TYPE: PRT
<213> ORGANISM: Human immunodeficiency virus type 1

<400> SEQUENCE: 10

His Gly Val Tyr Tyr Asp Pro Ser Lys Asp Leu Ile Ala Glu
1               5                   10
```